(12) United States Patent
Singh et al.

(10) Patent No.: US 6,916,612 B2
(45) Date of Patent: Jul. 12, 2005

(54) SETS OF OLIGONUCLEOTIDE-BINDING E-TAG PROBES

(75) Inventors: Sharat Singh, San Jose, CA (US); Tracy Matray, San Lorenzo, CA (US); Ahmed Chenna, Sunnyvale, CA (US)

(73) Assignee: Aclara Biosciences, Inc., Mountain View, CA (US)

(*) Notice: Subject to any disclaimer, the term of this patent is extended or adjusted under 35 U.S.C. 154(b) by 0 days.

(21) Appl. No.: 09/825,246

(22) Filed: Apr. 2, 2001

(65) Prior Publication Data

US 2002/0015954 A1 Feb. 7, 2002

Related U.S. Application Data

(63) Continuation of application No. 09/698,846, filed on Oct. 27, 2000, now Pat. No. 6,627,400, and a continuation of application No. 09/684,386, filed on Oct. 4, 2000, now abandoned, and a continuation of application No. 09/602,586, filed on Jun. 21, 2000, now Pat. No. 6,514,700, and a continuation of application No. 09/561,579, filed on Apr. 28, 2000, now Pat. No. 6,682,887, and a continuation of application No. 09/303,029, filed on Apr. 30, 1999, now Pat. No. 6,322,980.

(51) Int. Cl.[7] .......................... C12Q 1/68; C07H 21/04; C07H 21/00; B01D 57/02

(52) U.S. Cl. ..................... 435/6; 536/22.1; 536/24.3; 536/25.32; 204/450; 206/569

(58) Field of Search ......................... 435/6; 536/23.1, 536/24.3, 25.32; 204/450; 206/569

(56) References Cited

U.S. PATENT DOCUMENTS

| | | | |
|---|---|---|---|
| 4,675,300 A | | 6/1987 | Zare et al. |
| 5,324,401 A | | 6/1994 | Yeung et al. |
| 5,459,078 A | * | 10/1995 | Kline et al. ................. 436/518 |
| 5,470,705 A | | 11/1995 | Grossman et al. |
| 5,470,967 A | * | 11/1995 | Huie et al. .................. 536/24.3 |
| 5,536,834 A | | 7/1996 | Singh et al. |
| 5,560,811 A | | 10/1996 | Briggs et al. |
| 5,565,324 A | | 10/1996 | Still et al. |
| 5,573,906 A | | 11/1996 | Bannwarth et al. |
| 5,580,732 A | | 12/1996 | Grossman et al. |
| 5,624,800 A | | 4/1997 | Grossman et al. |
| 5,703,222 A | | 12/1997 | Grossman et al. |
| 5,719,028 A | | 2/1998 | Dahlberg et al. |
| 5,721,099 A | | 2/1998 | Still et al. |
| 5,723,591 A | | 3/1998 | Livak et al. |
| 5,744,306 A | * | 4/1998 | Murtagh, Jr. et al. ........... 435/6 |
| 5,756,726 A | | 5/1998 | Hemmi et al. |
| 5,789,172 A | | 8/1998 | Still et al. |
| 5,807,675 A | | 9/1998 | Davalian et al. |
| 5,807,682 A | | 9/1998 | Grossman et al. |
| 5,811,239 A | | 9/1998 | Frayne |
| 5,843,666 A | | 12/1998 | Akhavan-Tafti et al. |
| 5,851,770 A | * | 12/1998 | Babon et al. .................. 435/6 |
| 5,874,213 A | | 2/1999 | Cummins et al. |
| 5,876,930 A | | 3/1999 | Livak et al. |
| 5,989,871 A | | 11/1999 | Grossman et al. |
| 5,998,140 A | | 12/1999 | Dervan et al. |
| 6,001,579 A | | 12/1999 | Still et al. |
| 6,045,676 A | | 4/2000 | Mathies et al. |
| 6,090,947 A | | 7/2000 | Dervan et al. |
| 6,251,581 B1 | * | 6/2001 | Ullman et al. ................. 435/4 |

FOREIGN PATENT DOCUMENTS

| | | |
|---|---|---|
| WO | WO 97/28275 | 8/1997 |
| WO | WO 98/01533 | 1/1998 |
| WO | WO 99/13108 | 3/1999 |
| WO | WO 99/64519 | 12/1999 |
| WO | WO 00/66607 | 11/2000 |

OTHER PUBLICATIONS

Adam, W. and Liu, J.–C., "Photooxygenation (Singlet Oxygen) of Tetrathioethylenes" *J. Am. Chem. Soc.* 94:1206–1209 (1972).

Adam, W., et al., "Photooxygenation of Vinyl Sulfides: Substituent Effects on the [2+2] Cycloaddition versus Schenk Ene Reaction Modes" *Tetrahedron Letters* 36(43):7853–7854 (1995).

Ando, W., et al., "Singlet Oxygen Reaction–II alkylthiosubstituted ethylene" *Tetrahedron Letters* 29:1507–1513 (1973).

Ando, W., et al., "Singlet Oxygen Reaction. III. 'Solvent and Temperature Effects' on the Photosensitized Oxygenation of Vinyl Sulfides and Vinyl Ethers" *J. Am. Chem. Soc.* 96:6766–6768 (1974).

Ando, W., et al., "Singlet Oxygen Reaction. IV. Photooxygenation of Enamines Involving a Two–Step Cleavage of a 1,2–Dioxetane Intermediate" *J. Am. Chem. Soc.* 97:5028–5029 (1975).

Ando, W., et al., "Singlet Oxygen Reaction V. Ring Size Effects on the Decomposition of Sulfur Substituted 1,2–Dioxetane" *Tetrahedron Letters* 47:4127–4130 (1975).

(Continued)

*Primary Examiner*—Kenneth R. Horlick
*Assistant Examiner*—Joyce Tung
(74) *Attorney, Agent, or Firm*—Stephen C. Macevicz

(57) ABSTRACT

Probe sets for the multiplexed detection of known, selected nucleotide target sequences are provided. Detection involves the release of identifying tags as a consequence of target recognition. The probe sets include electrophoretic tag probes or "e-tag probes", comprising a detection region and a mobility-defining region called the mobility modifier, both linked to a target-binding moiety. The target-binding moiety of the e-tag probes hybridizes to complementary target sequences followed by nuclease cleavage of the e-tag probes and release of detectable e-tags or e-tag reporters. The mixture is exposed to a capture agent which binds uncleaved and/or partially cleaved e-tag probes, followed by electrophoretic separation. In a multiplexed assay, different released e-tag reporters may be separated and detected providing for target identification.

13 Claims, 45 Drawing Sheets

OTHER PUBLICATIONS

Brenner, S. and Lerner, R.A., "Encoded combinatorial chemistry" *Proc. Natl. Acad. Sci. USA* 89:5381–5383 (1992).

Hacia, J.G., et al., "Detection of heterozygous mutations in BRCA1 using high density ologonucleotide arrays and two–colour fluorescence analysis" *Nature Genetics.* 14:441–447 (1996).

Haff, L.A. and Smirov, I.P., "Multiplex genotyping of PCR products with MassTag–labeled primers" *Nucleic Acids Res.* 25(18):3749–3750 (1997).

Lee, L.G., et al., "Allelic discrimination by nick–translation PCR with fluorogenic probes" *Nucleic Acid Research* 21(16):3761–3766 (1993).

Marino, M.A., et al., "Characterization of mitochondrial DNA using low–stringency single specific primer amplification analyzed by laser induced fluorescence–capillary electrophoresis" *Electrophoresis* 17:1499–1504 (1996).

Matthews, J.A. and Kricka, L.J., "Analytical Strategies for the Use of DNA Probes" *Anal. Biochem.* 169:1–25 (1988).

Pastinen, T., et al., "Multiplex, fluorescent, solid–phase minisequencing for efficient screening of DNA sequencing variation" *Clinical Chemistry* 42(9):1391–1397 (1996).

Ross, P.L., et al., "Discrimination of Single–Nucleotide Polymorphisms in Human DNA Using Peptide Nucleic Acid Probes Detected by MALDI–TOF Mass Spectrometry" *Anal. Chem.* 69:4197–4202 (1997).

Still, W.C., "Discovery of Sequence–Selective Peptide Binding by Synthetic Receptors Using Encoded Combinatorial Libraries" *Accounts of Chem. Res.* 29:155–163 (1996).

Ullman, E.F., et al., "Luminescent oxygen channeling immunoassay: Measurement of particle binding kinetics by chemiluminescence" *Proc. Natl. Acad. Sci.,* 91:5426–5430 (1994).

Wang, D.G., et al., "Large–Scale Identification, Mapping, and Genotyping of Single–Nucleotide Polymorphisms in the Human Genome" *Science* 280(5366):1077–1082 (1997).

Wasserman, H.H. and Terao, S., "Enamine–singlet oxygen reactions. α–diketones from intermediate amino dioxetanes" *Tetrahedron Letters* 21:1735–1738 (1975).

Wetmur, J.G., "DNA Probes: Applications of the Principles of Nucleic Acid Hybridization" *Critical Rev. in Biochem. and Molecular Biol.* 26(3/4):227–259 (1991).

White, T.J., "The future of PCR technology: diversification of technologies and applications" *Trends in Biotechnology* 14:478–483 (1996).

Woolley, A.T., et al., "Functional Integration of PCR Amplification and Capillary Electrophoresis in a Microfabricated DNA Analysis Device" *Anal. Chem.* 68:4081–4086 (1996).

Zalika, K.A., et al., "Mechanisms of 1,2–dioxetane decomposition: the role of electron transfer" *Photochem. Photobiol.* 30:35–44 (1979).

\* cited by examiner

CCA GCA ACC AAT GAT GCC CGT T-TAMRA-3'
CA GCA ACC AAT GAT GCC CGT T-TAMRA-3'

CCA GCA AGC ACT GAT GCC TGT T-TAMRA-3'
CA GCA AGC ACT GAT GCC TGT T-TAMRA-3'

Fluorescent Dyes

| | Absorbance Maxima | Emission Maxima |
|---|---|---|
| Fluorescein | 494nm | 525nm |
| Tetrachloro fluorescein | 521nm | 536nm |
| TAMRA | 565nm | 580nm |

Cleaved Fragments:

| e-tag Reporter | Elution Time on CE, min | Mass |
|---|---|---|
| | 6.4 | 778 |
| | 7.1 | 925 |
| | 7.3 | 901 |
| | 7.7 | 994 |
| | 8.0 | 985 |
| | 9.25 | 961 |

Fig. 5

| e-tag Reporter | Charge | Elution Time, min |
|---|---|---|
|  | -8 | 12.1* |
|  | -9 | 12.7 |
|  | -8 | 12.8 |
|  | -7 | 13.1 |
|  | -6 | 13.0 |
|  | -6 | 13.4 |
|  | -5 | 12.8* |
|  | -5 | 13.2* |
|  | -5 | 14.8 |
|  | -6 | 17.3 |
|  | -5 | 17.0 |
|  | -4 | 15.2* |
|  | -4 | 16.5 |

ACLA001

ACLA002

ACLA003

ACLA004

ACLA005

ACLA006

ACLA007

ACLA008

ACLA009

ACLA010

ACLA011

ACLA012

ACLA089

ACLA090

ACLA091

ACLA092

ACLA093

ACLA094

ACLA095

ACLA096

ACLA097

SETS OF OLIGONUCLEOTIDE-BINDING E-TAG PROBES

CROSS-REFERENCE TO RELATED APPLICATIONS

This application is a continuation of Ser. No. 09/303,029 filed 30 Apr. 1999 now U.S. Pat. No. 6,322,980; Ser. No. 09/561,579 filed 28 Apr. 2000 now U.S. Pat. No. 6,682,887; Ser. No. 09/602,586 filed 21 Jun. 2000 now U.S. Pat. No. 6,514,700; Ser. No. 09/684,386 filed 4 Oct. 2000 now abandoned; and Ser. No. 09/698,846 filed 27 Oct. 2000 now U.S. Pat. No. 6,627,400, all of which are incorporated herein by reference in their entirety.

FIELD OF THE INVENTION

The present invention relates to separable compositions, methods, and kits for use in multiplexed assay detection of known, selected target nucleotide sequences.

BACKGROUND OF THE INVENTION

The need to determine many analytes or nucleic acid sequences (for example multiple pathogens or multiple genes or multiple genetic variants) in blood or other biological fluids has become increasingly apparent in many branches of medicine. Most multi-analyte assays, such as assays that detect multiple nucleic acid sequences, involve multiple steps, have poor sensitivity, a limited dynamic range (typically on the order of 2 to 100-fold differences and some require sophisticated instrumentation. Some of the known classical methods for multianalyte assays include the following:

a. The use of two different radioisotope labels to distinguish two different analytes.

b. The use of two or more different fluorescent labels to distinguish two or more analytes.

c. The use of lanthanide chelates where both lifetime and wavelength are used to distinguish two or more analytes.

d. The use of fluorescent and chemiluminescent labels to distinguish two or more analytes.

e. The use of two different enzymes to distinguish two or more analytes.

f. The use of enzyme and acridinium esters to distinguish two or more analytes.

g. Spatial resolution of different analytes, for example on arrays, to identify and quantify multiple analytes.

h. The use of acridinium ester labels where lifetime or dioxetanone formation is used to quantify two different viral targets.

As the human genome is elucidated, there will be numerous opportunities for performing assays to determine the presence of specific sequences, distinguishing between alleles in homozygotes and heterozygotes, determining the presence of mutations, evaluating cellular expression patterns, etc. In many of these cases one will wish to determine in a single reaction, a number of different characteristics of the same sample. In many assays, there will be an interest in determining the presence of specific sequences, whether genomic, synthetic, or cDNA. These sequences may be associated particularly with genes, regulatory sequences, repeats, multimeric regions, expression patterns, and the like. There will also be an interest in determining the presence of one or more pathogens, their antibiotic resistance genes, genetic subtype and the like. The need to identify and quantify a large number of bases or sequences, potentially distributed over centimorgans of DNA, offers a major challenge. Any method should be accurate, reasonably economical in limiting the amount of reagents required and provide for a highly multiplexed assay, which allows for differentiation and quantitation of multiple genes, and/or snp determination, and/or gene expression at the RNA or protein level.

The need to study differential expression of multiple genes to determine toxicologically relevant outcomes or the need to screen transfused blood for viral contaminants with high sensitivity is clearly evident. Finally, while nucleic acid sequences provide extreme diversity for situations that may be of biological or other interest, there are other types of compounds, such as proteins in proteomics that may also offer opportunities for multiplexed determinations.

There is and will continue to be comparisons of the sequences of different individuals. It is believed that there will be about one polymorphism per 1,000 bases, so that one may anticipate that there will be an extensive number of differences between individuals. By single nucleotide polymorphism (SNPs) is intended that there will be a prevalent nucleotide at the site, with one or more of the remaining bases being present in a substantially smaller percent of the population. While other genetic markers are available, the large number of SNPs and their extensive distribution in the chromosomes make SNPs an attractive target. Also, by determining a plurality of SNPs associated with a specific phenotype, one may use the SNP pattern as an indication of the phenotype, rather than requiring a determination of the genes associated with the phenotype. For the most part, the SNPs will be in non-coding regions, primarily between genes, but will also be present in exons and introns. In addition, the great proportion of the SNPs will not affect the phenotype of the individual, but will clearly affect the genotype. The SNPs have a number of properties of interest. Since the SNPs will be inherited, individual SNPs and/or SNP patterns may be related to genetic defects, such as deletions, insertions and mutations, involving one or more bases in genes. Rather than isolating and sequencing the target gene, it will be sufficient to identify the SNPs involved. In addition, the SNPs may also be used in forensic medicine to identify individuals.

Thus an assay for the differentiation and quantitation of multiple genes, and/or snp determination, and/or gene expression at the RNA or protein level, that has higher sensitivity, a large dynamic range ($10^3$ to $10^4$-fold differences in target levels), a greater degree of multiplexing, and fewer and more stable reagents would increase the simplicity and reliability of multianalyte assays, and reduce their costs.

BRIEF DESCRIPTION OF THE RELATED ART

Holland (*Proc. Natl. Acad. Sci. USA* (1991) 88:7276) discloses that the exonuclease activity of the thermostable enzyme *Thermus aquaticus* DNA polymerase in PCR amplification to generate specific detectable signal concomitantly with amplification.

The TaqMan® assay is discussed by Lee in *Nucleic Acid Research* (1993) 21:16 3761).

White (Trends Biotechnology (1996) 14(12): 478–483) discusses the problems of multiplexing in the TaqMan assay.

Marino, *Electrophoresis* (1996) 17:1499 describes low-stringency-sequence specific PCR (LSSP-PCR). A PCR amplified sequence is subjected to single primer amplification under conditions of low stringency to produce a range of different length amplicons. Different patterns are obtained when there are differences in sequence. The patterns are unique to an individual and of possible value for identity testing.

Single strand conformational polymorphism (SSCP) yields similar results. In this method the PCR amplified DNA is denatured and sequence dependent conformations of the single strands are detected by their differing rates of migration during gel electrophoresis. As with LSSP-PCR above, different patterns are obtained that signal differences in sequence. However, neither LSSP-PCR nor SSCP gives specific sequence information and both depend on the questionable assumption that any base that is changed in a sequence will give rise to a conformational change that can be detected. Pastinen, *Clin. Chem.* (1996) 42:1391 amplifies the target DNA and immobilizes the amplicons. Multiple primers are then allowed to hybridize to sites 3' and contiguous to a SNP (single nucleotide polymorphism) site of interest. Each primer has a different size that serves as a code. The hybridized primers are extended by one base using a fluorescently labeled dideoxynucleoside triphosphate. The size of each of the fluorescent products that is produced, determined by gel electrophoresis, indicates the sequence and, thus, the location of the SNP. The identity of the base at the SNP site is defined by the triphosphate that is used. A similar approach is taken by Haff, *Nucleic Acids Res.* (1997) 25:3749 except that the sizing is carried out by mass spectrometry and thus avoids the need for a label. However, both methods have the serious limitation that screening for a large number of sites will require large, very pure primers that can have troublesome secondary structures and be very expensive to synthesize.

Hacia, *Nat. Genet.* (1996) 14:441 uses a high-density array of oligonucleotides. Labeled DNA samples were allowed to bind to 96,600 20-base oligonucleotides and the binding patterns produced from different individuals were compared. The method is attractive in that SNPs can be directly identified, but the cost of the arrays is high and non-specific hybridization may confound the accuracy of the genetic information.

Fan (1997, October 6–8, IBC, Annapolis Md.) has reported results of a large scale screening of human sequence-tagged sites. The accuracy of single nucleotide polymorphism screening was determined by conventional ABI resequencing.

Ross in *Anal. Chem.* (1997) 69:4197 discusses allele specific oligonucleotide hybridization along with mass spectrometry.

Brenner and Lerner, *PNAS* (1992) 89:5381, suggested that compounds prepared by combinatorial synthesis can each be labeled with a characteristic DNA sequence. If a given compound proves of interest, the corresponding DNA label is amplified by PCR and sequenced, thereby identifying the compound.

W. Clark Still, in U.S. Pat. No. 5,565,324 and in Accounts of Chem. Res., (1996) 29:155, uses a releasable mixture of halocarbons on beads to code for a specific compound on the bead that is produced during synthesis of a combinatorial library. Beads bearing a compound of interest are treated to release the coding molecules and the mixture is analyzed by gas chromatography with flame ionization detection.

U.S. Pat. No. 5,807,682 describes probe compositions for detecting a plurality of nucleic acid targets.

SUMMARY OF THE INVENTION

Sets of electrophoretic tag (e-tag) probes for the multiplexed detection of known, selected target nucleotide sequences are provided.

The e-tag probe sets comprise j members, and have the form, $(D, M_j)$-$N$-$T_j$, where (a) D is a detection group comprising a detectable label; (b) $M_j$ is a mobility modifier, having a particular charge/mass ratio; (c) N is a nucleotide joined to $U_1$ in $T_j$ through a nuclease-cleavable bond; and (d) $T_j$ is an oligonucleotide target-binding moiety that has a sequence of nucleotides $U_i$ connected by intersubunit linkages $B_{i,\ i+1}$, where i includes all integers from 1 to n, and n is sufficient to allow the moiety to specifically hybridize with a target nucleotide sequence.

When the oligonucleotide target-binding moiety of an e-tag probe of the invention interacts with a target oligonucleotide, an e-tag reporter of the form $(D, M_j)$-$N$ is released. The mobility modifier imparts a unique and known electrophoretic mobility to each released e-tag reporter which is within a selected range of electrophoretic mobilities with respect to other e-tag reporters of the same form in the probe set. The e-tag reporter does not itself contain nuclease-cleavable bonds.

The sets include e-tag probes having the form, $M_j$-$D$-$N$-$T_j$ and $D$-$M_j$-$N$-$T_j$, where the corresponding e-tag reporters have the form $M_j$-$D$-$N$ and $D$-$M_j$-$N$, respectively.

The target-binding moiety of each e-tag probe of the set contains at least one modification selected from the following:

(i) at least one nuclease-resistant bond $B_{i,\ i-1}$, where i includes at least 1;

(ii) a capture ligand, e.g., biotin, bound to $U_1$ and capable of binding specifically to a capture agent; and (iii) a nuclease-resistant bond $B_{i,\ i-1}$, where i includes at least 1, and a capture ligand bound to at least one nucleotide $U_i$ and capable of binding specifically to a capture agent, where $i \geq 1$.

The invention further provides sets of e-tag probes wherein the nuclease-cleavable bond is a phosphodiester bond, and the nuclease-resistant bond(s) in the target-binding moiety are one or more of thiophosphate, phosphinate, phosphoramidate, amide, and boronate linkages.

In the probe sets of the invention, the mobility modifier may have one or more of the following characteristics:

(i) a unique charge/mass ratio due to variations in mass, but not charge;

(ii) a unique charge/mass ratio due to changes in both mass and charge;

(iii) a unique charge/mass ratios of between −0.001 and 0.5;

(iv) a structure that includes a selected number of negatively charged and/or positively charged amino acids; and (v) a structure that includes an alkyl chain, and differs from other $M_j$ in the set by 1–3 methylene groups in the chain.

In one aspect, the probe sets comprise at least 5 probes, and in a related aspect, the probe sets comprise at least 9 probes.

The label component of the probe sets of the invention may be a fluorophore, a chromophore, or an electrochemical compound capable of a detectable reaction in the presence of a redox agent. In addition, the label component of the probe set may have a selected mass and charge.

Further, a given set of e-tags probes for multiplexed detection of known, selected target nucleotide sequences may contain subsets of probes, each subset having a label with a unique mass/charge ratio.

BRIEF DESCRIPTION OF THE DRAWINGS

FIG. 5 illustrates E-tags that have been separated on a LabCard. (Detection: 4.7 cm; 200 V/cm.)

FIGS. 25A and B reflect the results of experiments showing the formation of 5 different cleavage products in the PCR amplification of ANF (anti-nuclear factor) with (A) and without (B) the thiophosphate linkage. FIGS. 25C and D reflect the results of experiments showing the formation of 5 different cleavage products in the PCR amplification of GAPDH, with (C) and without (D) the thiophosphate linkage.

DESCRIPTION OF THE SPECIFIC EMBODIMENTS

I. Definitions

Figures 1A, 1B, 1C:
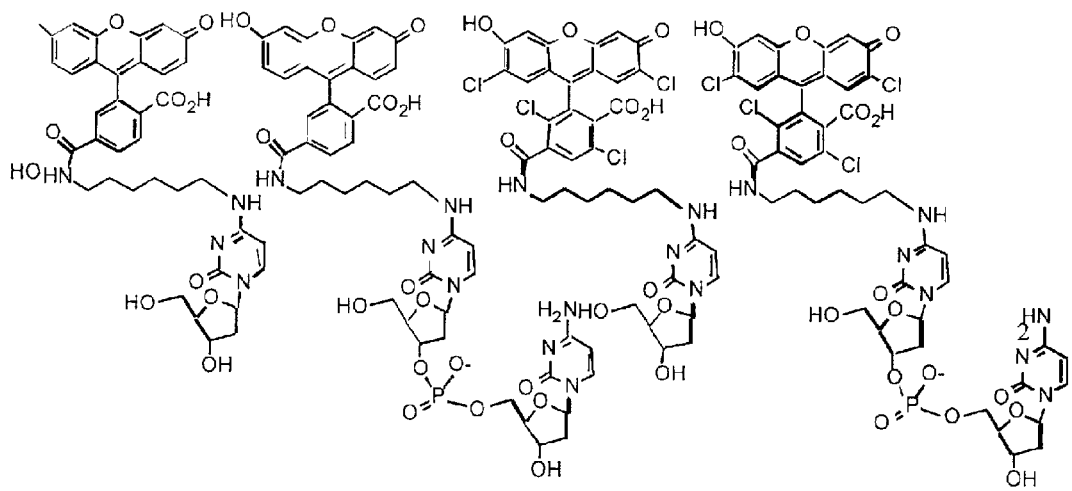
FIGS. 1A, B and C depict the snp detection sequences for two snp alleles (A), the optical characteristics of the fluorescent dyes (B), and the cleaved fragments from the snp detection sequences (C).

In defining the terms below, it is useful to consider the makeup of the "electrophoretic probes" that form part of the invention and/or are used in practicing the method of the invention. An electrophoretic probe has four basic components or moieties: (i) a detection group or moiety, (ii) a mobility modifier, (iii) a target-binding moiety, and (iv) a linking group that links the mobility modifier and detection group to the target-bonding moiety. These terms will first be examined in the context of the functioning of the electrophoretic probes in the invention, then more fully defined by their structural features.

The function of an electrophoretic probe in the invention is first to interact with a target, such as a single-stranded nucleic acid, a ligand-binding agent, such as an antibody or receptor, or an enzyme, e.g., as an enzyme substrate. The "portion", "region" or "moiety" of the probe which binds to the target is the "target-binding moiety" or "target-binding region" or "target-binding portion" ("T"). After the target-binding moiety of an electrophoretic probe binds to a target, and typically as a result of such binding, the linking group of the electrophoretic probe may be cleaved to release an "electrophoretic tag" or "e-tag" or "e-tag reporter" which has a unique charge-to-mass ratio and thus a unique electrophoretic mobility in a defined electrophoretic system. The e-tag reporter is composed of the detection group, mobility modifier, and any residue of the linking group that remains associated with released reporter e-tag after cleavage. Therefore, the second function of the electrophoretic probe is to release an e-tag reporter which can be identified according to its unique and known electrophoretic mobility.

According to an important feature of the invention, there is provided a set of electrophoretic probes, each of which has a unique target-binding moiety and an associated "e-tag moiety" that imparts to the associated e-tag reporter, a unique electrophoretic mobility by virtue of a unique charge to mass ratio. In general, the unique charge to mass ratio of an e-tag moiety is due to the chemical structure of the mobility modifier, since the detection group and linking-group residue (if any) will be common to any set of electrophoretic probes. However, it is recognized that unique charge and/or mass contributions to the e-tag reporters can be made by the detection group as well. For example, a set of electrophoretic probes may be made up of a first subset having a group of mobility modifiers which impart unique electrophoretic mobilities to the subset in combination with a detection group having one defined charge and/or mass, and a second subset having the same group of mobility modifiers in combination with a second detection group with a different charge and/or mass, thus to impart electrophoretic mobilities which are unique among both subsets.

The different target-binding moieties in a set of electrophoretic probes are typically designated "$T_j$", where the set of probes contains n members, and each $T_j$, j=1 to j=n is different, i.e., will bind specifically and/or with unique affinities to different targets. A set of electrophoretic probes of the invention typically includes at least about 5 members, i.e., n is preferably 5 or more, typically 10–100 or more.

A "reporter moiety" "R" or a "detection group" "D" are equivalent terms referring to a chemical group or moiety that is capable of being detected by a suitable detection system, particular in the context of detecting molecules containing the detection group after or during electrophoretic separation. One preferred detection group is a fluorescent group that can be readily detected during or after electrophoretic separation of molecules by illuminating the molecules with a light source in the excitation wavelength and detecting fluorescence emission from the irradiated molecules. Exemplary fluorescent moieties will be given below. As noted above, the detection group is typically common among a set or subset of different electrophoretic probes, but may also differ among probe subsets, contributing to the unique electrophoretic mobilities of the released e-tag reporter.

The "mobility modifier" "M" is a generally a chemical group or moiety that is designed to have a particular charge to mass ratio, and thus a particular electrophoretic mobility in a defined electrophoretic system. Exemplary types of mobility modifiers are discussed below. In a set of n electrophoretic probes, each unique mobility modifier is designated $M_j$, where j=1 to n, as above. The mobility modifier may be considered to include a mass-modifying region and/or a charge-modifying region or a single region that acts as both a mass- and charge-modifying region. The mobility modifying region may also be referred to as M*, C*, L, a bond, a linking group, a mobility/mass identifying region or "mir", a charge-imparting moiety and a mobility region.

The detection group and mobility modifier in the electrophoretic probe form an "e-tag moiety" which is linked to the target-binding moiety by a "linking group" which may be only a covalent bond which is cleavable under selected cleaving conditions, or a chemical moiety or chain, such as a nucleotide and associated phosphodiester bond, an oligonucleotide with an internal cleavable bond, an oligopeptide, or an enzyme substrate, that contains a cleavable chemical bond. Cleavage typically occurs as the result of binding of the probe to the target, which is followed by enzyme or catalyzed cleavage of the linking-group bond. The linking group is variously referred to herein as "L" and "N", depending on the nature and role of the linking group as will be defined below.

The linking group may or may not contribute a linking-group "residue" to the released e-tag reporter, also dependent on the nature of the linking group and the site of cleavage. For example, where the linking group is a covalent bond, or cleavage of the linking group occurs immediately adjacent the "e-tag moiety", the linking group will leave no residue, i.e., will not contribute additional mass and charge to the released e-tag reporter. Similarly, where the linking group is a chemical group or chain which is cleaved internally or immediately adjacent the target-binding moiety, cleavage of the linking group will leave a residual mass and, possible charge contribution to the released e-tag reporter. In general, this contribution will be relatively small, and the same for each different released e-tag (assuming a common linking group within the probe set). As such, the residue will not effect the relative electrophoretic mobilities of the released e-tag reporters, nor the ability to resolve the e-tag reporters into electrophoretic species that can be uniquely identified.

The following definitions are to be understood in the context of the above function of the various components of electrophoretic probes and e-tag reporters. In some case, structure designations based on different lettering schemes are employed, and the equivalency between or among structures with different lettering schemes will be understood by those skilled in the art, in view of the intended function of the structure being referred to.

An "electrophoretic probe" refers to one of a set of probes of the type described above having unique target-binding moieties and associated e-tag moieties moieties. The probes are variously expressed by the following equivalent forms herein:

(a) $(D, M_j)$-L-$T_j$, or $(D, M_j)$-N-$T_j$, where D is a detection moiety, $M_j$ is the jth mobility modifier, $T_j$ is the jth target binding agent, and the linking group is represented by L and by N (when the linking group is the 5'-terminal nucleotide of an oligonucleotide target-binding moiety). In this and the following structural designations, $(D, M_j)$- indicates that either the detection group or the mobility modifier is joined to the linking group, i.e., either $(D, M_j)$ or $(M_j, D)$-.

(b) $(R, M_j)$-L-$T_j$, or $(R, M_j)$-N-$T_j$, where R is a detection moiety or reporter group, and $M_j$, Tj, and L and N are as in (a).

(c) R-L-T or L-R-T, where R is a label, particularly a fluorescer, L is a mir, a bond or a linking group, where L and the regions to which L is attached provide for the variation in mobility of the e-tags. T comprises a portion of the target-binding region, particularly a nucleoside base, purine or pyrimidine, and is the base, a nucleoside, nucleotide or nucleotide triphosphate, an amino acid, either naturally occurring or synthetic, or other functionality that may serve to participate in the synthesis of an oligomer, when T is retained, and is otherwise a functionality resulting from the cleavage between L, the mir, and the target-binding region. (in the corresponding e-tag reporter).

A "set" or "group", "plurality" or "library" of electrophoretic probes refers to a plurality of electrophoretic probes having typically at least five, typically 10–100 or more probes with different unique target-binding moieties and associated e-tag moieties.

As used herein, the term "electrophoretic tag probe set" or "e-tag probe set" refers to a set of probes for use in detecting each or any of a plurality of known, selected target nucleotide sequences, or for detecting the binding of, or interaction between, each or any of a plurality of ligands and one or more target antiligands.

The term "target-binding moiety" or "$T_j$" refers to the component of an e-tag probe that participates in recognition and specific binding to a designated target. The target-binding moiety may also be referred to as T or T', or may be defined based on the type of target, e.g., as a snp detection sequence or an oligonucleotide detection sequence.

In one general embodiment of the target-binding moiety for use in detection of nucleic acid targets, $T_j$ is an oligonucleotide target-binding moiety. In such cases, $T_j$ has a sequence of nucleotides $U_1$ connected by intersubunit linkages:

$U_1 = U_2 = U_3 = U_4 = U_5 = U_6 = U_i$ where = corresponds to intersubunit linkages $B_{i, i+1}$, where i includes all integers from 1 to n, and n is sufficient to allow the moiety to hybridize specifically with a target nucleotide sequence. Where the target-binding moiety is an oligonucleotide, and enzyme cleavage to release the e-tag reporter occurs between the first and second 5' nucleotides (between $U_1$ and $U_2$ above), the linking group and nucleotides forming the target-binding sequence can be expressed in either of two equivalent representations.

In one exemplary representation, $U_1$ is considered the 5' nucleotide of the target-binding moiety (as in the representation above), and cleavage occurs within this moiety, that is, at a nuclease-susceptible bond between the first and second nucleotides of the target moiety (between $U_1$ and $U_2$, above). In this representation, the bond between the first and second nucleotides ($B_{1,2}$ in the above nomenclature) is the site of cleavage and all downstream bonds are represented by $B_{i, i+1}$, where "i" is 2 or greater. Typically the penultimate bond is nuclease-resistant, however the target binding moiety may include more than one nuclease-resistant linkage adjacent to the nuclease-susceptible linkage, such that the probe will yield a single released e-tag reporter species upon cleavage. In this representation, a capture ligand ("C"), may be bound to the penultimate nucleotide ($U_2$).

In another exemplary representation, the 5' nucleotide is designated "N", and the nuclease-susceptible bond that links it to the 5' nucleotide ($U_1$) of the target binding moiety is considered as the linking group. In other words, in this representation, N and all downstream nucleotides are considered as the target binding region. The same oligonucleotide above would now be expressed as $N = U_1 = U_2 = U_3 = U_4 = U_5 = U_6 = U_i$, where N is the 5' nucleotide and participates in target recognition. In this representation, a capture ligand ("C"), may be bound to the ultimate nucleotide ($U_1$).

In one application of this embodiment, the e-tag probe is referred to as a snp detection sequence, a fluorescence snp detection sequence or an oligonucleotide detection sequence.

In another generalized embodiment for use in detection of non-nucleic acid targets, the target-binding moiety, $T_j$ is or includes a ligand capable of binding to or interacting with a target antiligand and L is a linking group connected to $T_j$ by a bond that is cleavable by a selected cleaving agent when the probe is bound to or interacting with the target antiligand. L may also be referred to as a L", a terminal linking region, a terminal linking group.

"Electrophoretic tag" refers to a composition or reagent for unique identification of an entity of interest during separation. An e-tag has the fundamental structure given as $(D, M_j)$-L, where D and $M_j$ are the detection group and jth mobility modifier, as defined above, and L is the linking group, and in particular, the bond or residue of the linking group remaining after cleavage. Here the e-tag moiety $(D, M_j)$ is intended to include both of the structures D-$M_j$-L and $M_j$-D-L. Other equivalent forms of expressing the e-tag are: $(R, M_j)$, $(R, M)$, R-L or L-R where R is a reporter group, $M_j$ or M is a mobility modifier and L is a mobility identifying region (mir), a bond or a linking group.

For purposes of clarity, the concept of an electrophoretic tag is consistently referred to herein as an "e-tag", however various references to "Etag", "ETAG", "eTAG" and "eTag" may be made when referring to an electrophoretic tag. As used herein, the term "electrophoretic tag probe" or "e-tag probe" refers to a reagent used for target recognition, which comprises an e-tag and a target-binding moiety. Upon interaction with the corresponding target, the e-tag undergoes a change resulting in the release of an e-tag reporter. Such an e-tag probe may also be referred to as a binding member.

E-tag probes of the invention find utility in performing multiplexed for detection/analysis of targets including, but not limited to nucleic acid detection, such as sequence recognition, snp detection, transcription analysis or mrna determination, allelic determination, mutation determination, hla typing or mhc determination and haplotype determination, in addition to detection of other ligands, such as proteins, polysaccharides, etc.

As used herein, the term "e-tag reporter" refers to the cleavage product generated as a result of the interaction between an e-tag probe and its target. In one representation, an e-tag reporter comprises the e-tag plus a residual portion of the target binding moiety ($T_j$) (where, as in the nucleotide example, above, one or more nucleotides in the target-binding moiety contain the cleavable linking group), or a residual portion of the linking group (when the latter is considered separate from the target-binding moiety). In another embodiment, the e-tag does not retain any of the target binding moiety. E-tag reporters can be differentiated by electrophoretic mobility or mass and are amenable to electrophoretic separation and detection, although other methods of differentiating the tags may also find use. An e-tag reporter resulting from the interaction of an e-tag probe and a nucleic acid target typically has the form (D, $M_j$)-N, where N is as defined above, the 5'-end terminal nucleotide of a target-binding oligonucleotide.

An e-tag reporter resulting from the interaction of an e-tag probe used to detect the binding of or interaction between a ligand and an antiligand typically has the form (D, $M_j$)-L'. D and $M_j$ are defined above and L' is the residue of L that remains attached to (D, $M_j$) after an e-tag reporter is cleaved from the corresponding e-tag probe.

e-tag reporters may also be described as electrophoretic tags or eTags for use in electrophoresis, released eTags, released e-tags, etc. The e-tag for use in electrophoresis may also be represented by the formula: R-L-T, as described above, where T is retained, and is otherwise a functionality resulting from the cleavage between L, the mir, and the target-binding region.

As used herein, the term "binding event" generally refers to the binding of the target binding moiety of an e-tag probe to its target. By way of example, such binding may involve the interaction between complementary nucleotide sequences or the binding between a ligand and target antiligand.

As used herein, the term "capture ligand", refers to a group that is typically included within the target binding moiety or portion of an e-tag probe and is capable of binding specifically to a "capture agent" or receptor. The interaction between such a capture ligand and the corresponding capture agent may be used to separate uncleaved e-tag probes from released e-tag reporters.

II. Compositions of the Invention

The subject invention provides compositions and methods for improved analysis of complex mixtures, where one is interested in the simultaneous identification of a plurality of entities, such as nucleic acid or amino acid sequences, snps, alleles, mutations, proteins, haptens, protein family members, expression products, etc., analysis of the response of a plurality of entities to an agent that can affect the mobility of the entities, and the like. Libraries of differentiable compounds are provided, where the compounds comprise a mobility-identifying region (including mass-identifying region) ("mir"), that provides for ready identification by electrophoresis or mass spectrometry (differentiation by mobility in an electrical field or magnetic field), by itself or in conjunction with a detectable label. Depending on the determination the product may also include one or more nucleotides or their equivalent, one or more amino acids or their equivalent, a functionality resulting from the release of the target-binding region or a modified functionality as a result of the action of an agent on the target-binding region. The mobility-identifying region or mir may be designated as a mobility modifier given that it provides for ready identification by electrophoresis, by itself or in conjunction with a detectable label.

The methodology involves employing detectable tags that can be differentiated by electrophoretic mobility or mass. The tags comprise mobility-identifying regions joined to a moiety that will undergo a change to produce a product. Depending on the nature of the change, the change may involve a change in mass and/or charge of the mir, the release of the mir from all or a portion of the target-binding region or may provide for the ability to sequester the mir from the starting material for preferential release of the mir. The differentiable tags, whether identified by electrophoresis or mass spectrometry, comprising the mir, with or without the detectable label and a portion of the target-binding region will be referred to as "e-tags."

Such differentiable e-tags, comprising the e-tag with or without a portion of the target-binding region for use in detection may be conveniently referred to as "e-tag reporters". The e-tag reporters are generated as the result of the interaction between an e-tag probe (which comprises an e-tag joined to a target-binding region) and a corresponding target.

The eTag reporters will vary depending upon the method of detection. Groups of at least 10 eTag reporters bound to 10 different binding compounds will be used in the determinations. The eTag reporters will be characterized by being cleavable from the binding compound in the same vessel by the same cleavage mechanism, having a shared characteristic that permits separation and individual detection, being compatible with the determination method and being in the molecular weight range of about 30 to 3000 dal, usually in the molecular weight range of about 35 to 1500 dal. The variation may be mass using a mass spectrometer, where a magnetic field is used for separation, mass/charge ratio using electrokinesis, where an electric field is used for separation, which may also include sieving and/or adsorbing polymers, adsorption, using chromatography, e.g gas chromatography, high pressure liquid chromatography, where polar and van der Waal interactions are used for separation, etc.

In addition, the subject invention employs a variety of reagent systems, where a binding event results in a change in mobility of the e-tag. The binding event is between a target-binding region and a target, and the reagent system recognizes this event and changes the nature of the e-tag containing target-binding region, so that the mobility and/or mass of the product is different from the starting material. The reagent system will frequently involve an enzyme and the reagent system may comprise the target. The effect of the reagent system is to make or break a bond by physical, chemical or enzymatic means. Each of the products of the different e-tag containing target-binding regions can be accurately detected, so as to determine the occurrence of the binding event. Following the binding event, one or more reaction products are produced that exhibit mobilities different from the e-tag probe or probes from which the reaction products derive. The released form of the e-tag or the e-tag reporter exhibits a different mobility and/or mass than the e-tag from which it derives.

The subject invention may be used for a variety of multiplexed analyses involving the action of one or more agents on a plurality of reagents comprising the mir and a target-binding region that undergoes a change as a result of a chemical reaction, resulting in a change in mobility of the product as compared to the starting material. The reaction may be the result of addition or deletion in relation to the target-binding region, so that the resulting product may be sequestered from the starting material. The subject systems find use in nucleic acid and protein analyses, reactions, particularly enzyme reactions, where one or more enzymes are acting on a group of different potential or actual substrates, and the like.

A system is provided for the simultaneous multiplexed determination of a plurality of events employing electrophoresis to distinguish the events, comprising an electrophoretic device for electrophoretic separation and detection, a container containing a first set of first agents, referred to as "e-tags," comprising differing mobility regions and a second reagent composition comprising at least one active second agent, under conditions where said second agent modifies at least one member of said first agent set resulting in a change of electrophoretic mobility of said at least one member to provide a modified member retaining said mobility region, and transfer of said at least one modified member to said electrophoretic device for separation and detection of said at least one modified member. The electrophoretic device may be connected to a data processor for receiving and processing data from the device, as well as operating the electrophoretic device.

The first set of first agents are considered to be "e-tag probes," and the modified members that retain the mobility region or mobility modifying region and are subjected to analysis are referred to as "e-tag reporters". In general, the e-tag probes comprise a mobility modifying region that is joined to a target binding region by a linker, which may include or be a reactive functionality, a cleavable linkage, a bond which may or may not be releasable or a group for joining to one or more of the other regions.

The systems are based on having libraries available comprising a plurality of e-tags that comprise at least a plurality of different mobility-identifying regions, so as to be separable by electrophoresis with the entities to which the mobility-identifying regions are attached. The mobility-identifying regions are retained in the product of the reaction, where the product is modified by the gain and/or loss of a group that changes the mass and may also change the charge of the product, as compared to the starting material. In some instances, the mobility-identifying region may be joined to a target-binding region by a cleavable bond, so that the mobility-identifying region is released for analysis subsequent to the modification of the target-binding region, e.g. complex formation.

In one aspect, the subject assays are predicated on having a reagent that has a high affinity for a reciprocal binding member, the analyte. Usually, the binding affinity will be at least about $10^{-7}M^{-1}$, more usually, at least about $10^{-8}M^{-1}$.

For the most part, the reagents will be receptors, which includes antibodies, IgA, IgD, IgG, IgE and IgM and subtypes thereof, enzymes, lectins, nucleic acids, nucleic acid binding proteins, or any other molecule that provides the desired specificity for the analyte in the assay. The antibodies may be polyclonal or monoclonal or mixtures of monoclonal antibodies depending on the nature of the target composition and the targets. The targets or analytes may be any molecule, such as small organic molecules of from about 100 to 2500 Da, poly(amino acids) including peptides of from about 3 to 100 amino acids and proteins of from about 100 to 50,000 or more amino acids, saccharides, lipids, nucleic acids, etc., where the analytes may be part of a larger assemblage, such as a cell, microsome, organelle, virus, protein complex, chromosome or fragment thereof, nucleosome, etc.

A. Electrophoretic Tags

An e-tag will be a molecule, which is labeled with a directly detectable label or can be made so by functionalization. The electrophoretic tags will be differentiated by their electrophoretic mobility, usually their mass/charge ratio, to provide different mobilities for each electrophoretic tag. Although in some instances the electrophoretic tags may have identical mass/charge ratios, such as oligonucleotides but differ in size or shape and therefore exhibit different electrophoretic mobilities under appropriate conditions. Therefore, the tags will be amenable to electrophoretic separation and detection, although other methods of differentiating the tags may also find use. The e-tag may be joined to any convenient site on the target binding reagent, without interfering with the synthesis, release and binding of the e-tag labeled reagent. For nucleotides, the e-tag may be bound to a site on the base, either an annular carbon atom or a hydroxyl or amino substituent.

In mass spectrometry, the E-TAGs may be different from the E-TAGs used in electrophoresis, since the E-TAGs do not require a label, nor a charge. Thus, these E-TAGs may be differentiated solely by mass, which can be a result of atoms of different elements, isotopes of such elements, and numbers of such atoms.

Electrophoretic tags are small molecules (molecular weight of 150 to 10,000), usually other than oligonucleotides, which can be used in any measurement technique that permits identification by mass, e.g. mass spectrometry, and or mass/charge ratio, as in mobility in electrophoresis. Simple variations in mass and/or mobility of the electrophoretic tag leads to generation of a library of electrophoretic tags, that can then be used to detect multiple snp's or multiple target sequences. The electrophoretic tags are easily and rapidly separated in free solution without the need for a polymeric separation media. Quantitation is achieved using internal controls. Enhanced separation of the electrophoretic tags in electrophoresis is achieved by modifying the tags with positively charged moieties.

The e-tags are a group of reagents having a mir that with the other regions to which the mir is attached during separation provide for unique identification of an entity of interest. The mir of the e-tags can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mir will have from 0 to 40, more usually from 0 to 30 heteroatoms, which in addition to the heteroatoms indicated above will include halogen or other heteroatom. The total number of atoms other than hydrogen will generally be fewer than 200 atoms, usually fewer than 100 atoms. Where acid groups are present, depending upon the pH of the medium in which the mir is present, various cations may be associated with the acid group. The acids may be organic or inorganic, including carboxyl, thionocarboxyl, thiocarboxyl, hydroxamic, phosphate, phosphite, phosphonate, sulfonate, sulfinate, boronic, nitric, nitrous, etc. For positive charges, substituents will include amino (includes ammonium), phosphonium, sulfonium, oxonium, etc., where substituents will generally be aliphatic of from about 1–6 carbon atoms, the total number of carbon atoms per heteroatom, usually be less than about 12, usually less than about 9. The mir may be neutral or charged depending on the other regions to which the mir is attached, at least one of the regions having at least one charge. Neutral mirs will generally be polymethylene, halo- or polyhaloalkylene or aralkylene (a combination of aromatic—includes heterocyclcic—and aliphatic groups), where halogen will generally be fluorine, chlorine, bromine or iodine, polyethers, particularly, polyoxyalkylene, wherein alkyl is of from 2–3 carbon atoms, polyesters, e.g. polyglycolide and polylactide, dendrimers, comprising ethers or thioethers, oligomers of addition and condensation monomers, e.g. acrylates, diacids and diols, etc. The side chains include amines, ammonium salts, hydroxyl groups, including phenolic groups, carboxyl groups, esters, amides, phosphates, heterocycles, particularly nitrogen heterocycles, such as the nucleoside bases and the amino acid side chains, such as imidazole and quinoline, thioethers, thiols, or other groups of interest to change the mobility of the e-tag. The mir may be a homooligomer or a heterooligomer, having different monomers of the same or different chemical characteristics, e.g., nucleotides and amino acids. Desirably neutral mass differentiating groups will be combined with short charged sequences to provide the mir.

The charged mirs will generally have only negative or positive charges, although, one may have a combination of charges, particularly where a region to which the mir is attached is charged and the mir has the opposite charge. The mirs may have a single monomer that provides the different functionalities for oligomerization and carry a charge or two monomers may be employed, generally two monomers. One may use substituted diols, where the substituents are charged and dibasic acids. Illustrative of such oligomers are the combination of diols or diamino, such as 2,3-dihydroxypropionic acid, 2,3-dihydroxysuccinic acid, 2,3-diaminosuccinic acid, 2,4-dihydroxyglutaric acid, etc. The diols or diamino compounds can be linked by dibasic acids, which dibasic acids include the inorganic dibasic acids indicated above, as well as dibasic acids, such as oxalic acid, malonic acid, succinic acid, maleic acid, furmaric acid, carbonic acid, etc. Instead of using esters, one may use amides, where amino acids or diamines and diacids may be employed. Alternatively, one may link the hydroxyls or amines with alkylene or arylene groups.

By employing monomers that have substituents that provide for charges or which may be modified to provide charges, one can provide for mirs having the desired mass/charge ratio. For example, by using serine or threonine, one may modify the hydroxyl groups with phosphate to provide negatively charged mirs. With arginine, lysine and histidine, one provides for positively charged mirs. Oligomerization may be performed in conventional ways to provide the appropriately sized mir. The different mirs having different orders of oligomers, generally having from 1 to 20 monomeric units, more usually about 1 to 12, where a unit intends a repetitive unit that may have from 1 to 2 different monomers. For the most part, oligomers will be used with other than nucleic acid target-binding regions. The polyfunctionality of the monomeric units provides for functionalities at the termini that may be used for conjugation to other moieties, so that one may use the available functionality for reaction to provide a different functionality. For example, one may react a carboxyl group with an aminoethylthiol, to replace the carboxyl group with a thiol functionality for reaction with an activated olefin.

By using monomers that have 1–3 charges, one may employ a low number of monomers and provide for mobility variation with changes in molecular weight. Of particular interest are polyolpolycarboxylic acids having from about two to four of each functionality, such as tartaric acid, 2,3-dihydroxyterephthalic acid, 3,4-dihydroxyphthalic acid, $\Delta^5$-tetrahydro-3,4-dihydroxyphthalic acid, etc. To provide for an additional negative charge, these monomers may be oligomerized with a dibasic acid, such as a phosphoric acid derivative to form the phosphate diester. Alternatively, the carboxylic acids could be used with a diamine to form a polyamide, while the hydroxyl groups could be used to form esters, such as phosphate esters, or ethers such as the ether of glycolic acid, etc. To vary the mobility, various aliphatic groups of differing molecular weight may be employed, such as polymethylenes, polyoxyalkylenes, polyhaloaliphatic or -aromatic groups, polyols, e.g. sugars, where the mobility will differ by at least about 0.01, more usually at least about 0.02 and more usually at least about 0.5. Alternatively, the libraries may include oligopeptides for providing the charge, particularly oligopeptides of from 2–6, usually 2–4 monomers, either positive charges resulting from lysine, arginine and histidine or negative charges, resulting from aspartic and glutamic acid. Of course, one need not use naturally occurring amino acids, but unnatural or synthetic amino acids, such as taurine, phosphate substituted serine or threonine, S-α-succinylcysteine, co-oligomers of diamines and amino acids, etc.

Where the e-tags are used for mass detection, as with mass spectrometry, the e-tags need not be charged but merely differ in mass, since a charge will be imparted to the e-tag reporter by the mass spectrometer. Thus, one could use the same or similar monomers, where the functionalities would be neutral or made neutral, such as esters and amides of carboxylic acids. Also, one may vary the e-tags by isotopic substitution, such as $^2$H, $^{18}$O, $^{14}$C, etc.

The e-tag may be linked by a stable bond or one, which may be cleavable, thermally, photolytically or chemically. There is an interest in cleaving the e-tag from the target-binding region in situations where cleavage of the target-binding region results in significant cleavage at other than the desired site of cleavage, resulting in satellite cleavage products, such as di- and higher oligonucleotides and this family of products interferes with the separation and detection of the e-tags. However, rather than requiring an additional step in the identification of the tags by releasing them from the base to which they are attached, one can modify the target binding sequence to minimize obtaining cleavage at other than the desired bond, for example, the ultimate or penultimate phosphate link in a nucleic acid sequence. For immunoassays involving specific binding members, bonding of the e-tag will usually be through a cleavable bond to a convenient functionality, such as carboxy, hydroxy, amino or thiol, particularly as associated with proteins, lipids and saccharides.

If present, the nature of the releasable or cleavable link may be varied widely. Numerous linkages are available, which are thermally, photolytically or chemically labile. See, for example, U.S. Pat. No. 5,721,099. Where detachment of the product from all or a portion of the target-binding region is desired, there are numerous functionalities and reactants, which may be used. Conveniently, ethers may be used, where substituted benzyl ether or derivatives thereof, e.g. benzhydryl ether, indanyl ether, etc. may be cleaved by acidic or mild reductive conditions. Alternatively, one may employ beta-elimination, where a mild base may serve to release the product. Acetals, including the thio analogs thereof, may be employed, where mild acid, particularly in the presence of a capturing carbonyl compound, may serve. By combining formaldehyde, HCl and an alcohol moiety, an α-chloroether is formed. This may then be coupled with an hydroxy functionality to form the acetal. Various photolabile linkages may be employed, such as o-nitrobenzyl, 7-nitroindanyl, 2-nitrobenzhydryl ethers or esters, etc.

For a list of cleavable linkages, see, for example, Greene and Wuts, Protective Groups in Organic Synthesis, $2^{nd}$ ed. Wiley, 1991. The versatility of the various systems that have been developed allows for broad variation in the conditions for attachment of the e-tag entities.

Various functionalities for cleavage are illustrated by: silyl groups being cleaved with fluoride, oxidation, acid, bromine or chlorine; o-nitrobenzyl with light; catechols with cerium salts; olefins with ozone, permanganate or osmium tetroxide; sulfides with singlet oxygen or enzyme catalyzed oxidative cleavage with hydrogen peroxide, where the resulting sulfone can undergo elimination; furans with oxygen or bromine in methanol; tertiary alcohols with acid; ketals and acetals with acid; α- and β-substituted ethers and esters with base, where the substituent is an electron withdrawing group, e.g., sulfone, sulfoxide, ketone, etc., and the like.

In one embodiment, the electrophoretic tags will have a linker, which provides the linkage between the base and the detectable label molecule, usually a fluorescer, or a functionality which may be used for linking to a detectable label molecule. By having different functionalities, which may be individually bonded to a detectable label molecule, one enhances the opportunity for diversity of the electrophoretic tags. Using different fluorescers for joining to the different functionalities, the different fluorescers can provide differences in light emission and mass/charge ratios for the electrophoretic tags.

For the most part, the linker may be a bond, where the label is directly bonded to the nucleoside, or a link of from 1 to 500 or more, usually 1 to 300 atoms, more usually 2 to 100 atoms in the chain. The total number of atoms in the chain will depend to a substantial degree on the diversity required to recognize all the snp's to be determined. The chain of the linker for the most part will be comprised of carbon, nitrogen, oxygen, phosphorous, boron, and sulfur. Various substituents may be present on the linker, which may be naturally present as part of the naturally occurring monomer or introduced by synthesis. Functionalities which may be present in the chain include amides, phosphate esters, ethers, esters, thioethers, disulfides, borate esters, sulfate esters, etc. The side chains include amines, ammonium salts, hydroxyl groups, including phenolic groups, carboxyl groups, esters, amides, phosphates, heterocycles, particularly nitrogen heterocycles, such as the nucleoside bases and the amino acid side chains, such as imidazole and quinoline, thioethers, thiols, or other groups of interest to change the mobility of the electrophoretic tag. The linker may be a homooligomer or a heterooligomer, having different monomers of the same or different chemical characteristics, e.g., nucleotides and amino acids.

The linker or mir may be joined in any convenient manner to a unit of the target-binding region, such as the base of the nucleoside or the amino acid of a protein. Various functionalities which may be used include alkylamine, amidine, thioamide, ether, urea, thiourea, guanidine, azo, thioether and carboxylate, sulfonate, and phosphate esters, amides and thioesters.

The linkers may be oligomers, where the monomers may differ as to mass and charge. For convenience and economy, monomers will generally be commercially available, but if desired, they may be originally synthesized. Monomers which are commercially available and readily lend themselves to oligomerization include amino acids, both natural and synthetic, nucleotides, both natural and synthetic, and monosaccharides, both natural and synthetic, while other monomers include hydroxyacids, where the acids may be organic or inorganic, e.g. carboxylic, phosphoric, boric, sulfonic, etc., and amino acids, where the acid is inorganic, and the like. In some instances, nucleotides, natural or synthetic, may find use. The monomers may be neutral, negatively charged or positively charged. Normally, the charges of the monomers in the linkers will be the same, so that in referring to the mass/charge ratio, it will be related to the same charge. Where the label has a different charge from the linker or mir, this will be treated as if the number of charges are reduced by the number of charges on the linker or mir. For natural amino acids, the positive charges may be obtained from lysine, arginine and histidine, while the negative charges may be obtained from aspartic and glutamic acid. For nucleotides, the charges will be obtained from the phosphate and any substituents that may be present or introduced onto the base. For sugars sialic acid, uronic acids of the various sugars, or substituted sugars may be employed.

It will be understood that the mir or mobility/mass identifying region, also referred to herein as "L", $M^*$, $C^*$, the mobility identifying region, the mobility region, the mobility modifying region, the mobility modifier or $M_j$ is the component of an e-tag or e-tag reporter which has a known charge/mass ratio and imparts a known and unique electrophoretic mobility to an e-tag reporter comprising the mir or mobility modifier.

The linker L may include charged groups, uncharged polar groups or be non-polar. The groups may be alkylene and substituted alkylenes, oxyalkylene and polyoxyalkylene, particularly alkylene of from 2 to 3 carbon atoms, arylenes and substituted arylenes, polyamides, polyethers, polyalkylene amines, etc. Substituents may include heteroatoms, such as halo, phosphorous, nitrogen, oxygen, sulfur, etc., where the substituent may be halo, nitro, cyano, non-oxo-carbonyl, e.g. ester, acid and amide, oxo-carbonyl, e.g. aldehyde and keto, amidine, urea, urethane, guanidine, carbamyl, amino and substituted amino, particularly alkyl substituted amino, azo, oxy, e.g. hydroxyl and ether, etc., where the substituents will generally be of from about 0 to 10 carbon atoms, while L will generally be of from about 1 to 100 carbon atoms, more usually of from about 1 to 60 carbon atoms and preferably about 1 to 36 carbon atoms. L will be joined to the label and the target-binding region by any convenient functionality, such as carboxy, amino, oxy, phospho, thio, iminoether, etc., where in many cases the label and the target-binding region will have a convenient functionality for linkage.

The number of heteroatoms in L is sufficient to impart the desired charge to the label conjugate, usually from about 1 to about 200, more usually from about 2 to 100, heteroatoms. The heteroatoms in L may be substituted with atoms other than hydrogen.

The charge-imparting moieties of L may be, for example, amino acids, tetraalkylammonium, phosphonium, phosphate diesters, carboxylic acids, thioacids, sulfonic acids, sulfate groups, phosphate monoesters, and the like and combinations of one or more of the above. The number of the above components of L is such as to achieve the desired number of different charge-imparting moieties. The amino acids may be, for example, lysine, aspartic acid, alanine, gamma-aminobutyric acid, glycine, β-alanine, cysteine, glutamic acid, homocysteine, β-alanine and the like. The phosphate diesters include, for example, dimethyl phosphate diester, ethylene glycol linked phosphate diester, and so forth. The thioacids include, by way of example, thioacetic acid, thiopropionic acid, thiobutyric acid and so forth. The carboxylic acids preferably have from 1 to 30 carbon atoms, more preferably, from 2 to 15 carbon atoms and preferably comprise one or more heteroatoms and may be, for example, acetic acid derivatives, formic acid derivatives, succinic acid derivatives, citric acid derivatives, phytic acid derivatives and the like.

Of particular interest for L is to have two sub-regions, a common charged sub-region, which will be common to a group of e-tags, and a varying uncharged, a non-polar or polar sub-region, that will vary the mass/charge ratio. This permits ease of synthesis, provides for relatively common chemical and physical properties and permits ease of handling. For negative charges, one may use dibasic acids that are substituted with functionalities that permit low orders of oligomerization, such as hydroxy and amino, where amino will usually be present as neutral amide. These charge-imparting groups provide aqueous solubility and allow for various levels of hydrophobicity in the other sub-region. Thus the uncharged sub-region could employ substituted dihydroxybenzenes, diaminobenzenes, or aminophenols, with one or greater number of aromatic rings, fused or non-fused, where substituents may be halo, nitro, cyano, alkyl, etc., allowing for great variation in molecular weight by using a common building block. Where the other regions of the e-tag impart charge to the e-tag, L may be neutral.

In one preferred embodiment of the present invention, the charge-imparting moiety is conveniently composed primarily of amino acids but also may include thioacids and other carboxylic acids having from one to five carbon atoms. The charge imparting moiety may have from 1 to 30, preferably 1 to 20, more preferably, 1 to 10 amino acids per moiety and may also comprise 1 to 3 thioacids or other carboxylic acids. However, when used with an uncharged sub-region, the charged sub-region will generally have from 1–4, frequently 1–3 amino acids. As mentioned above, any amino acid, both naturally occurring and synthetic, may be employed.

The e-tag for use in electrophoresis may be represented by the formula:

R-L-T wherein R is a label, particularly a fluorescer, L is a mir, a bond or a linking group where L and the regions to which L is attached provide for the variation in mobility of the e-tags. T comprises a portion of the target-binding region, particularly a nucleoside base, purine or pyrimidine, and is the base, a nucleoside, nucleotide or nucleotide triphosphate, an amino acid, either naturally occurring or synthetic, or other functionality that may serve to participate in the synthesis of an oligomer, when T is retained, and is otherwise a functionality resulting from the cleavage between L, the mir, and the target-binding region. L provides a major factor in the differences in mobility between the different e-tags, in combination with the label and any residual entity, which remain with the mir. L may or may not include a cleavable linker, depending upon whether the terminal entity to which L is attached is to be retained or completely removed.

In one representation of the invention, L has been substantially described as the mir and as indicated previously may include charged groups, uncharged polar groups or be non-polar. The groups may be alkylene and substituted alkylenes, oxyalkylene and polyoxyalkylene, particularly alkylene of from 2 to 3 carbon atoms, arylenes and substituted arylenes, polyamides, polyethers, polyalkylene amines, etc. Substituents may include heteroatoms, such as halo, phosphorous, nitrogen, oxygen, sulfur, etc., where the substituent may be halo, nitro, cyano, non-oxo-carbonyl, e.g. ester, acid and amide, oxo-carbonyl, e.g. aldehyde and keto, amidine, urea, urethane, guanidine, carbamyl, amino and substituted amino, particularly alkyl substituted amino, azo, oxy, e.g. hydroxyl and ether, etc., where the substituents will generally be of from about 0 to 10 carbon atoms, while L will generally be of from about 1 to 100 carbon atoms, more usually of from about 1 to 60 carbon atoms and preferably about 1 to 36 carbon atoms. L will be joined to the label and the target-binding region by any convenient functionality, such as carboxy, amino, oxy, phospo, thio, iminoether, etc., where in many cases the label and the target-binding region will have a convenient functionality for linkage.

The number of heteroatoms in L is sufficient to impart the desired charge to the label conjugate, usually from about 1 to about 200, more usually from about 2 to 100, heteroatoms. The heteroatoms in L may be substituted with atoms other than hydrogen.

In one embodiment of the present invention the label conjugates having different charge to mass ratios may comprise fluorescent compounds, each of which are linked to molecules that impart a charge to the fluorescent compound conjugate. As indicated previously, desirably the linking group has an overall negative charge, preferably having in the case of a plurality of groups, groups of the same charge, where the total charge may be reduced by having one or more oppositely charged moiety.

Of particular interest for L is to have two sub-regions, a common charged sub-region, which will be common to a group of e-tags, and a varying uncharged, a non-polar or polar sub-region, that will vary the mass/charge ratio. This permits ease of synthesis, provides for relatively common chemical and physical properties and permits ease of handling. For negative charges, one may use dibasic acids that are substituted with functionalities that permit low orders of oligomerization, such as hydroxy and amino, where amino will usually be present as neutral amide. These charge imparting groups provide aqueous solubility and allow for various levels of hydrophobicity in the other sub-region. Thus the uncharged sub-region could employ substituted dihydroxybenzenes, diaminobenzenes, or aminophenols, with one or greater number of aromatic rings, fused or non-fused, where substituents may be halo, nitro, cyano, alkyl, etc., allowing for great variation in molecular weight by using a common building block. Where the other regions of the e-tag impart charge to the e-tag, L may be neutral.

In some instances, where release of the e-tag results in an available functionality that can be used to react with a detectable label, there will be no need for R to be a functionality. The release of the e-tag can provide an hydroxyl, amino, carboxy or thiol group, where each may serve as the site for conjugation to the detectable label. To the extent that the e-tag is released free of a component of the target-binding region, this opportunity will be present. In that case, R is the unreactive (under the conditions of the conjugation) terminus of L and T is a functionality for release of the e-tag that may be joined to all or a portion of the target-binding region or may be available for binding to all or a portion of the target-binding region.

Conjugates of particular interest comprise a fluorescent compound and a different amino acid or combinations thereof in the form of a peptide or combinations of amino acids and thioacids or other carboxylic acids. Such compounds are represented by the formula:

R'-L'-T' wherein R' is a flourescer, L' is an amino acid or a peptide or combinations of amino acids and thioacids or other carboxylic acids and T' is a functionality for linking to a nucleoside base or is a nucleoside, nucleotide triphosphate.

In a particular embodiment the label conjugates may be represented by the formula:

Fluorescer-L"-(amino acid)$_n$-T"

wherein L" is a bond or a linking group of from 1 to 20 atoms other than hydrogen, n is 1 to 20, and T'" comprises a nucleoside base, purine or pyrimidine, including a base, a nucleoside, a nucleotide or nucleotide triphosphates, an amino acid, or functionality for linking to the target-binding region. An example of label conjugates in this embodiment, by way of illustration and not limitation, is one of which the fluorescer is fluorescein, L" is a bond in the form of an amide linkage involving the meta-carboxyl of the fluorescein and the terminal amine group of lysine, and T" is a nucleotide triphosphate. These label conjugates may be represented as follows:

Flourescein-(CO)NH—CH(CH$_2$)$_3$CH(NH$_2$)(amino acid)$_n$COX" wherein X is as set forth in Table 1.

TABLE 1

| No. | X | Charge |
|---|---|---|
| 1 | OH | −2 |
| 2 | NH-lysine | −1 |
| 3 | NH-(lysine)$_2$ | neutral |
| 4 | NH-alanine | −3 |
| 5 | NH-aspartic acid | −4 |
| 6 | NH-(aspartic acid)$_2$ | −5 |
| 7 | NH-(aspartic acid)$_3$ | −6 |
| 8 | NH-(aspartic acid)$_4$ | −7 |
| 9 | NH-(aspartic acid)$_5$ | −8 |
| 10 | NH-(aspartic acid)$_6$ | −9 |
| 11 | NH-(aspartic acid)$_7$ | −10 |
| 12 | NH-alanine-lysine | −2 (unique q/M) |
| 13 | NH-aspartic acid-lysine | −3 (unique q/M) |
| 14 | NH-(aspartic acid)$_2$-lysine | −4 (unique q/M) |
| 15 | NH-(aspartic acid)$_3$-lysine | −5 (unique q/M) |
| 16 | NH-(aspartic acid)$_4$-lysine | −6 (unique q/M) |
| 17 | NH-(aspartic acid)$_5$-lysine | −7 (unique q/M) |
| 18 | NH-(aspartic acid)$_6$-lysine | −8 (unique q/M) |
| 19 | NH-(aspartic acid)$_7$-lysine | −9 (unique q/M) |
| 20 | NH-(aspartic acid)$_8$-lysine | −10 (unique q/M) |
| 21 | NH-(lysine)$_4$ | + |
| 22 | NH-(lysine)$_5$ | +2 | wherein q is charge, M is mass and mobility is $q/M^{2/3}$. Examples of such label conjugates are shown in FIG. 1C. Table 2 shows various characteristics for the label conjugates.

TABLE 2

Various Characteristics For The Label Conjugates

| No. | Mass(M) | Charge(q) | $M^{2/3}$ | $q/M^{2/3}$ | Mobility |
|---|---|---|---|---|---|
| 1 | 744.82 | 0 | 82.16765 | 0 | 0 |
| 2 | 877.02 | 0 | 91.62336 | 0 | 0 |
| 3 | 828.71 | −1 | 88.22704 | −0.01133 | −0.16546 |
| 4 | 970.71 | −1 | 98.03767 | −0.0102 | −0.1489 |
| 5 | 700.82 | −2 | 78.89891 | −0.02535 | −0.37004 |
| 6 | 842.83 | −2 | 89.22639 | −0.2241 | −0.32721 |
| 7 | 815.92 | −3 | 87.31692 | −0.03436 | −0.50155 |
| 8 | 957.92 | −3 | 97.17461 | −0.03087 | −0.45067 |
| 9 | 931.02 | −4 | 95.34677 | −0.04195 | −0.61242 |
| 10 | 1073.02 | −4 | 104.8106 | −0.03816 | −0.55712 |
| 11 | 1046 | −5 | 103.0436 | −0.04852 | −0.70834 |
| 12 | 1188 | −5 | 112.1702 | −0.04458 | −0.65071 |
| 13 | 1161 | −6 | 110.4642 | −0.05432 | −0.79291 |
| 14 | 1303 | −6 | 119.297 | −0.05029 | −0.7342 |
| 15 | 1276 | −7 | 117.6433 | −0.0595 | −0.86861 |
| 16 | 1418 | −7 | 126.2169 | −0.05546 | −0.80961 |
| 17 | 1391 | −8 | 124.6096 | −0.0642 | −0.9372 |
| 18 | 1533 | −8 | 132.952 | −0.06017 | −0.87839 |
| 19 | 1506 | −9 | 131.3863 | −0.0685 | −0.99997 |
| 20 | 1648 | −9 | 139.6205 | −0.06451 | −0.94167 |
| 21 | 793.52 | 1 | 85.7114 | 0.011667 | 0.170316 |
| 22 | 935.52 | 1 | 95.65376 | 0.010454 | 0.152613 |

Another group of e-tags has a mir which is dependent on using an alkylene or aralkylene (comprising a divalent aliphatic group having 1–2 aliphatic regions and 1–2 aromatic regions, generally benzene), where the groups may be substituted or unsubstituted, usually unsubstituted, of from 2–16, more usually 2–12, carbon atoms, where the mir may link the same or different fluorescers to a monomeric unit, e.g. a nucleotide. The mir may terminate in a carboxy, hydroxy or amino group, being present as an ester or amide. By varying the substituents on the fluorophor, one can vary the mass in units of at least 5 or more, usually at least about 9, so as to be able to obtain satisfactory separation in capillary electrophoresis. To provide further variation, a thiosuccinimide group may be employed to join alkylene or aralkylene groups at the nitrogen and sulfur, so that the total number of carbon atoms may be in the range of about 2–30, more usually 2–20. Instead of or in combination with the above groups and to add hydrophilicity, one may use alkyleneoxy groups.

Besides the nature of the mir, as already indicated, diversity can be achieved by the chemical characteristics of the label, the use of energy transfer complexes, variation in the chemical nature of the mir, which affects mobility, such as folding, interaction with the solvent and ions in the solvent, and the like. In one embodiment of the invention, the mir will usually be an oligomer, where the mir may be synthesized on a support or produced by cloning or expression in an appropriate host. Conveniently, polypeptides can be produced where there is the only one or serine/threonine/tyrosine, aspartic/glutamic acid, or lysine/arginine/histidine, other than an end group, so that there is a unique functionality, which may be differentially functionalized. By using protective groups, one can distinguish a side chain functionally from a terminal amino acid functionality. Also, by appropriate design, one may provide for preferential reaction between the same functionalities present at different sites on the mir. Whether one uses synthesis or cloning for preparation of oligopeptides, will to a substantial degree depend on the length of the mir.

Figure 2:
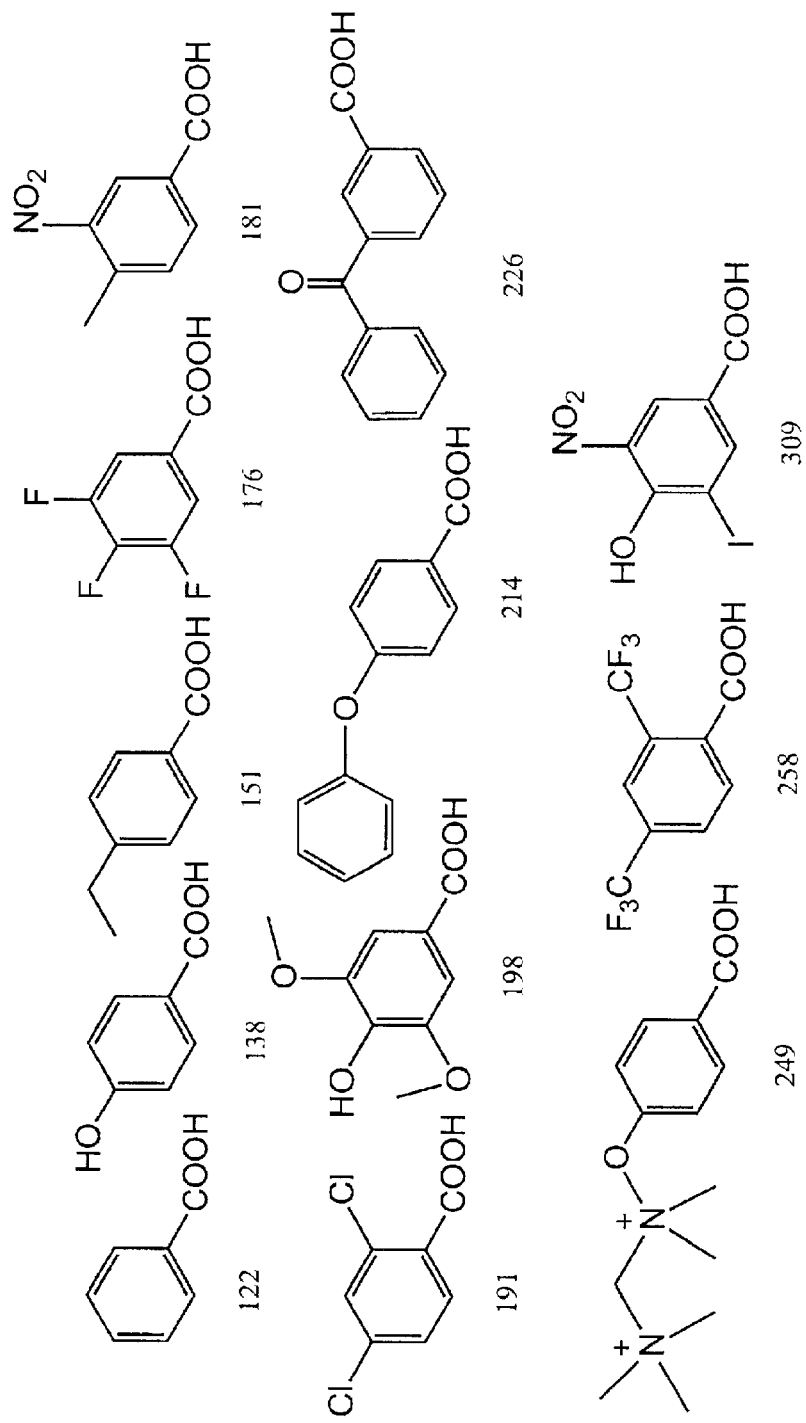
FIG. 2 shows the structure of several benzoic acid derivatives that can serve as mobility modifiers.

Substituted aryl groups can serve as both mass- and charge-modifying regions (FIG. 2). Various functionalities may be substituted onto the aromatic group, e.g. phenyl, to provide mass as well as charges to the e-tag reporter. The aryl group may be a terminal group, where only one linking functionality is required, so that a free hydroxyl group may be acylated, may be attached as a side chain to an hydroxyl present on the e-tag reporter chain, or may have two functionalities, e.g. phenolic hydroxyls, that may serve for phophite ester formation and other substituents, such as halo, haloalkyl, nitro, cyano, alkoxycarbonyl, alkylthio, etc. where the groups may be charged or uncharged.

The label conjugates may be prepared utilizing conjugating techniques that are well known in the art. The charge-imparting moiety L may be synthesized from smaller molecules that have functional groups that provide for linking of the molecules to one another, usually in a linear chain. Such functional groups include carboxylic acids, amines, and hydroxy- or thiol-groups. In accordance with the present invention the charge-imparting moiety may have one or more side groups pending from the core chain. The side groups have a functionality to provide for linking to a label or to another molecule of the charge-imparting moiety.

Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g. sulfonate, phosphate esters, sulfonamides, thioesters, etc., and the like.

The electrophoretic tags comprise a linker, which provides the linkage between the base and the fluorescent molecule or a functionality which may be used for linking to a fluorescent molecule. By having different functionalities that may be individually bonded to a detectable label, one enhances the opportunity for diversity of the e-tags. Using different fluorescers for joining to the different functionalities, the different fluorescers can provide differences in light emission and mass/charge ratios for the e-tags.

B. Electrophoretic Tags for use in Electrophoresis

The electrophoretic tag, which is detected, will comprise the mir, generally a label, and optionally a portion of the target-binding region, all of the target-binding region when the target is an enzyme and the target-binding region is the substrate. Generally, the electrophoretic tag will have a charge/mass ratio in the range of about −0.0001 to 0.1, usually in the range of about −0.001 to about 0.5. Mobility is $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more.

In those instances where a label is not present on the e-tag bound to the target-binding moiety (e.g., a snp detection sequence), the mixture may be added to a functionalized fluorescent tag to label the e-tag with a fluorescer. For example, where a thiol group is present, the fluorescer could have an activated ethylene, such as maleic acid to form the thioether. For hydroxyl groups, one could use activated halogen or pseudohalogen for forming an ether, such as an α-haloketone. For carboxyl groups, carbodiimide and appropriate amines or alcohols would form amides and esters, respectively. For an amine, one could use activated carboxylic acids, aldehydes under reducing conditions, activated halogen or pseudohalogen, etc. When synthesizing oligopeptides, protective groups are used. These could be retained while the fluorescent moiety is attached to an available functionality on the oligopeptide.

C. Capture Ligands

Other reagents that are useful include a ligand-modified nucleotide and its receptor. Ligands and receptors include biotin and strept/avidin, ligand and antiligand, e.g. digoxin or derivative thereof and antidigoxin, etc. By having a ligand conjugated to the oligonucleotide, one can sequester the eTag conjugated oligonucleotide probe and its target with the receptor, remove unhybridized eTag reporter conjugated oligonucleotide and then release the bound eTag reporters or bind an oppositely charged receptor, so that the ligand-receptor complex with the eTag reporter migrates in the opposite direction.

In one exemplary use of capture ligands, a snp detection sequence may be further modified to improve separation and detection of the released e-tags. By virtue of the difference in mobility of the e-tags, the snp detection sequences will also have different mobilities. Furthermore, these molecules will be present in much larger amounts than the released e-tags, so that they may obscure detection of the released e-tags. Also, it is desirable to have negatively charged snp detection sequence molecules, since they provide for higher enzymatic activity and decrease capillary wall interaction. Therefore, by providing that the intact snp detection sequence molecule can be modified with a positively charged moiety, but not the released e-tag, one can change the electrostatic nature of the snp detection sequence molecules during the separation. By providing for a capture ligand on the snp detection sequence molecule to which a positively charged molecule can bind, one need only add the positively charged molecule to change the electrostatic nature of the snp detection sequence molecule. Conveniently, one will usually have a ligand of under about 1 kDa. This may be exemplified by the use of biotin as the ligand and avidin, which is highly positively charged, as the receptor (capture agent)/positively charged molecule. Instead of biotin/avidin, one may have other pairs, where the receptor, e.g. antibody, is naturally positively charged or is made so by conjugation with one or more positively charged entities, such as arginine, lysine or histidine, ammonium, etc. The presence of the positively charged moiety has many advantages in substantially removing the snp detection sequence molecules.

If desired, the receptor may be used to physically sequester the molecules to which it binds, removing entirely intact e-tags containing the target-binding region or modified target-binding regions retaining the ligand. These modified target-binding regions may be as a result of degradation of the starting material, contaminants during the preparation, aberrant cleavage, etc. or other nonspecific degradation products of the target binding sequence. As above, a ligand, exemplified by biotin, is attached to the target-binding region, e.g. the penultimate nucleoside, so as to be separated from the e-tag upon cleavage.

After a 5' nuclease assay, a receptor for the ligand, for biotin exemplified by strept/avidin (hereafter "avidin") is added to the assay mixture (Example 10). Other receptors include natural or synthetic receptors, such as immunoglobulins, lectins, enzymes, etc. Desirably, the receptor is positively charged, naturally as in the case of avidin, or is made so, by the addition of a positively charged moiety or moieties, such as ammonium groups, basic amino acids, etc. Avidin binds to the biotin attached to the detection probe and its degradation products. Avidin is positively charged, while the cleaved electrophoretic tag is negatively charged. Thus the separation of the cleaved electrophoretic tag from, not only uncleaved probe, but also its degradation products, is easily achieved by using conventional separation methods. Alternatively, the receptor may be bound to a solid support or high molecular weight macromolecule, such as a vessel wall, particles, e.g. magnetic particles, cellulose, agarose, etc., and separated by physical separation or centrifugation, dialysis, etc. This method further enhances the specificity of the assay and allows for a higher degree of multiplexing.

As a general matter, one may have two ligands, if the nature of the target-binding moiety permits. As described above, one ligand can be used for sequestering e-tags bound to the target-binding region, retaining the first ligand from products lacking the first ligand. Isolation and concentration of the e-tags bound to a modified target-binding region lacking the first ligand would then be performed. In using the two ligands, one would first combine the reaction mixture with a first receptor for the first ligand for removing target-binding region retaining the first ligand. One could either separate the first receptor from the composition or the first receptor would be retained in the composition, as described. This would be followed by combining the resulting composition, where the target-binding region containing the first ligand is bound to the first receptor, with the second receptor, which would serve to isolate or enrich for modified target-binding region lacking the first ligand, but retaining the second ligand. The second ligand could be the detectable label; a small molecule for which a receptor is available, e.g. a hapten, or a portion of the e-tag could serve as the second ligand. After the product is isolated or enriched, the e-tag could be released by denaturation of the receptor, displacement of the product, high salt concentrations and/or organic solvents, etc.

For e-tags associated with nucleic acid sequences, improvements include employing a blocking linkage between nucleotides in the sequence, particularly at least one of the links between the second to fourth nucleotides to inhibit cleavage at this or subsequent sites, and using control sequences for quantitation. Further improvements in the e-tags provide for having a positively multicharged moiety joined to the e-tag probe during separation.

While the ligand may be present at a position other than the penultimate position and one may make the ultimate linkage nuclease resistant, so that cleavage is directed to the penultimate linkage, this will not be as efficient as having cleavage at the ultimate linkage.

Figure 3A:
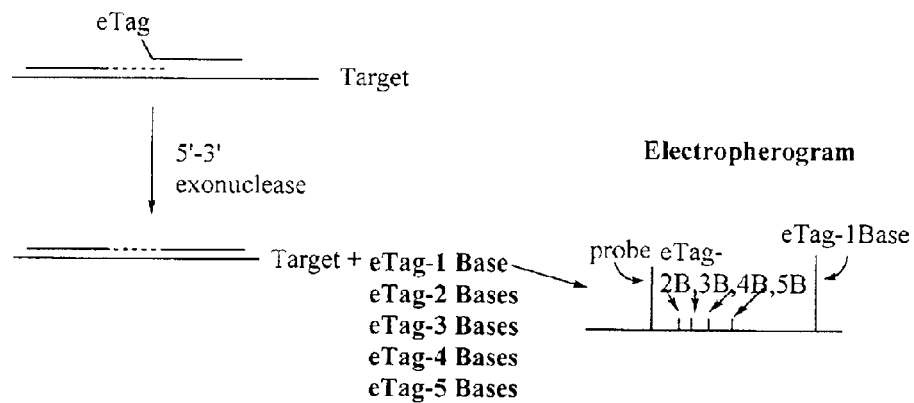
FIGS. 3A–D provide a schematic illustration of the generalized methods of the invention employing a nucleotide target and a 5' exonuclease indicating that only one eTag is generated per target for maximum multiplexing capabilities (A); the use of a capture ligand, biotin, to facilitate the removal of uncleaved or partially cleaved e-tag probe from the reaction mixture (B) and (C); and the use of nuclease resistant modifications (e.g., phosphorothioates) to the backbone of the target binding region (D).
Figure 3B:
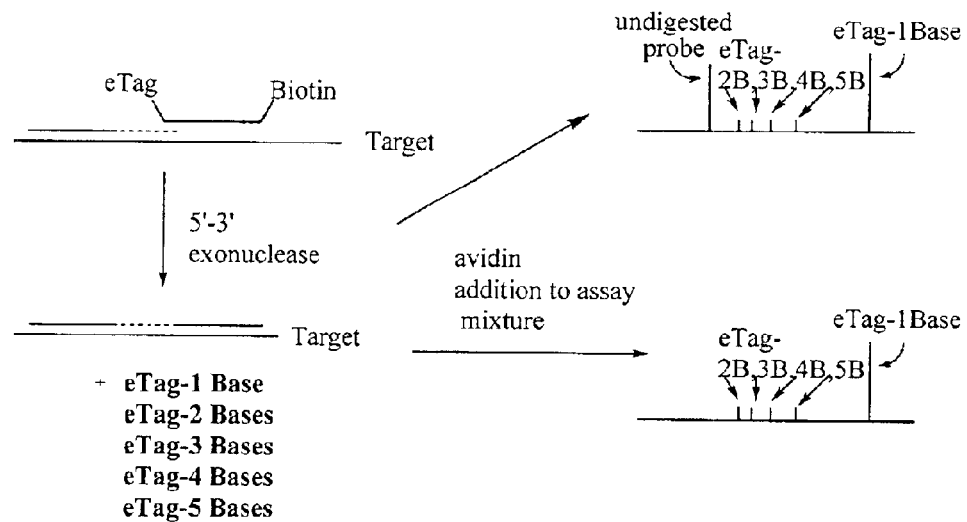
Figure 3C:
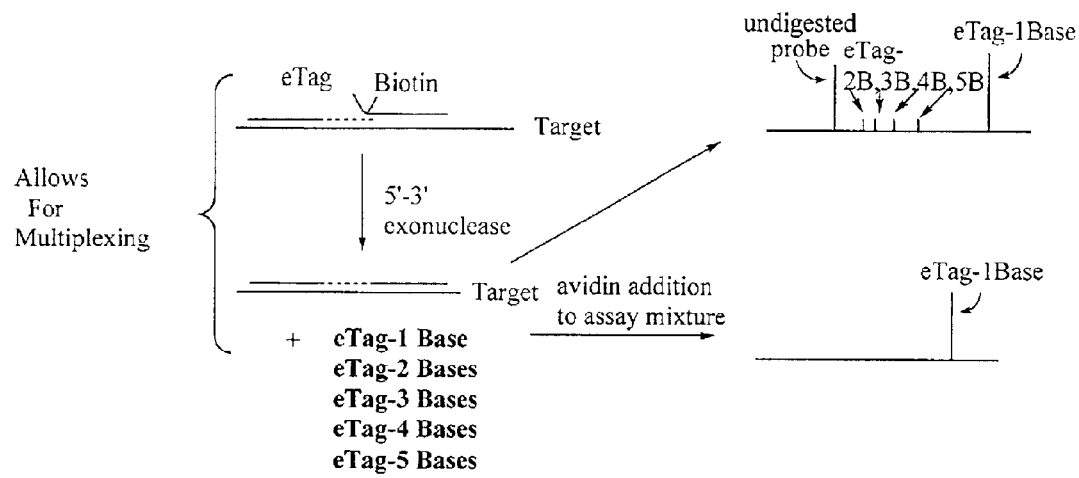
Figure 3D:
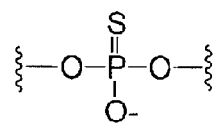

The above are generally applicable not only to generating a single e-tag per sequence detected, but also to generation of a single oligonucleotide fragment for fragment separation and identification by electrophoresis or by mass spectra, as it is essential to get one fragment per sequence detected. For purpose of explanation, these methods are illustrated below. FIGS. 3A–C provide a schematic illustration of the generalized methods of the invention employing a nucleotide target and a 5' exonuclease indicating that only one eTag is generated per target for maximum multiplexing capabilities.

D. E-tag Reagents—Synthesis

The chemistry for performing the types of syntheses to form the charge-imparting moiety or mobility modifier as a peptide chain is well known in the art. See, for example, Marglin, et al., *Ann. Rev. Biochem.* (1970) 39:841–866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, *J. Am. Chem. Soc.* (1980) 85:2149–2154 and Houghten et al., *Int. J. Pep. Prot. Res.* (1980) 16:311–320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (1969); and J. Meienhofer," Hormonal Proteins and Peptides", (1973), vol. 2, p 46, Academic Press (New York), for solid phase peptide synthesis; and E. Schroder, et al., "The Peptides, vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

In one exemplary approach, after the synthesis of the peptide is complete, the peptide is removed from the resin by conventional means such as ammonolysis, acidolysis and the like. The fully deprotected peptide may then be purified by techniques known in the art such as chromatography, for example, adsorption chromatography, ion exchange chromatography, partition chromatography, high performance liquid chromatography, thin layer chromatography, and so forth.

As can be seen, the selected peptide representing a charge-imparting moiety may be synthesized separately and then attached to the label either directly or by means of a linking group. On the other hand, the peptide may be synthesized as a growing chain on the label. In any of the above approaches, the linking of the peptide or amino acid to the label may be carried out using one or more of the techniques described above for the synthesis of peptides or for linking moieties to labels.

Synthesis of e-tags comprising nucleotides can be easily and effectively achieved via assembly on a solid phase support during probe synthesis, using standard phosphoramidite chemistries. The e-tags are assembled at the 5 end of probes after coupling of a final nucleosidic residue, which becomes part of the e-tag during the assay.

Figure 4:
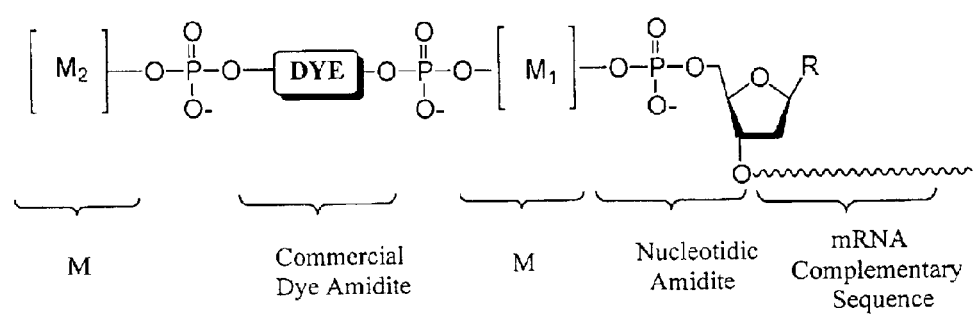
FIG. 4 illustrates the design and synthesis of e-tags using a LabCard (Detection: 4.7 cm; 200 V/cm) and standard phosphoramidite coupling chemistry.

In one approach, the e-tag probe is constructed sequentially from a single or several monomeric phosphoramidite building blocks (one containing a dye residue), which are chosen to generate tags with unique electrophoretic mobilities based on their mass to charge ratio. The e-tag probe is thus composed of monomeric units of variable charge to mass ratios bridged by phosphate linkers. FIG. 4 illustrates the design and synthesis of e-tags using a LabCard (Detection: 4.7 cm; 200 V/cm) and standard phosphoramidite coupling chemistry.). The separation of e-tags on a LabCard (FIG. 5) has been demonstrated.

Figure 7:
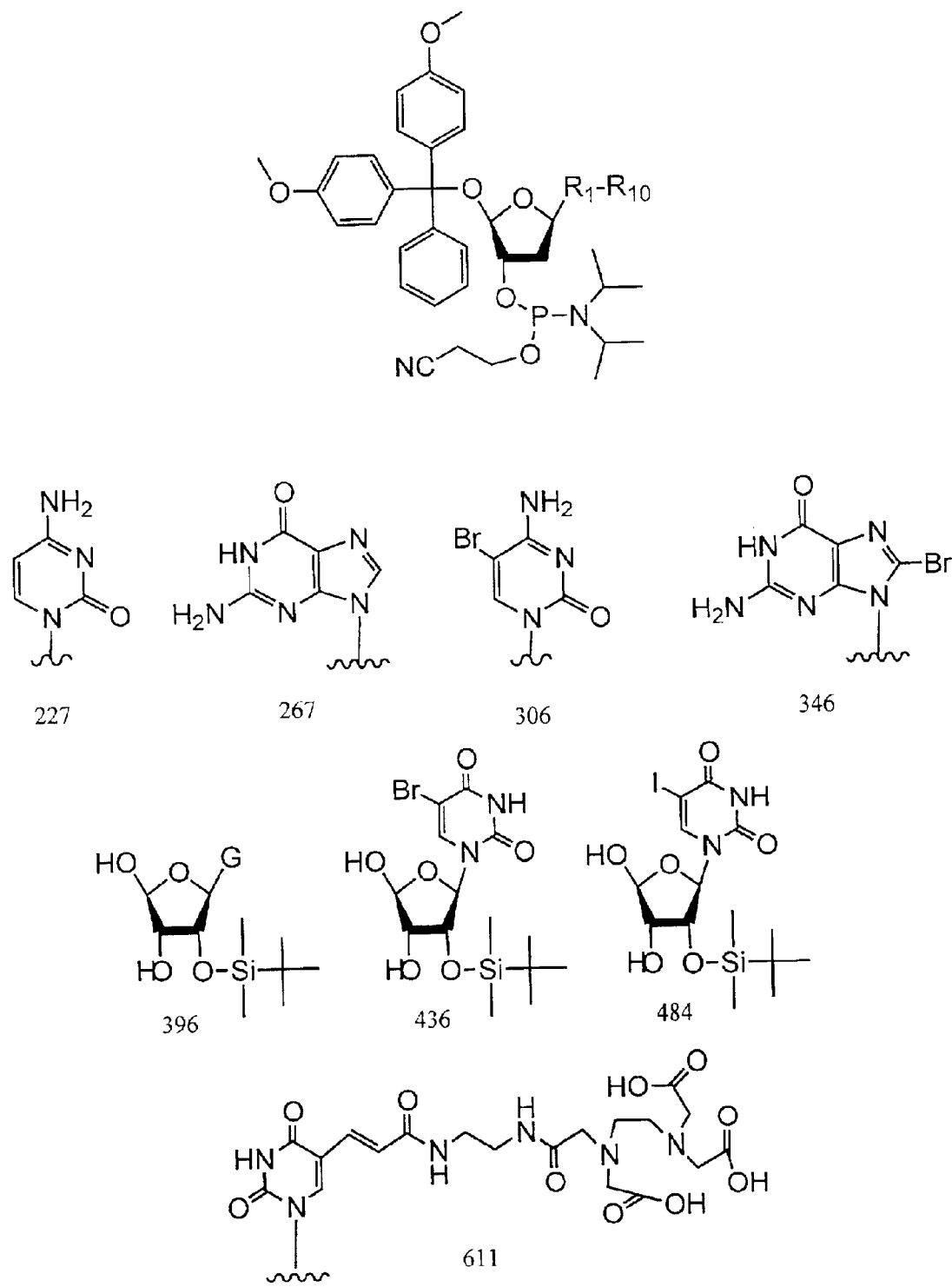
FIG. 7 gives the structure of several mobility-modified nucleic acid phosphoramidites that can be employed at the penultimate coupling during e-tag probe synthesis on a standard DNA synthesizer.

The penultimate coupling during probe synthesis is initially carried out using commercially available modified (and unmodified) phosphoramidites. FIG. 7 shows the structure of several mobility-modified nucleic acid phosphoramidites that can be employed at the penultimate coupling during e-tag probe synthesis on a standard DNA synthesizer.

This residue is able to form hydrogen bonds to its partner in the target strand and is considered a mass modifier but could potentially be a charge modifier as well. The phosphate bridge formed during this coupling is the linkage severed during the 5'-nuclease assay. The final coupling is done using a phosphoramidite analogue of a dye. Fluorescein is conveniently employed, but other dyes can be used as well.

Figure 6:
FIG. 6 provides predicted and experimental (*) elution times of e-tag reporters separated by capillary electrophoresis. $C_3$, $C_6$, $C_9$, and $C_{18}$ are commercially available phosphoramidite spacers from Glen Research, Sterling Va. The units are derivatives of N,N-diisopropyl, O-cyanoethyl phosphoramidite, which is indicated by "Q". $C_3$ is DMT (dimethoxytrityl)oxypropyl Q; $C_6$ is DMToxyhexyl Q; $C_9$ is DMToxy(triethyleneoxy) Q; $C_{12}$ is DMToxydodecyl Q; $C_8$ is DMToxy(hexaethyleneoxy) Q.
Figure 6:
Figure 6:
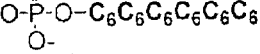
Figure 6:
Figure 6:
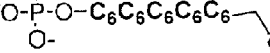
Figure 6:
Figure 6:
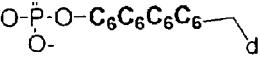
Figure 6:
Figure 6:
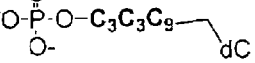
Figure 6:
Figure 6:
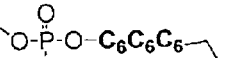
Figure 6:
Figure 6:
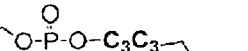
Figure 8:
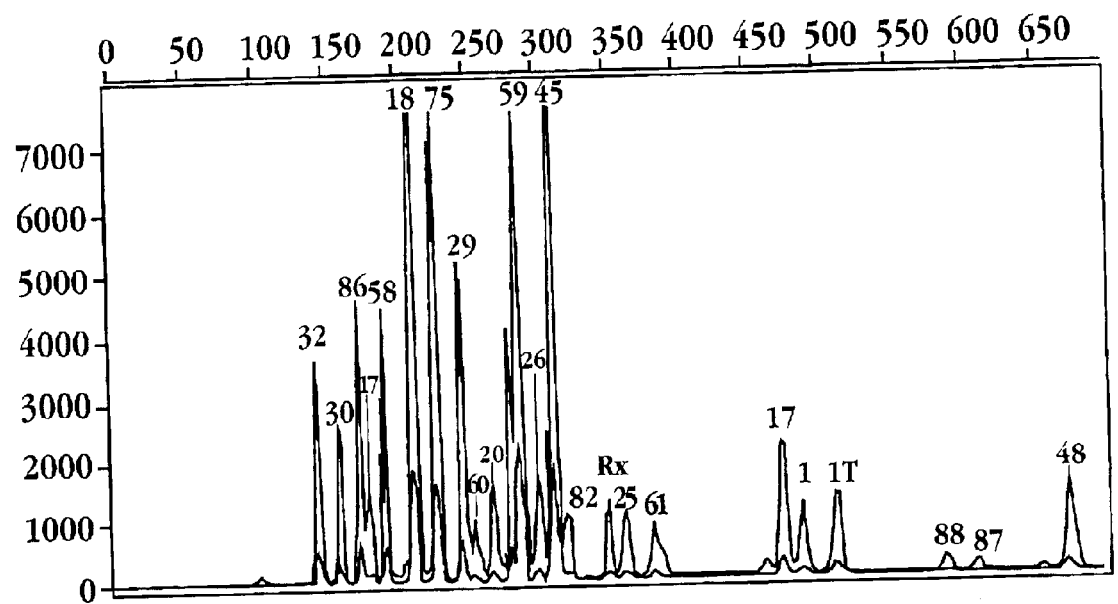
FIG. 8 shows multiple electropherograms showing separation of individual e-tag reporters. The figure illustrates obtainable resolution of the reporters, which are identified by their ACLA numbers.

FIG. 6 illustrates predicted and experimental (*) elution times of e-tag reporters. $C_3$, $C_6$, $C_9$, and $C_{18}$ are commercially available phosphoramidite spacers from Glen Research, Sterling VA. The units are derivatives of N,N-diisopropyl, O-cyanoethyl phosphoramidite, which is indicated by "Q". $C_3$ is DMT (dimethoxytrityl)oxypropyl Q; $C_6$ is DMToxyhexyl Q; $C_9$ is DMToxy(triethyleneoxy) Q; $C_{12}$ is DMToxydodecyl Q; $C_{18}$ is DMToxy(hexaethyleneoxy) Q. e-tags are synthesized to generate a contiguous spectrum of signals, one eluting after another with none of them coeluting (FIG. 8).

Figure 9:
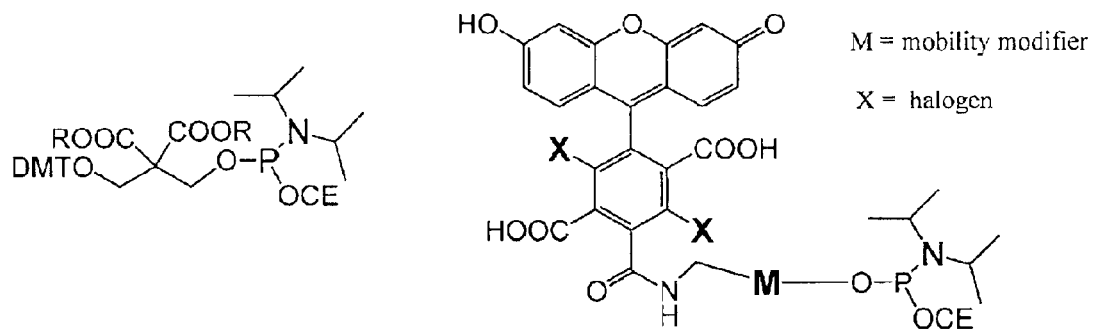
FIG. 9 shows charge modifier phosphoramidites. (EC or CE is cyanoethyl).
Figure 10:
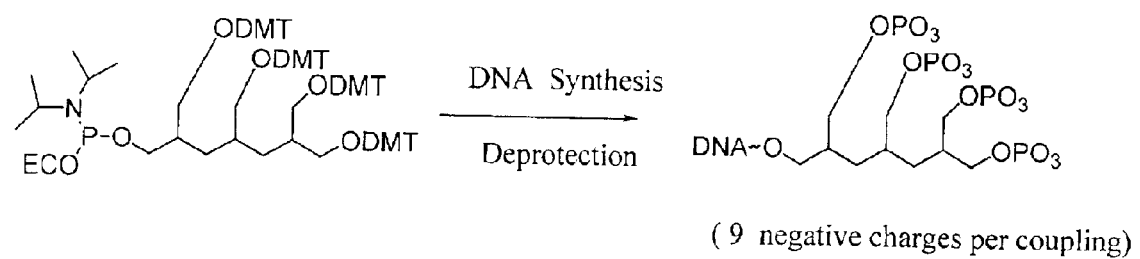
FIG. 10 shows polyhydroxylated charge modifier phosphoramidites.

All of the above e-tags work well and are easily separable and elute at 40 minutes. To generate tags that elute faster, highly charged low molecular weight tags are typically employed. Several types of phosphoramidite monomers allow for the synthesis of highly charged tags with early elution times. Use of dicarboxylate phosphoramidites (FIG. 9, left) allows for the addition of 3 negative charges per coupling of monomer. A variety of fluorescein derivatives (FIG. 9, right) allow the dye component of the tag to carry a higher mass than standard fluorescein. Polyhydroxylated phosphoramidites (FIG. 10) in combination with a common phosphorylation reagent enable the synthesis of highly phosphorylated tags. Combinations of these reagents with other mass modifier linker phosphoramidites allow for the synthesis of tags with early elution times.

The aforementioned label conjugates with different electrophoretic mobility permit a multiplexed amplification and detection of multiple targets, e.g. nucleic acid targets. The label conjugates are linked to oligonucleotides in a manner similar to that for labels in general, by means of linkages that are enzymatically cleavable. It is, of course, within the purview of the present invention to prepare any number of label conjugates for performing multiplexed determinations. Accordingly, for example, with 40 to 50 different label conjugates separated in a single separation channel and 96 different amplification reactions with 96 separation channels on a single plastic chip, one can detect 4000 to 5000 single nucleotide polymorphisms.

Figure 11:
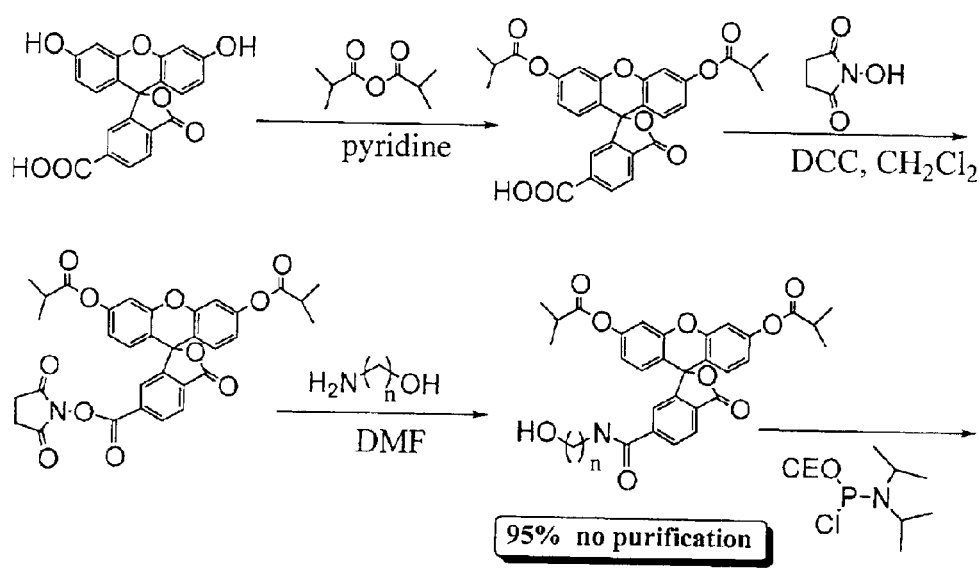
FIG. 11 illustrates one exemplary synthetic approach starting with commercially available 6-carboxy fluorescein, wherre the phenolic hydroxyl groups are protected using an anhydride. Upon standard extractive workup, a 95% yield of product is obtained. This material is phosphitylated to generate the phosphoramidite monomer.
Figure 12:
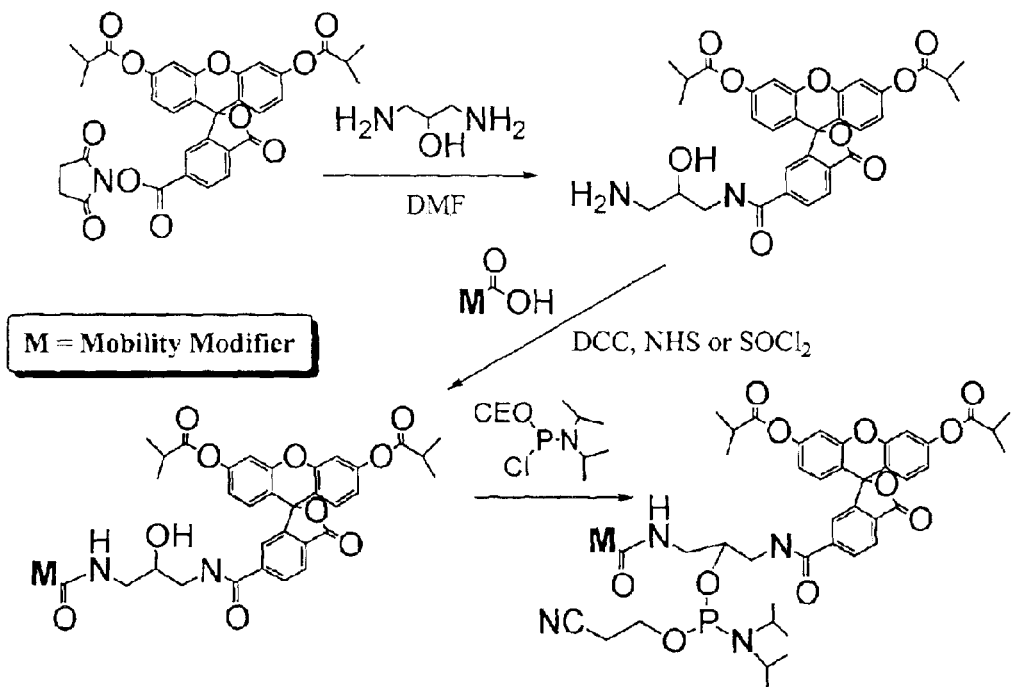
FIG. 12 illustrates the use of a symmetrical bis-amino alcohol linker as the amino alcohol with the second amine then coupled with a multitude of carboxylic acid derivatives.

One exemplary synthetic approach is outlined in FIG. 11. Starting with commercially available 6-carboxy fluorescein, the phenolic hydroxyl groups are protected using an anhydride. Isobutyric anhydride in pyridine was employed but other variants are equally suitable. It is important to note the significance of choosing an ester functionality as the protecting group. This species remains intact though the phosphoramidite monomer synthesis as well as during oligonucleotide construction. These groups are not removed until the synthesized oligo is deprotected using ammonia. After protection the crude material is then activated in situ via formation of an N-hydroxy succinimide ester (NHS-ester) using DCC as a coupling agent. The DCU byproduct is filtered away and an amino alcohol is added. Many amino alcohols are commercially available some of which are derived from reduction of amino acids. Only the amine is reactive enough to displace N-hydroxy succinimide. Upon standard extractive workup, a 95% yield of product is obtained. This material is phosphitylated to generate the phosphoramidite monomer (FIG. 11). For the synthesis of additional e-tags, a symmetrical bis-amino alcohol linker is used as the amino alcohol (FIG. 12). As such, the second amine is then coupled with a multitude of carboxylic acid derivatives (exemplified by several possible benzoic acid derivatives shown in FIG. 2) prior to the phosphitylation reaction. Using this methodology hundreds, even thousands of e-tags with varying charge to mass ratios can easily be assembled during probe synthesis on a DNA synthesizer using standard chemistries.

Figure 13:
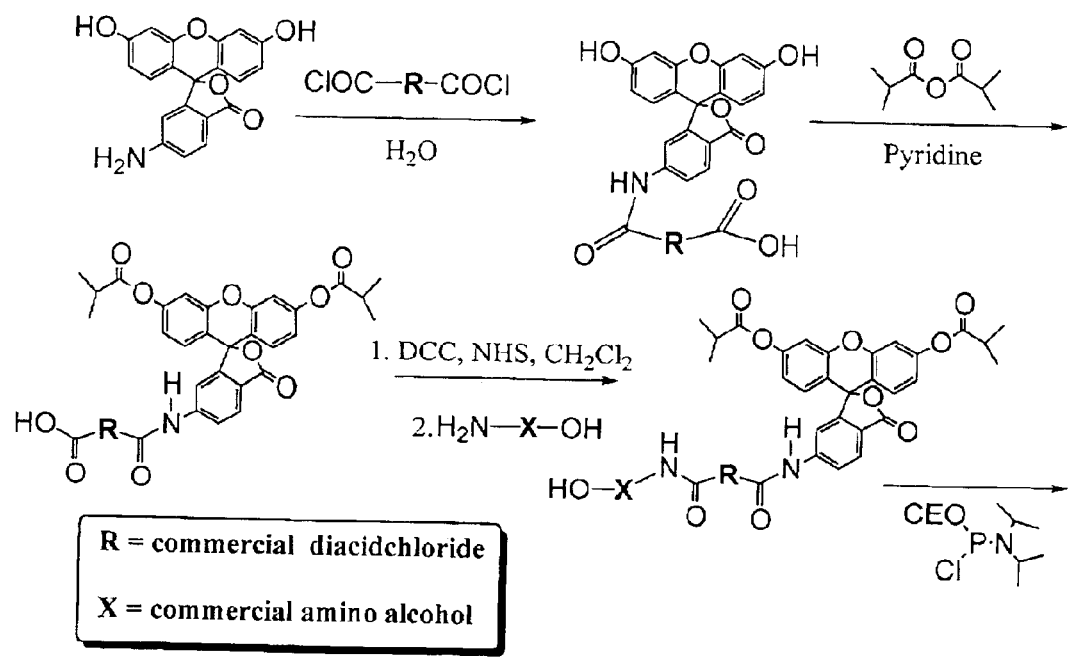
FIG. 13 illustrates the use of an alternative strategy that uses 5-aminofluorescein as starting material and the same series of steps to convert it to its protected phosphoramidite monomer.
Figure 14:
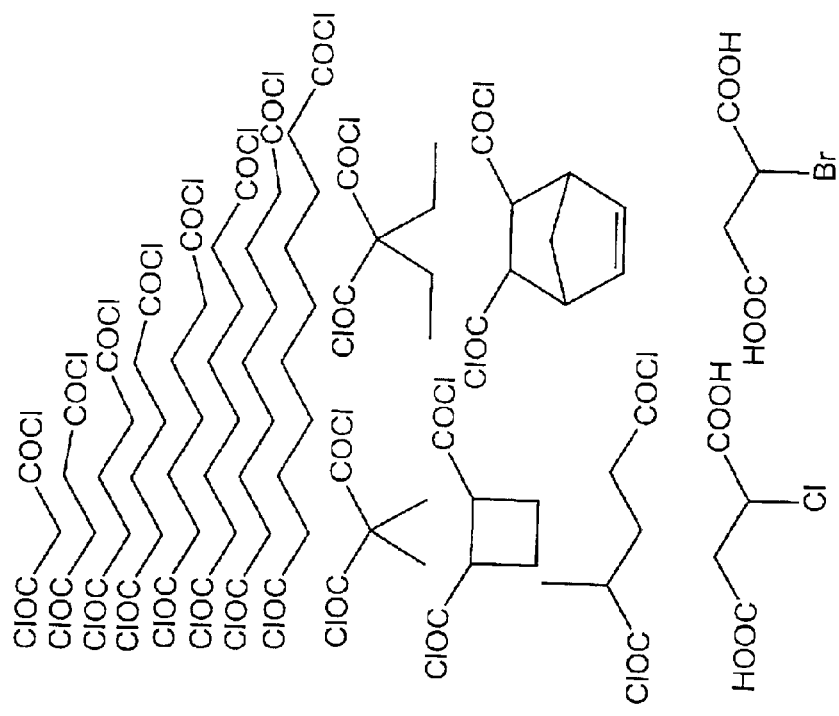
FIG. 14 illustrates several mobility modifiers that can be used for conversion of amino dyes into e-tag phosphoramidite monomers.
Figure 14:
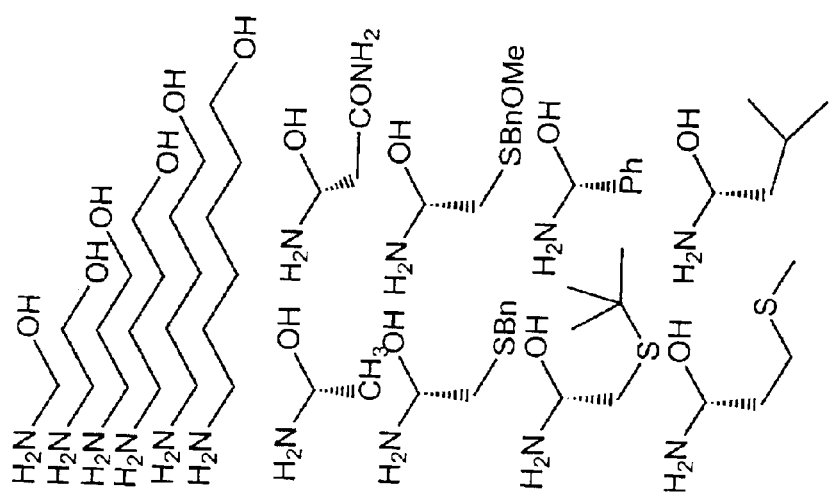

Alternatively, e-tags are accessed via an alternative strategy that uses 5-aminofluorescein as starting material (FIG. 13). Addition of 5-aminofluorescein to a great excess of a diacid dichloride in a large volume of solvent allows for the predominant formation of the monoacylated product over dimer formation. The phenolic groups are not reactive under these conditions. Aqueous workup converts the terminal acid chloride to a carboxylic acid. This product is analogous to 6-carboxyfluorescein, and using the same series of steps is converted to its protected phosphoramidite monomer (FIG. 13). There are many commercially available diacid dichlorides and diacids, which can be converted to diacid dichlorides using $SOCl_2$ or acetyl chloride. This methodology is highly attractive in that a second mobility modifier is used. As such, if one has access to 10 commercial modified phosphoramidites and 10 diacid dichlorides and 10 amino alcohols there is a potential for 1000 different e-tags. There are many commercial diacid dichlorides and amino alcohols (FIG. 14). These synthetic approaches are ideally suited for combinatorial chemistry.

Figure 15:
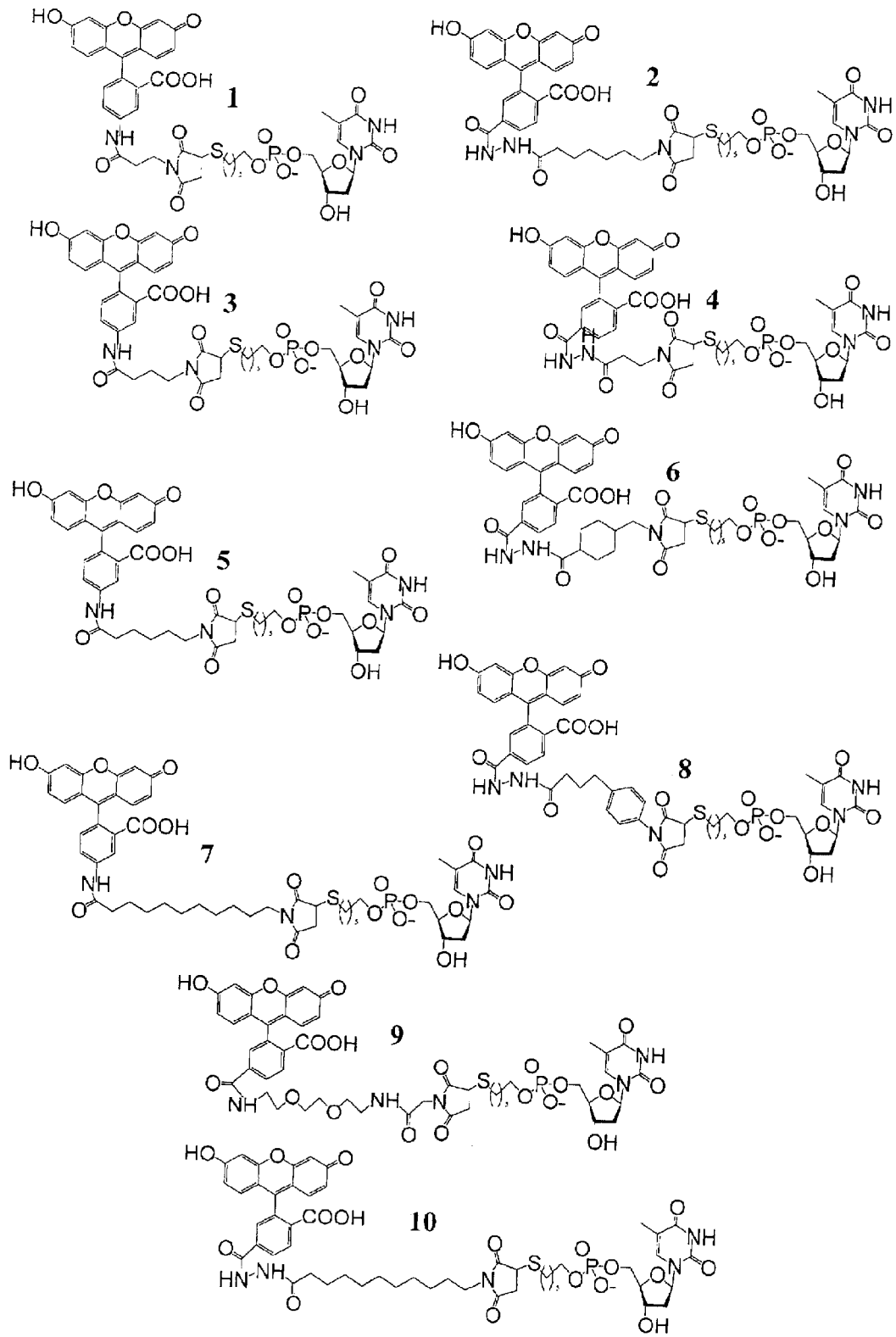
FIG. 15 gives the structure of several e-tags derived from maleimide-linked precursors.

A variety of maleimide-derivatized e-tags have also been synthesized. These compounds were subsequently bioconjugated to 5'-thiol adorned DNA sequences and subjected to the 5'-nuclease assay. The species formed upon cleavage are depicted in FIG. 15.

The eTag may be assembled having an appropriate functionality at one end for linking to the binding compound. Thus for oligonucleotides, one would have a phosphoramidite or phosphate ester at the linking site to bond to an oligonucleotide chain, either 5' or 3', particularly after the oligonucleotide has been synthesized, while still on a solid support and before the blocking groups have been removed. While other techniques exist for linking the oligonucleotide to the eTag, such as having a functionality at the oligonucleotide terminus that specifically reacts with a functionality on the eTag, such as maleimide and thiol, or amino and carboxy, or amino and keto under reductive amination conditions, the phosphoramidite addition is preferred. For a peptide-binding compound, a variety of functionalities can be employed, much as with the oligonucleotide functionality, although phosphoramidite chemistry may only occasionally be appropriate. Thus, the functionalities normally present in a peptide, such as carboxy, amino, hydroxy and thiol may be the targets of a reactive functionality for forming a covalent bond.

Of particular interest in preparing eTag labeled nucleic acid binding compounds (e-tag probes) is using the solid support phosphoramidite chemistry to build the eTag as part of the oligonucleotide synthesis. Using this procedure, one attaches the next succeeding phosphate at the 5' or 3' position, usually the 5' position of the oligonucleotide chain. The added phosphoramidite may have a natural nucleotide or an unnatural nucleotide. Instead of phosphoramidite chemistry, one may use other types of linkers, such as thio analogs, amino acid analogs, etc. Also, one may use substituted nucleotides, where the mass-modifying region and/or the charge-modifying region may be attached to the nucleotide, or a ligand may be attached to the nucleotide. In this way, phosphoramidite links are added comprising the regions of the eTag probe, whereby when the synthesis of the oligonucleotide chain is completed, one continues the addition of the regions of the eTag to complete the molecule. Conveniently, one would provide each of the building blocks of the different regions with a phosphoramidite or phosphate ester at one end and a blocked functionality, where the free functionality can react with a phosphoramidite, mainly a hydroxyl. By using molecules for the different regions that have a phosphoramidite at one site and a protected hydroxyl at another site, the eTag probe can be built up until the terminal region, which does not require the protected hydroxyl.

Illustrative of the synthesis would be to employ a diol, such as an alkylene diol, polyalkylene diol, with alkylene of from 2 to 3 carbon atoms, alkylene amine or poly(alkylene amine) diol, where the alkylenes are of from 2 to 3 carbon atoms and the nitrogens are substituted, for example with blocking groups or alkyl groups of from 1–6 carbon atoms, where one diol is blocked with a conventional protecting group, such as a dimethyltrityl group. This group can serve as the mass-modifying region and with the amino groups as the charge-modifying region as well. If desired, the mass modifier can be assembled using building blocks that are joined through phosphoramidite chemistry. In this way the charge modifier can be interspersed between within the mass modifier. For example, one could prepare a series of polyethylene oxide molecules having 1, 2, 3 . . . n units. Where one wished to introduce a number of negative charges, one could use a small polyethylene oxide unit and build up the mass and charge-modifying region by having a plurality of the polyethylene oxide units joined by phosphate units. Alternatively, by employing a large spacer, fewer phosphate groups would be present, so that without large mass differences, one would have large differences in mass-to-charge ratios.

The chemistry that is employed is the conventional chemistry used in oligonucleotide synthesis, where building blocks other than nucleotides are used, but the reaction is the conventional phosphoramidite chemistry and the blocking group is the conventional dimethoxyltrityl group. Of course, other chemistries compatible with automated synthesizers can also be used, but there is no reason to add additional complexity to the process.

For peptides, the e-tags will be linked in accordance with the chemistry of the linking group and the availability of functionalities on the peptide-binding compound. For example, with Fab' fragments specific for a target compound, a thiol group will be available for using an active olefin, e.g. maleimide, for thioether formation. Where lysines are available, one may use activated esters capable of reacting in water, such as nitrophenyl esters or pentafluorophenyl esters, or mixed anhydrides as with carbodiimide and half-ester carbonic acid. There is ample chemistry for conjugation in the literature, so that for each specific situation, there is ample precedent in the literature for the conjugation.

For separations based on sorption, adsorption and/or absorption, the nature of the e-tag reporters to provide for differentiation can be relatively simple. By using differences in composition, such as aliphatic compounds, aromatic compounds and halo derivatives thereof, one may make the determinations with gas chromatography, with electron capture or negative ion mass spectrometry, when electronegative atoms are present. In this way one may use hydrocarbons or halo-substituted hydrocarbons as the e-tag reporters bonded to a releasable linker. See, U.S. Pat. Nos. 5,565,324 and 6,001,579, which are specifically incorporated by reference as to the relevant disclosure concerning cleavable groups and detectable groups.

E. Sets of e-tags

The libraries will ordinarily have at least about 5 members, usually at least about 10 members, and may have 100 members or more, for convenience generally having about 50–75 members. Some members may be combined in a single container or be provided in individual containers, depending upon the region to which the mir is attached. The members of the library will be selected to provide clean separations in electrophoresis, when capillary electrophoresis is the analytical method. To that extent, mobilities will differ as described above, where the separations may be greater, the larger the larger the number of molecules in the band to be analyzed. Particularly, non-sieving media may be employed in the separation.

Besides the nature of the linker, mobility modifer or mir, as already indicated, diversity can be achieved by the chemical and optical characteristics of the fluorescer, the use of energy transfer complexes, variation in the chemical nature of the linker, which affects mobility, such as folding, interaction with the solvent and ions in the solvent, and the like. As already suggested, the linker will usually be an oligomer, where the linker may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality which may be differentially functionalized. By using protective groups, one can distinguish a side chain functionality from a terminal amino acid functionality. Also, by appropriate design, one may provide for preferential reaction between the same functionalities present at different sites on the linking group. Whether one uses synthesis or cloning for preparation of oligopeptides, will to a substantial degree depend on the length of the linker.

Depending upon the reagent to which the e-tag is attached, there may be a single e-tag or a plurality of e-tags, generally ranging from about 1–100, more usually ranging from about 1–40, more particularly ranging from about 1–20. The number of e-tags bonded to a single target-binding region will depend upon the sensitivity required, the solubility of the e-tag conjugate, the effect on the assay of a plurality of e-tags, and the like. For oligomers or polymers, such as nucleic acids and poly(amino acids), e.g. peptides and proteins, one may have one or a plurality of e-tags, while for synthetic or naturally occurring non-oligomeric compounds, usually there will be only 1–3, more usually 1–2 e-tags.

For 20 different e-tag reporters, one only requires 5 different mass-modifying regions, one phosphate link and four different detectable regions. For 120 e-tag reporters, one need only have 10 different mass-modifying regions, 3 different charge-modifying regions and 4 different detectable regions. For 500 different e-tag reporters, one need only have 25 different mass-modifying regions, 5 different charge-modifying regions and 4 different detectable regions.

III. Methods for use of the e-tag Technology

The methodologies that may be employed involve heterogeneous and homogeneous techniques, where heterogeneous normally involves a separation step, where unbound label is separated from bound label, where homogeneous assays do not require, but may employ, a separation step. One group of assays will involve nucleic acid detection, which includes sequence recognition, snp detection and scoring, transcription analysis, allele determinations, HLA determinations, or other determination associated with variations in sequence. The use of the determination may be forensic, mRNA determinations, mutation determinations, allele determinations, MHC determinations, haplotype determinations, single nucleotide polymorphism determinations, etc. The methodology may include assays dependent on 5'-nuclease activity, as in the use of the polymerase chain reaction or in Invader technology, 3'-nuclease activity, restriction enzymes, or ribonuclease H. All of these methods involving catalytic cleavage of a phosphate linkage, where one to two oligonucleotides are bound to the target template.

In addition, the subject heterogeneous assays require that the unbound labeled reagent be separable from the bound labeled reagent. This can be achieved in a variety of ways. Each way requires that a reagent bound to a solid support that distinguishes between the complex of labeled reagent and target. The solid support may be a vessel wall, e.g. microtiter well plate well, capillary, plate, slide, beads, including magnetic beads, liposomes, or the like. The primary characteristics of the solid support is that it permits segregation of the bound labeled specific binding member from unbound probe, and that the support does not interfere with the formation of the binding complex, nor the other operations of the determination.

The solid support may have the complex directly or indirectly bound to the support For directly bound, one may have the binding member or e-tag probe covalently or non-covalently bound to the support. For proteins, many surfaces provide non-diffusible binding of a protein to the support, so that one adds the protein to the support and allows the protein to bind, washes away weakly bound protein and then adds an innocuous protein to coat any actively binding areas that are still available. The surface may be activated with various functionalities that will form covalent bonds with a binding member. These groups may include imino halides, activated carboxyl groups, e.g. mixed anhydrides or acyl halides, amino groups, α-halo or pseudohaloketones, etc. The specific binding member bound to the surface of the support may be any molecule that permits the binding portion of the molecule, e.g. epitope, to be available for binding by the reciprocal member. Where the binding member is polyepitopic, e.g. proteins, this is usually less of a problem, since the protein will be polyepitopic and even with random binding of the protein to the surface, the desired epitope will be available for most of the bound molecules. For smaller molecules, particularly under 5 kDal, one will usually have an active functionality on the specific binding member that preserves the binding site, where the active functionality reacts with a functionality on the surface of the support. The same functionalities described above may find use. Conveniently, one may use the same site for preparing the conjugate immunogen to produce antibodies as the site for the active functionality for linking to the surface.

Instead of nucleic acid pairing, one may employ specific binding member pairing. There are a large number of specific binding pairs associated with receptors, such as antibodies, poly- and monoclonal, enzymes, surface membrane receptors, lectins, etc., and ligands for the receptors, which may be naturally occurring or synthetic molecules, protein or non-protein, such as drugs, hormones, enzymes, ligands, etc. The specific binding pair has many similarities to the binding of homologous nucleic acids, significant differences being that one normally cannot cycle between the target and the agent and one does not have convenient phosphate bonds to cleave. For heterogeneous assays, the binding of the specific binding pair is employed to separate the bound from the unbound e-tag bonded agents, while with homogeneous assays, the proximity of the specific binding pairs allow for release of the e-tags from the complex. For an inclusive but not exclusive listing of the various manners in which the subject invention may be used, Tables 3 and 4 are provided.

Once the binding compound (target binding moiety) conjugated with the e-tag has been prepared, it may find use in a number of different assays. The samples may be processed using lysis, nucleic acid separation from proteins and lipids and vice versa, and enrichment of different fractions. For nucleic acid related determinations, the source of the DNA may be any organism, prokaryotic and eukaryotic cells, tissue, environmental samples, etc. The DNA or RNA may be isolated by conventional means, RNA may be reverse transcribed, DNA may be amplified, as with PCR, primers may be used with capture ligands for use in subsequent processing, the DNA may be fragmented using restriction enzymes, specific sequences may be concentrated or removed using homologous sequences bound to a support, or the like. Proteins may be isolated using precipitation, extraction, and chromatography. The proteins may be present as individual proteins or combined in various aggregations, such as organelles, cells, viruses, etc. Once the target components have been preliminarily treated, the sample may then be combined with the e-tag reporter targeted binding proteins.

For a nucleic acid sample, after processing, the probe mixture of e-tags for the target sequences will be combined with the sample under hybridization conditions, in conjunction with other reagents, as necessary. Where the reaction is heterogeneous, the target-binding sequence will have a capture ligand for binding to a reciprocal binding member for sequestering hybrids to which the e-tag probe is bound. In this case, all of the DNA sample carrying the capture ligand will be sequestered, both with and without e-tag reporter labeled probe. After sequestering the sample, and removing non-specifically bound e-tag reporter labeled probe under a predetermined stringency based on the probe sequence, using washing at an elevated temperature, salt concentration, organic solvent, etc., the e-tag reporter is released into an electrophoretic buffer solution for analysis.

As indicated in Table 3, for amplification one may use thermal cycling. Tables 3 and 4 indicate the properties of binding assays (solution phase e-tag generation followed by separation by CE, HPLC or mass spectra) and multiplexed assays (2–1000) leading to release of a library of e-tags, where every e-tag codes for a unique binding event or assay.

The cleavage of the nucleic acid bound to the template results in a change in the melting temperature of the e-tag residue with release of the e-tag. By appropriate choice of the primer and/or protocol, one can retain the primer bound to the template and the e-tag containing sequence can be cleaved and released from the template to be replaced by an e-tag containing probe.

TABLE 3

Binding and Multiplexed Assays.

| Formats | Recognition Event | Amplification Mode | e-tag Release |
|---|---|---|---|
| Multiplexed assays Sequence recognition for example for multiplexed gene expression, SNP's scoring etc. . . . | Solution hybridization followed by enzyme recognition | PCR, Invader | 5' nuclease 3' nuclease Restriction enzyme Ribonuclease H |
|  | Solution hybridization followed by channeling | Amplification due to turnover of e-tag binding moiety; OR amplification due to release of multiple e-tags (10 to 100,000) per binding event | Singlet Oxygen ($^1O_2$) Hydrogen Peroxide ($H_2O_2$) Light, energy transfer |
| Patches in microfluidic channels - integrated assay and separation device | Target captured on solid surface; e-tag probe mixture hybridized to target; unbound probes removed; e-tag reporter is released, separated and identified. | Amplification from release of multiple e-tag reporters (10 to 100,000) per probe | Light, enzyme, $^1O_2$, $H_2O_2$, Fluoride, reducing agent MS, others |

TABLE 4

Immunoassays

| Format | Recognition Event | Amplification Mode | e-tag Release |
|---|---|---|---|
| Proteomics Multiplexed Immunoassays | Sandwich assays Antibody-1 decorated with Sensitizer while antibody-2 is decorated with singlet oxygen cleavable e-tags Competition assays Antibody-1 decorated with Sensitizer while antibody-2 is decorated with singlet oxygen cleavable e-tags | A few (2–10) e-tags released per binding event OR Amplification from release of multiple e-tags (10 to 100,000) per binding event | Singlet Oxygen ($^1O_2$) |
|  | Sandwich assays Antibody-1 decorated with Glucose oxidase while antibody-2 is decorated with hydrogen peroxide cleavable e-tags Competition assays Antibody-1 decorated with Glucose oxidase while antibody-2 is decorated with hydrogen peroxide cleavable e-tags |  | Hydrogen Peroxide ($H_2O_2$) |
| Patches in microfluidic channels; integrated assay and separation device | Sandwich assays Antibody-1 is attached to a solid surface while antibody-2 is decorated with cleavable e-tags Competition assays Antibody-1 is attached to a solid surface while antibody-2 is decorated with cleavable e-tags |  | Light; Enzymes, singlet oxygen, hydrogen peroxide fluoride, reducing agents, mass spectra, others |

The assays may be performed in a competitive mode or a sandwich mode. In the competitive mode, one has the target competing with a labeled binding member for the reciprocal member, which reciprocal member is bound to the support, either during the complex formation or after, e.g. where an antibody is a specific binding member and anti-immunoglobulin is the reciprocal binding member and is bound to the support. In this mode, the binding sites of the reciprocal binding member become at least partially filled by the target, reducing the number of available binding sites for the labeled reciprocal binding member. Thus, the number of labeled binding members that bind to the reciprocal binding member will be in direct proportion to the number of target molecules present. In the sandwich mode, the target is able to bind at the same time to different binding members; a first support bound member and a second member that binds at a site of the target molecule different from the site at which the support bound member binds. The resulting complex has three components, where the target serves to link the labeled binding member to the support.

In carrying out the assays, the components are combined, usually with the target composition added first and then the labeled members in the competitive mode and in any order in the sandwich mode. Usually, the labeled member in the competitive mode will be equal to at least 50% of the highest number of target molecules anticipated, preferably at least equal and may be in 2 to 10 fold excess or greater. The particular ratio of target molecules to labeled molecules will depend on the binding affinities, the length of time the mixture is incubated, the off rates for the target molecule with its reciprocal binding member, the size of the sample and the like. In the case of the sandwich assays, one will have at least an equal amount of the labeled binding member to the highest expected amount of the target molecules, usually at least 1.5 fold excess, more usually at least 2 fold excess and may have 10 fold excess or more. The components are combined under binding conditions, usually in an aqueous medium, generally at a pH in the range of 5–10, with buffer at a concentration in the range of about 10 to 200 mM. These conditions are conventional, where conventional buffers may be used, such as phosphate, carbonate, HEPES, MOPS, Tris, borate, etc., as well as other conventional additives, such as salts, stabilizers, organic solvents, etc.

Usually, the unbound labeled binding member or e-tag probe will be removed by washing the bound labeled binding member. Where particles or beads are employed, these may be separated from the supernatant before washing, by filtration, centrifugation, magnetic separation, etc. After washing, the support may be combined with a liquid into which the e-tag reporters are to be released and/or the functionality of the e-tags is reacted with the detectable label, followed by or preceded by release. Depending on the nature of the cleavable bond and the method of cleavage, the liquid may include reagents for the cleavage. Where reagents for cleavage are not required, the liquid is conveniently an electrophoretic buffer. For example, where the cleavable linkage is photo labile, the support may be irradiated with light of appropriate wavelength to release the e-tag reporters. Where detectable labels are not present on the e-tags, the e-tags may be reacted with detectable labels. In some instances the detectable label may be part of the reagent cleaving the cleavable bond, e.g. a disulfide with a thiol. Where there is a plurality of different functionalities on different binding members for reaction with the label, the different labels will have functionalities that react with one of the functionalities. The different labels may be added together or individually in a sequential manner. For example, where the functionalities involve thiols, carboxyl groups, aldehydes and olefins, the labels could have activated olefins, alcohols, amines and thiol groups, respectively. By having removable protective groups for one or more of the functionalities, the protective groups may be removed stepwise and the labels added stepwise. In this way cross-reactivity may be avoided. Whether one has the detectable label present initially or one adds the detectable label is not critical to this invention and will frequently be governed by the nature of the target composition, the nature of the labeled binding members, and the nature of the detectable labels. For the most part, it will be a matter of convenience as to the particular method one chooses for providing the detectable label on the e-tag.

Where a reagent is necessary for cleavage, the e-tag reporters may be required to be separated from the reagent solution, where the reagent interferes with the electrophoretic analysis. Depending on the nature of the e-tag reporters and the reagent, one may sequester the e-tag reporters from the reagent by using ion exchange columns, liquid chromatography, an initial electrophoretic separation, and the like. Alternatively, as discussed previously, one may have a capture ligand bound to the e-tag or retained portion of the target-binding region for isolating the e-tag probe, so as to remove any interfering components in the mixture. Once the solution of e-tag reporters is prepared and free of any interfering components, the solution may be analyzed electrophoretically. The analysis may employ capillary electrophoresis devices, microfluidic devices or other devices that can separate a plurality of compounds electrophoretically, providing resolved bands of the individual e-tag reporters.

The protocols for the subject homogeneous assays will follow the procedures for the analogous heterogeneous assays, which may or may not include a releasable e-tag. These protocols employ a signal producing system that includes the label on one of the binding members, the cleavable bond associated with the e-tag, electromagnetic radiation or other reagents involved in the reaction or for diminishing background signal. In assays involving the production of hydrogen peroxide, one may wish to have a molecule in solution that degrades hydrogen peroxide to prevent reaction between hydrogen peroxide produced by a label bound to an analyte molecule and an e-tag labeled binding member that is not bound to the same analyte molecule.

Generally, the concentrations of the various agents involved with the signal producing system will vary with the concentration range of the individual analytes in the samples to be analyzed, generally being in the range of about 10 nM to 10 mM. Buffers will ordinarily be employed at a concentration in the range of about 10 to 200 mM. The concentration of each analyte will generally be in the range of about 1 pM to about 100 $\mu$M, more usually in the range of about 100 pM to 10 $\mu$M. In specific situations the concentrations may be higher or lower, depending on the nature of the analyte, the affinity of the reciprocal binding members, the efficiency of release of the e-tag reporters, the sensitivity with which the e-tags are detected, and the number of analytes, as well as other considerations.

The reactive species that is produced in the assay, analogous to the subject assay, is employed in a different way than was used in the analogous assay, but otherwise the conditions will be comparable. In many instances, the chemiluminescent compound when activated will result in cleavage of a bond, so that one may obtain release of the e-tag reporter. Assays that find use are described in U.S. Pat. Nos. 4,233,402, 5,616,719, 5,807,675, and 6,002,000. One would combine the analyte with one or both reagents. The particular order of addition will vary with the nature of the reagents. Generally, one would prefer to combine the binding reagents and the sample and allow the mixture to incubate, generally at least about 5 min, more usually at least about 15 min, before irradiating the mixture or adding the remaining reagents.

One may also use the subject libraries of e-tags to analyze the effect of an agent on a plurality of different compounds. For example, one may prepare a plurality of substrates labeled with an e-tag, where the enzyme catalyzes a reaction resulting in a change in mobility between the product and the starting material. These assays can find use in determining affinity groups or preferred substrates for hydrolases, oxidoreductases, lyases, etc. For example, with kinases and phosphatases, one adds or removes a charged group, so as to change the mobility of the product. By preparing a plurality of alcohols or phosphate esters, one can determine which of the compounds serves as a substrate. By labeling the substrates with e-tags, one can observe the shift from the substrate to the product as evidence of the activity of a candidate substrate with the enzyme. By preparing compounds as suicide inhibitors, the enzymes may be sequestered and the e-tag reporters released to define those compounds that may serve as suicide inhibitors and, therefore, preferentially bind to the active site of the enzyme.

One may also use the subject methods for screening for the activity of one or more candidate compounds, particularly drugs, for their activity against a battery of enzymes. In this situation, one would use active substrates for each of the enzymes to be evaluated, where each of the substrates would have its own e-tag. For those enzymes for which the drug is an inhibitor, the amount of product would be diminished in relation to the amount of product in the absence of the candidate compound. In each case the product would have a different mobility from the substrate, so that the substrates and products could be readily distinguished by electrophoresis. By appropriate choice of substrates and detectable labels, one would obtain electropherograms showing the effect of the candidate compound on the activity of the different enzymes.

In determinations involving nucleic acids, since snp detection is, for the most part, the most stringent in its requirements, most of the description will be directed toward the multiplexed detection of snps. For other nucleic acid analyses, frequently the protocols will be substantially the same, although in some instances somewhat different protocols will be employed for snps, because of the greater demands snps make on fidelity. For proteins, the protocols will be substantially different and will be described independently of the snp protocols.

For proteins, the protocols will be different and will be described independently of the SNP protocols.

A. Primer Extension Reaction in Nucleic Acid Analyses

The extension reaction is performed by bringing together the necessary combination of reagents, and subjecting the mixture to conditions for carrying out the desired primer extension. Such conditions depend on the nature of the extension, e.g., PCR, single primer amplification, LCR, NASBA, 3SR and so forth, where the enzyme which is used for the extension has 5'-3' nuclease activity. The extension reaction may be carried out as to both strands or as to only a single strand. Where pairs of primer and SNP detection sequence are used for both strands, conveniently, the e-tag will be the same but the bases will be different. In this situation, one may wish to have a cleavable linkage to the base, so that for the same SNP, one would obtain the same e-tag. Alternatively, if the number of SNPs to be determined is not too high, one could use different e-tags for each of the strands. Usually, the reaction will be carried out by using amplifying conditions, so as to provide an amplified signal for each SNP. Amplification conditions normally employ thermal cycling, where after the primer extension and release of electrophoretic tag reporters associated with snps' which are present, the mixture is heated to denature the double-stranded DNA, cooled, where the primer and snp detection sequence can rehybridize and the extension be repeated.

Reagents for conducting the primer extension are substantially the same reaction materials for carrying out an amplification, such as an amplification indicated above. The nature and amounts of these reagents are dependent on the type of amplification conducted. In addition to oligonucleotide primers, the reagents also comprise nucleoside triphosphates and a nucleotide polymerase having 5'-3' nuclease activity.

The nucleoside triphosphates employed as reagents in an amplification reaction include deoxyribonucleoside triphosphates such as the four common deoxyribonucleoside triphosphates dATP, dCTP, dGTP and dTTP. The term "nucleoside triphosphates" also includes derivatives and analogs thereof, which are exemplified by those derivatives that are recognized and polymerized in a similar manner to the underivatized nucleoside triphosphates.

The nucleotide polymerase employed is a catalyst, usually an enzyme, for forming an extension of an oligonucleotide primer along a polynucleotide such as a DNA template, where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Vent DNA polymerase, Pfu DNA polymerase, Taq DNA polymerase, and the like. Polymerase enzymes may be derived from any source, such as eukaryotic or prokaryotic cells, bacteria such as E. coli, plants, animals, virus, thermophilic bacteria, genetically modified enzymes, and so forth.

The conditions for the various amplification procedures are well known to those skilled in the art. In a number of amplification procedures, thermal cycling conditions as discussed above are employed to amplify the polynucleotides. The combination of reagents is subjected to conditions under which the oligonucleotide primer hybridizes to the priming sequence of, and is extended along, the corresponding polynucleotide. The exact temperatures can be varied depending on the salt concentration, pH, solvents used, length of and composition of the target polynucleotide sequence and the oligonucleotide primers.

Thermal cycling conditions are employed for conducting an amplification involving temperature or thermal cycling and primer extension such as in PCR or single primer amplification, and the like. The pH and the temperature are selected so as to cause, either simultaneously or sequentially, dissociation of any internally hybridized sequences, hybridization or annealing of the oligonucleotide primer and snp detection sequence with the target polynucleotide sequence, extension of the primer, release of the e-tag reporter from snp detection sequence bound to the target polynucleotide sequence, and dissociation of the extended primer. This usually involves cycling the reaction medium between two or more temperatures. In conducting such a method, the medium is cycled between two to three temperatures. The temperatures for thermal cycling generally range from about 50° C. to 100° C., more usually from about 60° C. to 95° C. Relatively low temperatures of from about 30° C. to about 65° C. can be employed for the extension steps, while denaturation and hybridization can be carried out at a temperature of from about 50° C. to about 105° C. The reaction medium is initially at about 20° C. to about 45° C., preferably, about 25° C. to about 35° C. Relatively low temperatures of from about 50° C. to about 80° C., preferably, 50° C. to about 60° C., are employed for the hybridization or annealing steps, while denaturation is carried out at a temperature of from about 80° C. to about 100° C., preferably, 90° C. to about 95° C., and extension is carried out at a temperature of from about 70° C. to about 80° C., usually about 72° C. to about 74° C. The duration of each cycle may vary and is usually about 1 to 120 seconds, preferably, about 5 to 60 seconds for the denaturation steps, and usually about 1 to 15 seconds, preferably, about 1 to 5 seconds, for the extension steps. It is to be understood that the actual temperature and duration of the cycles employed are dependent on the particular amplification conducted and are well within the knowledge of those skilled in the art.

Generally, an aqueous medium is employed. Other polar co-solvents may also be employed, usually oxygenated organic solvents of from 1–6, more usually from 1–4, carbon atoms, including alcohols, ethers, formamide and the like. Usually, these co-solvents, if used, are present in less than about 70 weight percent, more usually in less than about 30 weight percent.

The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another. The medium may also contain materials required for enzyme activity such as a divalent metal ion (usually magnesium).

Various ancillary materials will frequently be employed in the methods in accordance with the present invention. For example, in addition to buffers and salts, the medium may also comprise stabilizers for the medium and the reaction components. Frequently, the medium may also include proteins such as albumins, quaternary ammonium salts, polycations such as spermine, surfactants, particularly non-ionic surfactants, binding enhancers, e.g., polyalkylene glycols, or the like.

The reaction is conducted for a time sufficient to produce the desired number of copies of each of the polynucleotides suspected of being present as discussed below. Generally, the time period for conducting the entire method will be from about 10 to 200 minutes. As mentioned above, it is usually desirable to minimize the time period.

The concentration of the nucleotide polymerase is usually determined empirically. Preferably, a concentration is used that is sufficient such that the amplification is robust. The primary limiting factor generally is the cost of the reagent. Such enzymes include Pfu DNA polymerase (native and recombinant) from Stratagene, La Jolla, Calif., UlTma DNA polymerase from Perkin Elmer, Foster City, Calif., rBst DNA polymerase from Epicentre Technologies, Madison, Wis., Vent DNA polymerase from New England Biolabs, Beverly, Mass., Tli DNA polymerase from Promega Corp., Madison, Wis., and Pwo DNA polymerase from Boehringer Mannheim, Indianapolis, Ind., and the like.

The initial concentration of each of the polynucleotides containing the respective target-binding moiety for the target snps can be as low as about 50 pg/$\mu$L in a sample. After amplification the concentration of each polynucleotide should be at least about 10 pM, generally in the range of about 10 pM to about 10 nM, usually from about 10 to $10^{10}$, more usually from about $10^3$ to $10^8$ molecules in a sample, preferably at least $10^{-21}$ M in the sample and may be $10^{-10}$ to $10^{-19}$ M, more usually $10^{-14}$ to $10^{-19}$ M. In general, the reagents for the reaction are provided in amounts to achieve extension of the oligonucleotide primers.

The concentration of the oligonucleotide primer(s) will be about 1 to about 20 $\mu$M and is usually about 1 to about 10 $\mu$M, preferably, about 1 to about 4 $\mu$M, for a sample size that is about 10 fM. Preferably, the concentration of the oligonucleotide primer(s) is substantially in excess over, preferably at least about $10^7$ to about $10^{10}$ times greater than, more preferably, at least about $10^9$ times greater than, the concentration of the corresponding target polynucleotides.

The amount of the oligonucleotide probes will be 10 to about 500 nM and is usually about 50 to about 200 nM for a sample size that is about 10 fM. Preferably, the concentration of the oligonucleotide probes is substantially in excess over, preferably at least about $10^7$ times greater than, more preferably, at least about $10^8$ times greater than, the concentration of each of the target polynucleotides.

The concentration of the nucleoside triphosphates in the medium can vary widely; preferably, these reagents are present in an excess amount. The nucleoside triphosphates are usually present in about 10 $\mu$M to about 1 mM, preferably, about 20 to about 400 $\mu$M.

The order of combining of the various reagents to form the combination may vary. Usually, the sample containing the polynucleotides is combined with a pre-prepared combination of nucleoside triphosphates and nucleotide polymerase. The oligonucleotide primers and the SNP detection sequences may be included in the prepared combination or may be added subsequently. However, simultaneous addition of all of the above, as well as other step-wise or sequential orders of addition, may be employed provided that all of the reagents described above are combined prior to the start of the reactions. The oligonucleotide pairs may be added to the combination of the reagents at or prior to initiation of the primer extension reaction and may be replenished from time-to-time during the primer extension reaction.

For quantitation, one may choose to use controls, which provide a signal in relation to the amount of the target that is present or is introduced. Where one is dealing with a mixture of nucleic acid molecules, as in the case of mRNA in a lysate, one may use the known amounts of one or more different mRNAs in the particular cell types as the standards. Desirably, one would have at least two controls, preferably at least 3 controls, where the variation in number between any two controls is at least about IO2, and the total range is at least about $10^3$, usually at least about $10^4$. However, determining the consistent ratio of mRNAs occurring naturally may result in a large margin of error, so that one would usually rely on synthetic targets as the control. Where a control system is added for quantitation, as compared to relying on the presence of a known amount of a plurality of endogenous nucleic acids, the control system will comprise at least two control sequences, usually at least 3 control sequences and generally not more than about 6 control sequences, where the upper limit is primarily one of convenience and economy, since additional control sequences will usually not add significant additional precision. The control sequences will usually be at least about 50 nucleotides, more usually at least about 100 nucleotides. The control sequences will have a common primer sequence and different control detection sequences, which are intended to parallel the primer sequence and SNP detection sequence in size, spacing and response to the primer extension conditions. In carrying out the primer extension reaction with sample nucleic acid, one would then add different number of molecules of the different control sequences, so that one could graph the result to give a signal/number relationship. This graph could then be used to relate signals observed with target molecules to the number of molecules present.

As exemplary of the subject invention, four target polynucleotides T1, T2, T3 and T4 are employed. Oligonucleotide primers PR1, PR2, PR3 and PR4 are employed, each respectively capable of hybridizing to a sequence in the respective target polynucleotides. Also employed are four oligonucleotide snp detection sequences, PB1, PB2, PB3 and PB4. Each of the snp detection sequences comprises a fluorescent label F1, F2, F3 and F4, respectively. In this example, there is a mismatch between PB2 and T2, which comprises a single nucleotide polymorphism. The reaction medium comprising the above reagents and nucleoside triphosphates and a template dependent polynucleotide polymerase having 5' to 3' exonuclease activity is treated under amplification conditions. Primers PR1, PR2, PR3 and PR4 hybridize to their respective target polynucleotides and are extended to yield extended primers EPR 1, EPR2, EPR3 and EPR4. snp detection sequences PB1, PB3 and PB4, which hybridize with their respective target polynucleotides, are acted upon by the exonuclease to cleave a single nucleotide bearing the respective fluorescent label. PB2, which does not bind to the target polynucleotide, is not cleaved. Cleaved fragments F1, F3 and F4 are injected into a separation channel in a chip for conducting electroseparation. The labels are identified by their specific mobility and fluorescence upon irradiation. The separated labels are related to the presence and amount of the respective target polynucleotide.

The selection of the snp detection or other target binding sequence will affect the stringency employed during the primer extension, particularly at the stage of hybridization. Since in a substantial number of samples, the DNA will be heterozygous for snps', rather than homozygous, one does not wish to have false positives, where the snp detection sequence may bond to the sequence comprising the prevalent nucleotide, as well as the sequence comprising the snp. Where the DNA sample is homozygous for the prevalent sequence, it is also important that the target binding sequence does not bind to give a false positive. Therefore, the difference in $T_m$ between the target containing sequence and the wild-type sequence will usually be at least about 3° C., more usually at least about 5° C., under the conditions of the primer extension.

In one exemplary protocol, the tagged snp detection sequence will be chosen to bind to the target sequence comprising the snp. The length of the snp detector sequence is in part related to the length and binding affinity of the primer. The two sequences act together to ensure that the pair of reagents bind to the proper target sequence. The greater the fidelity of binding of one member of the pair, the less fidelity that is required for the other member of the pair. Since the observed signal will be dependent upon both members of the pair being present, each member serves as a check on the other member for production of the signal. However, since except for the cost, it is relatively easy to make reasonably long oligonucleotides, usually both members of the pair will uniquely hybridize to their respective target sequences. Therefore, the length of the snp detector sequence will come within the parameters indicated for the primer, but the total number of bases for the two pair members will usually be at least 36, more usually at least about 40.

Depending on the protocol, an e-tag reporter will be separated from a portion or substantially all of the detection sequence, usually retaining not more than about 3 nucleotides, more usually not more than about 2 nucleotides and preferably from 0 to 1 nucleotide. By having a cleavable linker between the e-tag and the detection sequence, the e-tag reporter may be freed of all the nucleotides. By having a nuclease-resistant penultimate link, a single nucleotide may be bonded to the e-tag.

Each snp detection sequence will have at least one nucleotide modified with an electrophoretic tag, which is fluorescent or can be subsequently made fluorescent, or can be detected electrochemically or by other convenient detection methodologies. Usually, the modified nucleotide will be at the 5'-end of the sequence, but the modified nucleotide may be anywhere in the sequence, particularly where there is a single nuclease susceptible linkage in the detection sequence. Since the determination is based on at least partial degradation of the snp detector sequence, having the modified nucleotide at the end ensures that if degradation occurs, the electrophoretic tag will be released. Since nucleases may clip at other than the terminal phosphate link, it is desirable to prevent cleavage at other than the terminal phosphate link. In this way one avoids the confusion of having the same electrophoretic tag joined to different numbers of nucleotides after cleavage. Cleavage at the terminal phosphate can be relatively assured by using a linker that is not cleaved by the nuclease, more particularly having only the ultimate linkage susceptible to hydrolysis by a nuclease. For example, one may use a thiophosphate, phosphinate, phosphoramidate, or a linker other than a phosphorous acid derivative, such as an amide, boronate, or the like. The particular hydrolase resistant linker will be primarily one of synthetic convenience, so long as degradation of the binding affinity is not sacrificed. If desired, all of the linkers other than the ultimate linker may be resistant to nuclease hydrolysis.

One, usually a plurality, of snp's, is simultaneously determined by combining target DNA with one or a plurality, respectively, of reagent pairs under conditions of primer extension. Each pair of reagents includes a primer which binds to target DNA and a snp detection sequence, normally labeled, which binds to the site of the snp and has an e-tag, usually at its 5'-end and the base complementary to the snp, usually at other than a terminus of the snp detection sequence. The conditions of primer extension employ a polymerase having 5'-3' exonuclease activity, dNTP's and auxiliary reagents to permit efficient primer extension. The primer extension is performed, whereby detector sequences bound to the target DNA are degraded with release of the e-tag. By having each snp associated with its own e-tag, one can determine the snp's, which are present in the target DNA for which pairs of reagents have been provided.

The pairs of reagents are DNA sequences which are related to a snp site. The primer binds to the target DNA upstream from the snp site in the direction of extension. The labeled detector sequence binds downstream from the primer in the direction of extension and binds to a sequence, which includes the snp. The primer sequence will usually be at least about 12 bases long, more usually at least 18 bases long and usually fewer than 100 bases, and more usually fewer than 60 bases. The primer will be chosen to bind substantially uniquely to a target sequence under the conditions of primer extension, so that the sequence will normally be one that is conserved or the primer is long enough to bind in the presence of a few mismatches, usually fewer than about 10 number % mismatches. By knowing the sequence, which is upstream from the snp of interest, one may select a sequence, which has a high G-C ratio, so as to have a high binding affinity for the target sequence. In addition, the primer should bind reasonably close to the snp, usually not more than about 200 bases away, more usually not more than about 100 bases away, and preferably within about 50 bases. Since the farther away the primer is from the snp, the greater amount of dNTPs that will be expended, there will usually be no advantage in having a significant distance between the primer and the snp detection sequence. Generally, the primer will be at least about 5 bases away from the snp.

The complementary base to the snp may be anywhere in the detector sequence, desirably at other than the terminal nucleoside to enhance the fidelity of binding. The SNP detector sequence will be designed to include adjacent nucleotides, which provide the desired affinity for the hybridization conditions. The SNP detection sequence may be synthesized by any convenient means, such as described in Matthews, et al., Anal. Biochem. (1988) 169:1–25; Keller, et al., "DNA Probes," $2^{nd}$ edition (1993) Stockton Press, New York, N.Y.; and Wetmur, Critical Reviews in Biochemistry and Molecular Biology (1991) 26:227–259.

The number of reagent pairs may be varied widely, from a single pair to two or more pairs, usually at least about 5 pairs, more usually at least about 9 pairs and may be 20 pairs or more. By virtue of the use of different e-tags, which have different mobilities and are readily resolvable under conventional capillary electrophoretic conditions, the subject pairs may be used to perform multiplexed operations in a single vessel, where a family of SNPs may be identified. Usually, the total number of different reagent pairs or different target sequences in a single determination will be under 200, more usually under 100 and in many cases will not exceed 50.

B. The Invader™ Reaction in Nucleic Acid Analyses

In one SNP determination protocol, the primer includes the complementary base of the SNP. This protocol is referred to as Invader™ technology, and is described in U.S. Pat. No. 6,001,567. The protocol involves providing: (a) (i) a cleavage means, which is normally an enzyme, referred to as a cleavase, that recognizes a triplex consisting of the target sequence, a primer which binds to the target sequence and terminates at the SNP position and a labeled probe that binds immediately adjacent to the primer and is displaced from the target at the SNP position, when a SNP is present. The cleavase clips the labeled probe at the site of displacement, releasing the label, (ii) a source of target nucleic acid, the target nucleic acid having a first region, a second region and a third region, wherein the first region is downstream from the second region and the second region is contiguous to and downstream from the third region, and (iii) first and second oligonucleotides having 3' and 5' portions, wherein the 3' portion of the first oligonucleotide contains a sequence complementary to the third region of the target nucleic acid and the 5' portion of the first oligonucleotide and the 3' portion of the second oligonucleotide each contain sequences usually fully complementary to the second region of the target nucleic acid, and the 5' portion of the second oligonucleotide contains sequence complementary to the first region of said target nucleic acid; (b) mixing, in any order, the cleavage means, the target nucleic acid, and the first and second oligonucleotides under hybridization conditions that at least the 3' portion of the first oligonucleotide is annealed to the target nucleic acid and at least the 5' portion of the second oligonucleotide is annealed to any target nucleic acid to from a cleavage structure, where the combined melting temperature of the complementary regions within the 5' and 3' portions of the first oligonucleotide when annealed to the target nucleic acid is greater than the melting temperature of the 3' portion of the first oligonucleotide and cleavage of the cleavage structure occurs to generate labeled products; and (c) detecting the labeled cleavage products.

Thus, in an Invader assay, attachment of an e-tag to the 5' end of the detector sequence results in the formation of an e-tag-labeled nucleotide when the target sequence is present. The e-tag labeled nucleotide is separated and detected. By having a different e-tag for each nucleic acid sequence of interest, each having a different electrophoretic mobility, one can readily determine the SNPs or measure multiple sequences, which are present in a sample. The e-tags may require further treatment, depending on the total number of snps or target sequences being detected.

C. Fluorescent Quenching

If desired, the SNP detection e-tag probe may have a combination of a quencher and a fluorescer. In this instance the fluorescer would be in proximity to the nucleoside to which the linker is bonded, as well as the quencher, so that in the primer extension mixture, fluorescence from fluorescer bound to the SNP detection sequence would be quenched. As the reaction proceeds and fluorescer is released from the SNP detection sequence and, therefore, removed from the quencher, it would then be capable of fluorescence. By monitoring the primer extension mixture for fluorescence, one would be able to determine when there would probably be a sufficient amount of individual e-tags to provide a detectable signal for analysis. In this way, one could save time and reagent by terminating the primer extension reaction at the appropriate time. There are many quenchers that are not fluorescers, so as to minimize fluorescent background from the SNP detection sequence. Alternatively, one could take small aliquots and monitor the reaction for detectable e-tag reporters.

D. Analysis of Reaction Products

The separation of the e-tag reporters by electrophoresis can be performed in conventional ways. See, for example, U.S. Pat. Nos. 5,750,015, 5,866,345, 5,935,401, 6,103,199, and 6,110,343, and WO98/5269, and references cited therein. Also, the sample can be prepared for mass spectrometry in conventional ways. See, for example, U.S. Pat. Nos. 5,965,363, 6,043,031, 6,057,543, and 6,111,251.

After completion of the primer extension reaction, either by monitoring the change in fluorescence as described above or taking aliquots and assaying for total free e-tags, the mixture may now be analyzed. Depending on the instrument, today from one to four different fluorescers activated by the same light source and emitting at different detectable labels may be used. With improvements, five or more different fluorescers will be available, where an additional light source may be required. Electrochemical detection is described in U.S. Pat. No. 6,045,676.

The presence of each of the cleaved e-tags is determined by the label. The separation of the mixture of labeled e-tag reporters is typically carried out by electroseparation, which involves the separation of components in a liquid by application of an electric field, preferably, by electrokinesis (electrokinetic flow) electrophoretic flow, or electroosmotic flow, or combinations thereof, with the separation of the e-tag reporter mixture into individual fractions or bands. Electroseparation involves the migration and separation of molecules in an electric field based on differences in mobility. Various forms of electroseparation include, by way of example and not limitation, free zone electrophoresis, gel electrophoresis, isoelectric focusing and isotachophoresis. Capillary electroseparation involves electroseparation, preferably by electrokinetic flow, including electrophoretic, dielectrophoretic and/or electroosmotic flow, conducted in a tube or channel of about 1–200 micrometer, usually, about 10–100 micrometers cross-sectional dimensions. The capillary may be a long independent capillary tube or a channel in a wafer or film comprised of silicon, quartz, glass or plastic.

In capillary electroseparation, an aliquot of the reaction mixture containing the e-tag products is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

For a homogeneous assay, the sample, e-tag-labeled probe mixture, and ancillary reagents are combined in a reaction mixture supporting the cleavage of the linking region. The mixture may be processed to separate the e-tag reporters from the other components of the mixture. The mixture, with or without e-tag reporter enrichment, may then be transferred to an electrophoresis device, usually a microfluidic or capillary electrophoresis device and the medium modified as required for the electrophoretic separation. Where one wishes to remove from the separation channel intact e-tag reporter molecules, a ligand is bound to the e-tag that is not released when the e-tag reporter is released. Alternatively, by adding a reciprocal binding member that has the opposite charge of the e-tag reporter, so that the overall charge is opposite to the charge of the e-tag reporter, these molecules will migrate toward the opposite electrode from the released e-tag reporter molecules. For example, one could use biotin and streptavidin, where streptavidin carries a positive charge. In the case of an oligonucleotide, the e-tag reporter would be bonded to at least two nucleotides, where cleavage occurs between the two nucleotides with release of the e-tag reporter, with the terminal nucleotide of the dinucleotide labeled with a biotin (the e-tag reporter would be released without the biotinylated nucleotide). In the case of a peptide analyte, one would have cleavage at a site, where the ligand remains with the peptide analyte. For example, one could have the e-tag reporter substituted for the methyl group of methionine. Using the pyrazolone of the modified methionine, one could bond to an available lysine. The amino group of the pyrazolone would be substituted with biotin. Cleavage would then be achieved with cyanogen bromide, releasing the e-tag reporter, but the biotin would remain with the peptide and any e-tag that was not released from the binding member. Avidin is then used to change the polarity or sequester the e-tag reporter conjugated to the binding compound or target-binding moiety.

Capillary devices are known for carrying out amplification reactions such as PCR. See, for example, Analytical Chemistry (1996) 68:4081–4086. Devices are also known that provide functional integration of PCR amplification and capillary electrophoresis in a microfabricated DNA analysis device. One such device is described by Woolley, et al., in Anal. Chem. (1996) 68:4081–4086. The device provides a microfabricated silicon PCR reactor and glass capillary electrophoresis chips. In the device a PCR chamber and a capillary electrophoresis chip are directly linked through a photolithographically fabricated channel filled with a sieving matrix such as hydroxyethylcellulose. Electrophoretic injection directly from the PCR chamber through the cross injection channel is used as an "electrophoretic valve" to couple the PCR and capillary electrophoresis devices on a chip.

The capillary electrophoresis chip contains a sufficient number of main or secondary electrophoretic channels to receive the desired number of aliquots from the PCR reaction medium or the solutions containing the cleaved labels, etc., at the intervals chosen.

For capillary electrophoresis one may employ one or more detection zones to detect the separated cleaved labels. It is, of course, within the purview of the present invention to utilize several detection zones depending on the nature of the amplification process, the number of cycles for which a measurement is to be made and so forth. There may be any number of detection zones associated with a single channel or with multiple channels. Suitable detectors for use in the detection zones include, by way of example, photomultiplier tubes, photodiodes, photodiode arrays, avalanche photodiodes, linear and array charge coupled device (CCD) chips, CCD camera modules, spectrofluorometers, and the like. Excitation sources include, for example, filtered lamps, LED's, laser diodes, gas, liquid and solid-state lasers, and so forth. The detection may be laser scanned excitation, CCD camera detection, coaxial fiber optics, confocal back or forward fluorescence detection in single or array configurations, and the like.

Detection may be by any of the known methods associated with the analysis of capillary electrophoresis columns including the methods shown in U.S. Pat. Nos. 5,560,811 (column 11, lines 19–30), 4,675,300, 4,274,240 and 5,324, 401, the relevant disclosures of which are incorporated herein by reference.

Those skilled in the electrophoresis arts will recognize a wide range of electric potentials or field strengths may be used, for example, fields of 10 to 1000 V/cm are used with 200–600 V/cm being more typical. The upper voltage limit for commercial systems is 30 kV, with a capillary length of 40–60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from 180 to 1500 nm, usually 220 to 800 nm, more usually 450 to 700 nm, to have low transmission losses. Suitable materials include fused silica, plastics, quartz, glass, and so forth.

IV. Systems for Use of the e-tag Technology

Figure 16:
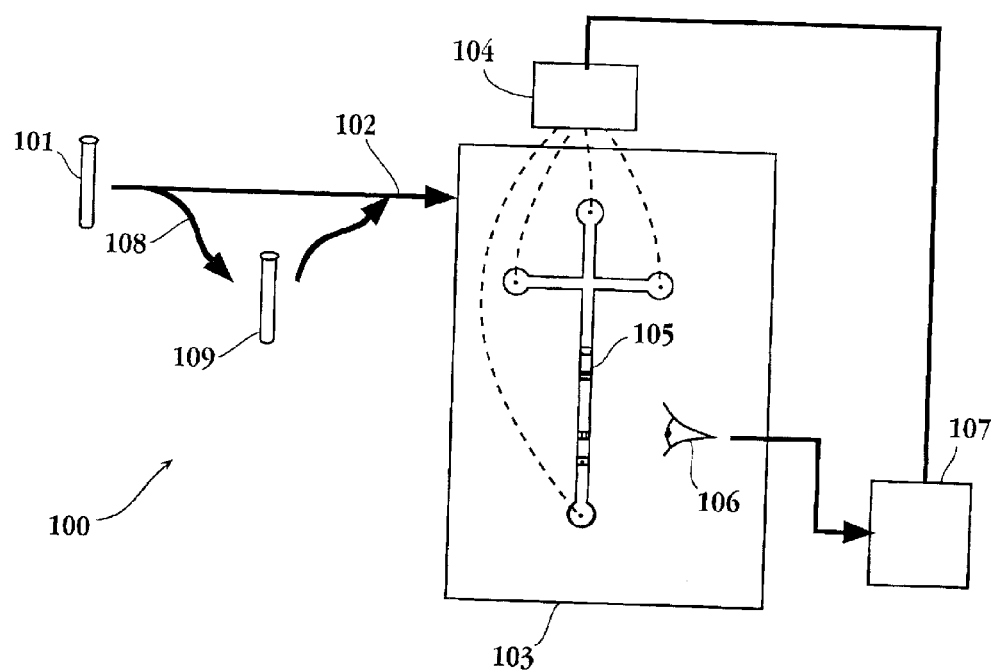
FIG. 16 is a diagram of a system for performing multiplexed determinations using e-tags.
Figure 17A:
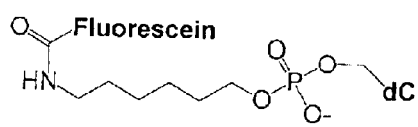
FIGS. 17A–J shows the structures of numerous exemplary e-tag reporters.
Figure 17A:
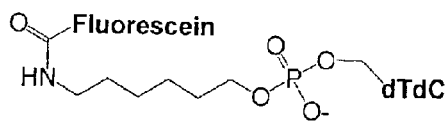
Figure 17A:
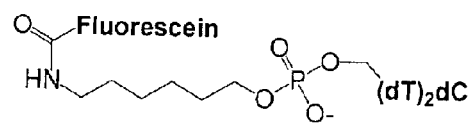
Figure 17A:
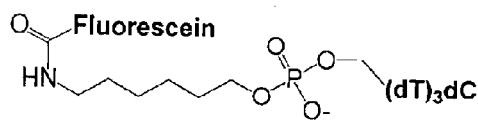
Figure 17A:
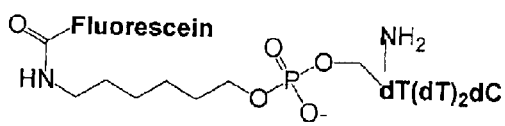
Figure 17A:
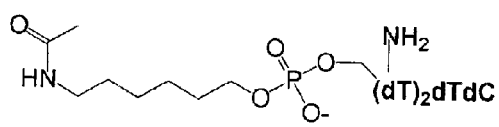
Figure 17A:
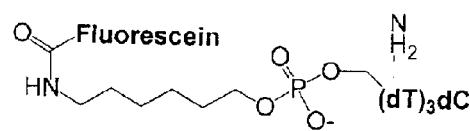
Figure 17A:
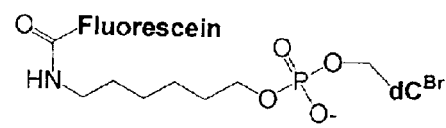
Figure 17A:
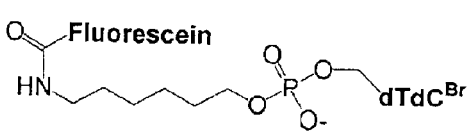
Figure 17A:
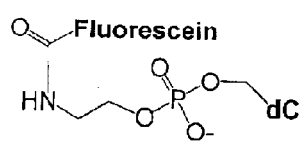
Figure 17A:
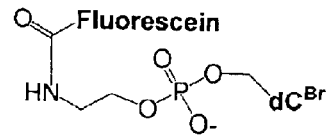
Figure 17A:
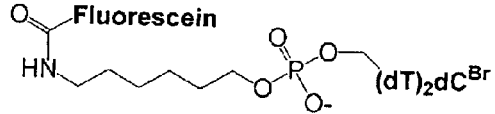
Figure 17B:
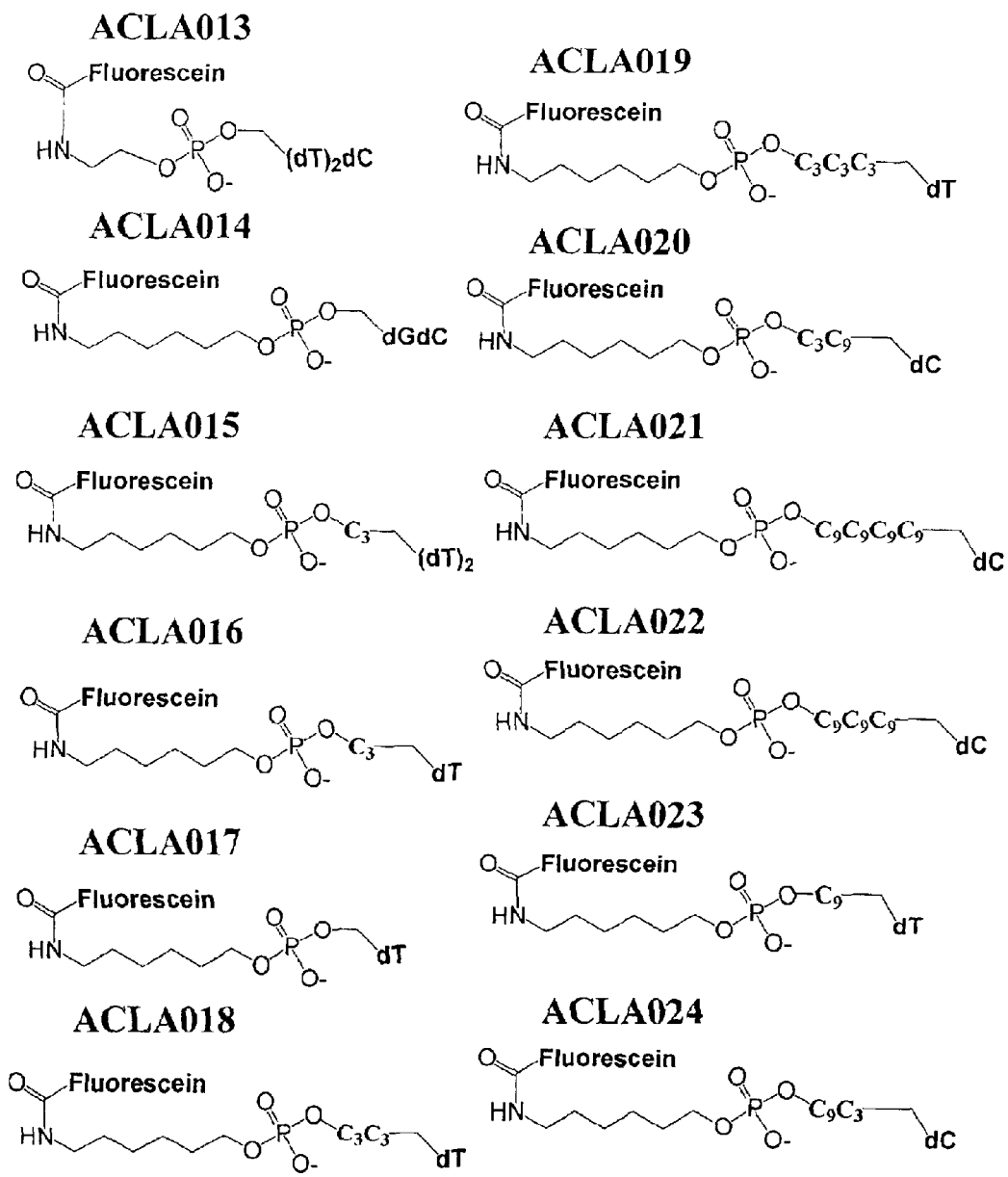
Figure 17C:
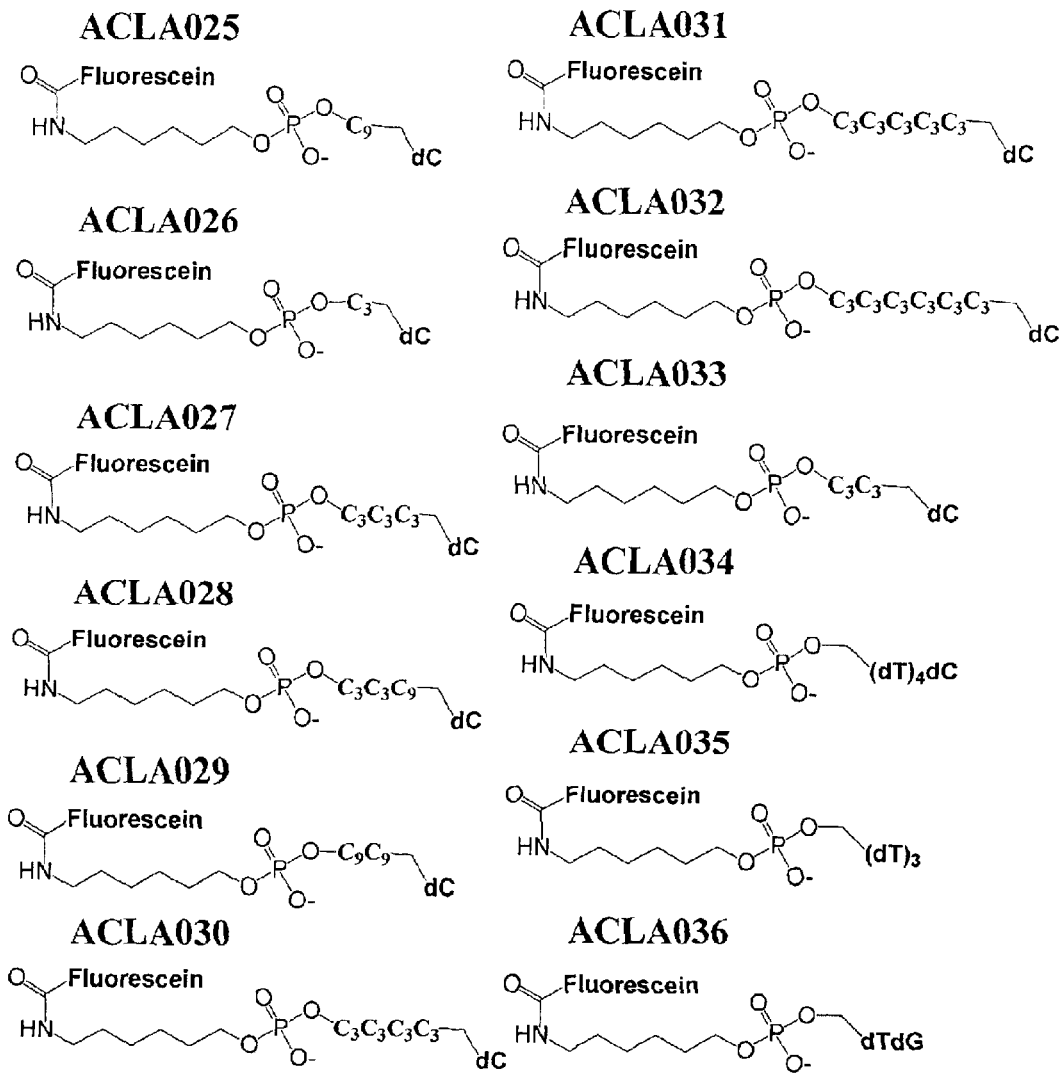
Figure 17D:
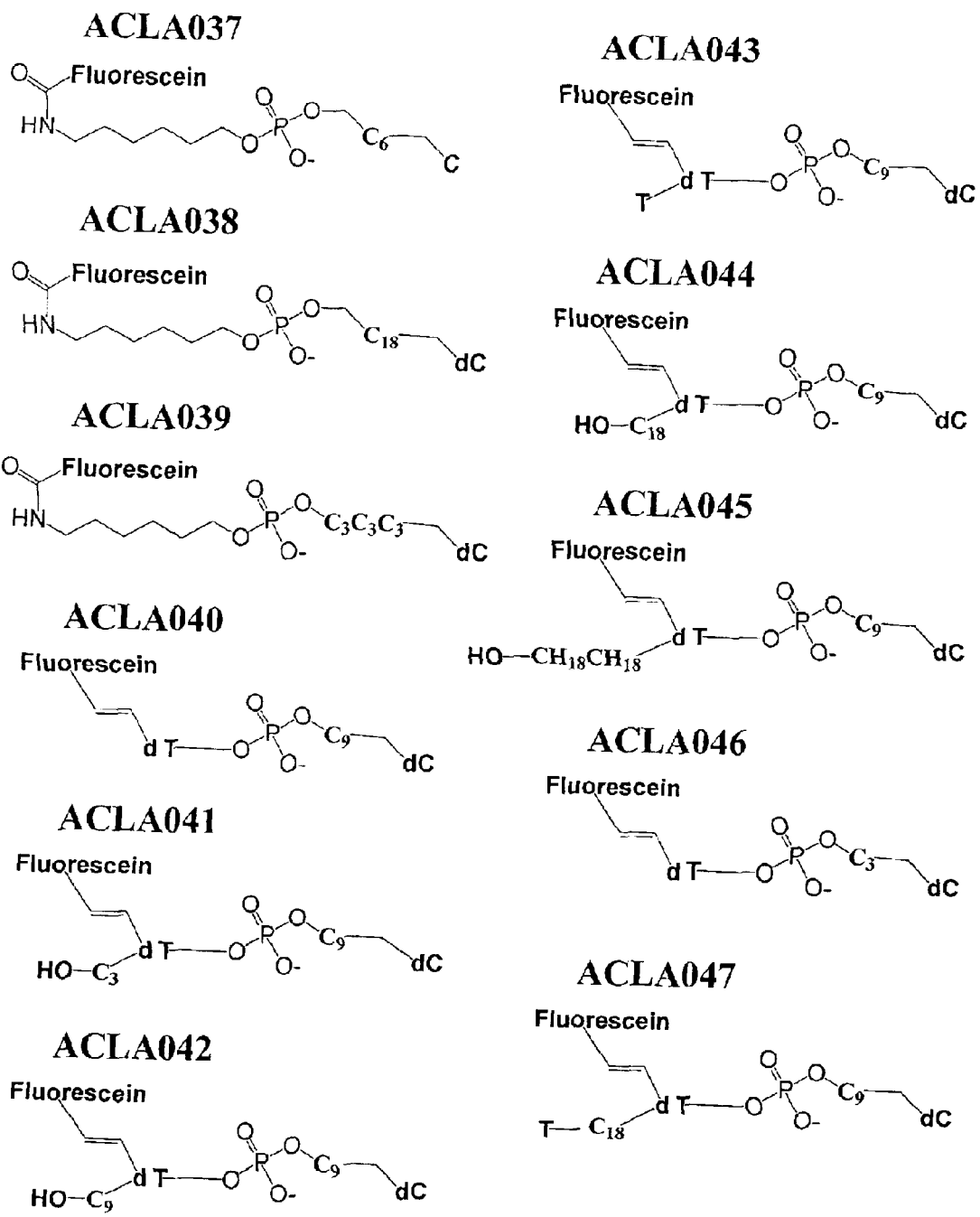
Figure 17E:
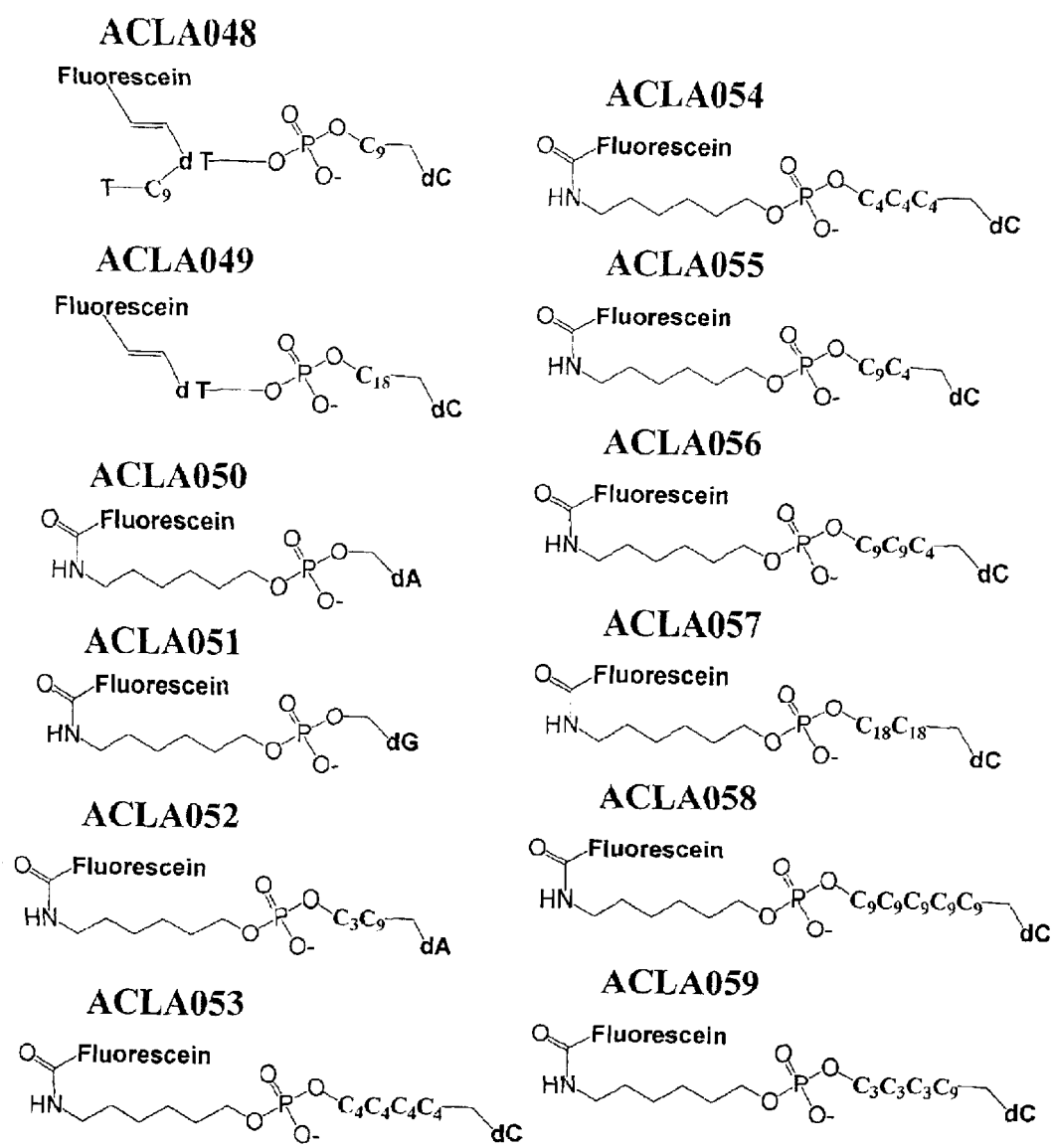
Figure 17F:
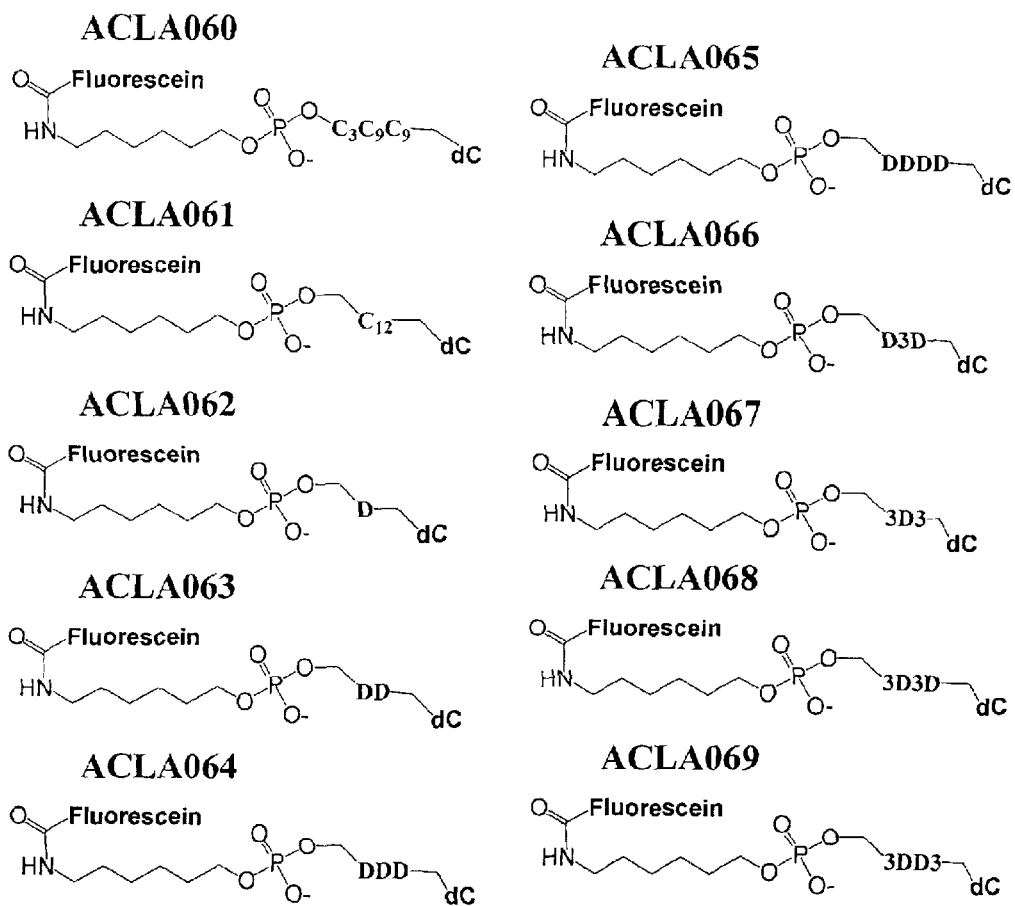
Figure 17G:
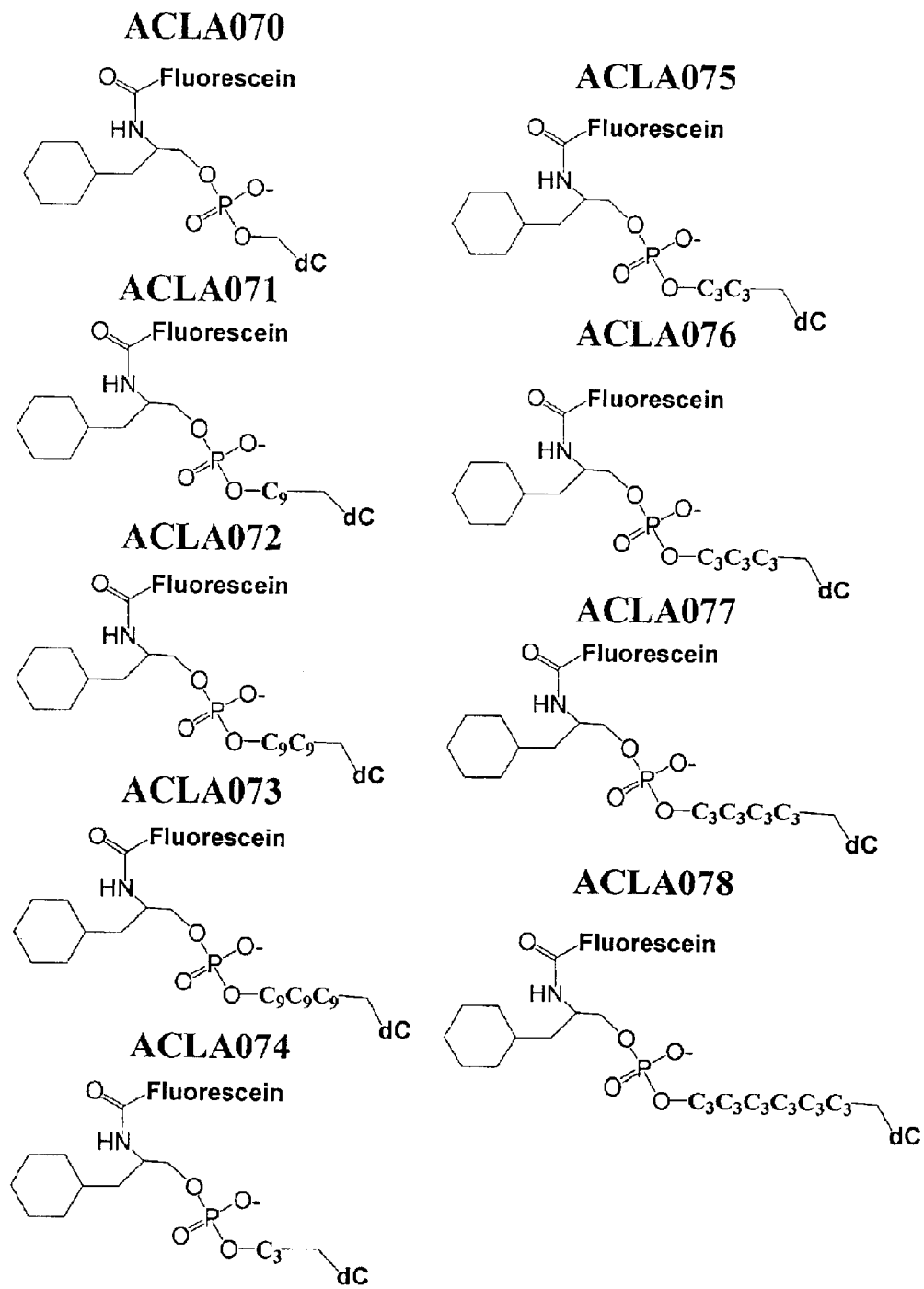
Figure 17H:
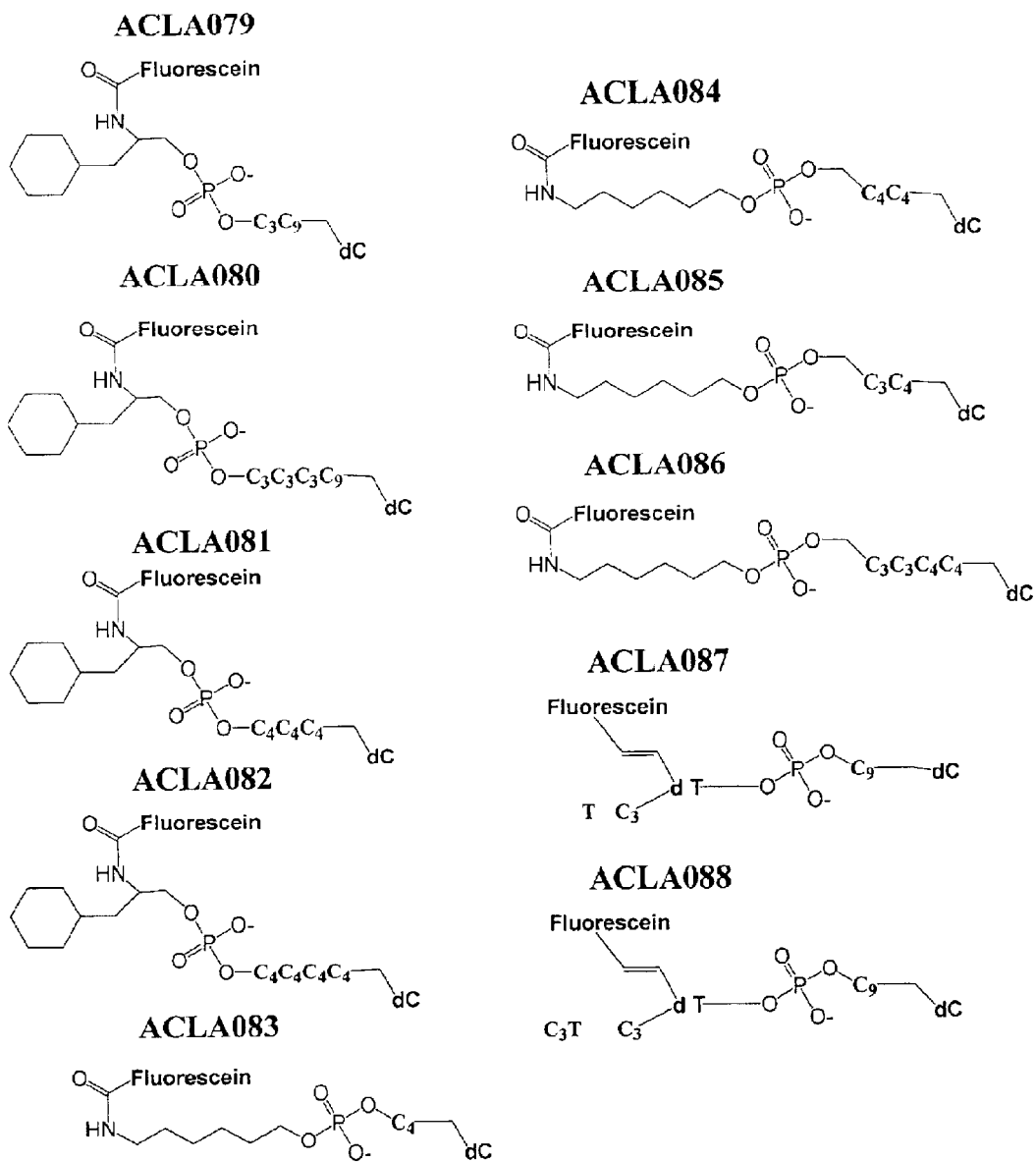
Figure 17I:
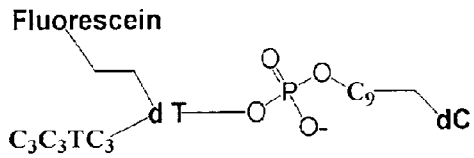
Figure 17I:
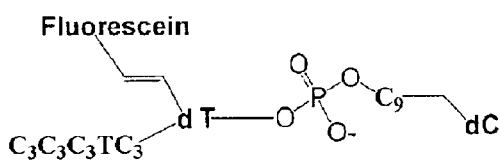
Figure 17I:
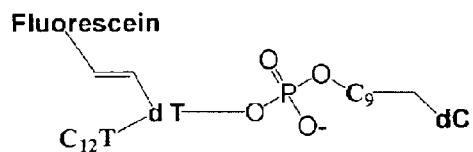
Figure 17I:
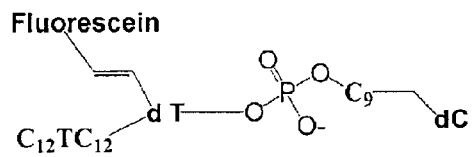
Figure 17I:
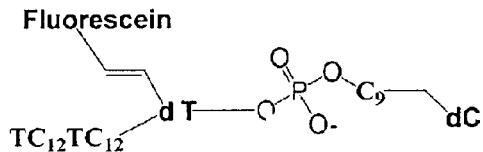
Figure 17I:
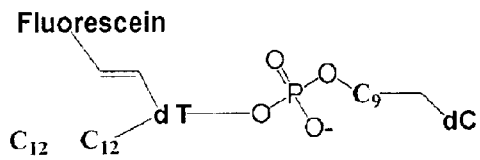
Figure 17I:
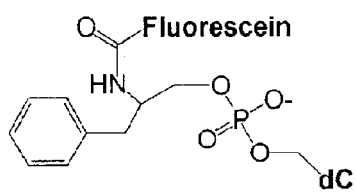
Figure 17I:
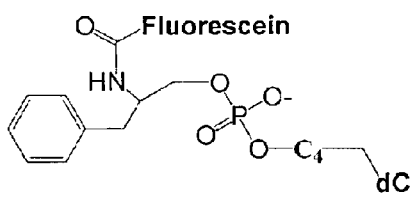
Figure 17I:
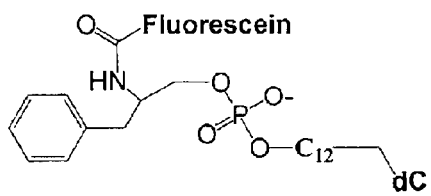
Figure 17J:
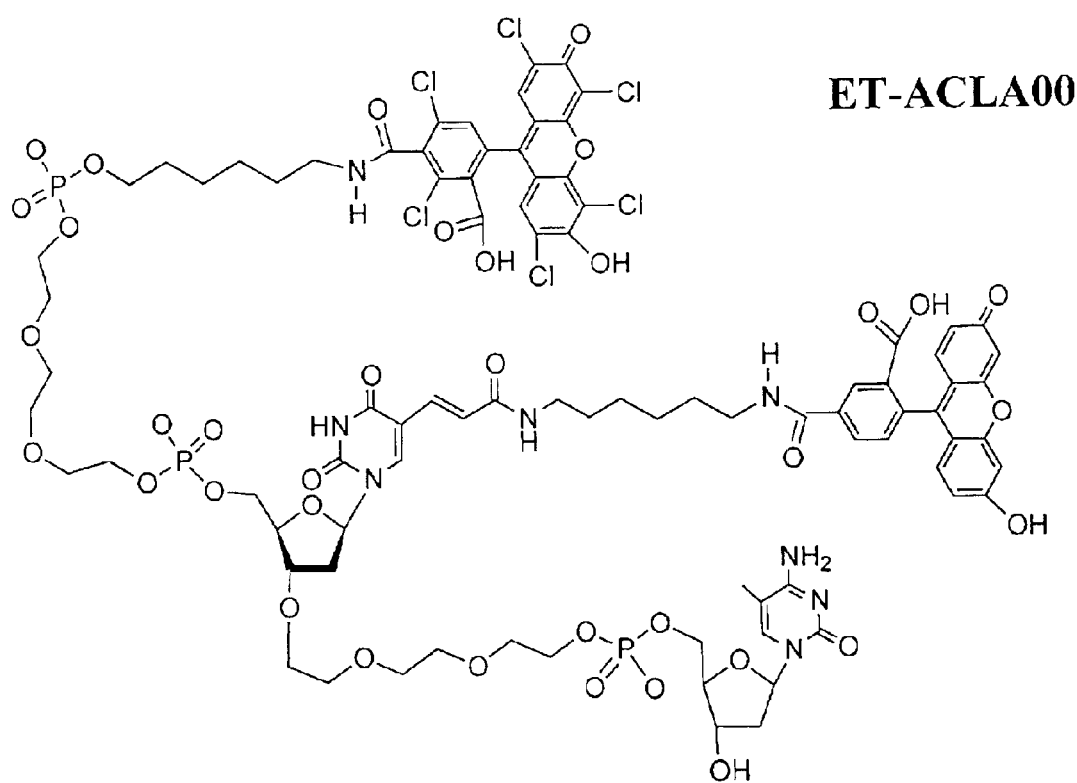

One embodiment of a system according to the present invention is presented in FIG. 16. This figure illustrates a system 100 for the simultaneous, multiplexed determination of a plurality of events. Each event is distinguished from the others by electrophoresis. For example, a snp locus may be characterized using a pair of reagents, each specific for one allele of the locus. Each reagent is bonded to an e-tag with a unique electrophoretic mobility and an associated label. When the reagent is combined with a sample of interest in a reaction vessel 101, the associated e-tag is modified in a manner that changes its electrophoretic mobility if its specific target is present. After the reaction, the mixture is moved 102 onto an electrophoretic device 103 for separation of the e-tag reporter products contained in the mixture. A power control box 104 is used in conjunction with the device to control injection of the sample into the separation channel 105. Each e-tag reporter species migrates down the separation channel of the device with a mobility unique to that tag, moving past a detector 106 that monitors its presence by its associated label. The data collected by the detector is sent to a data processor 107, which determines the presence of each snp allele in the sample based on the mobility of its corresponding e-tag reporter.

In another example, a group of snp loci or other sequences may be monitored in a multiplexed reaction. In this case, a plurality of pairs of e-tag reagents corresponding to the target sequences are combined with a sample in a single reaction vessel under conditions where the e-tag reporter is released from at least a portion of the target oligonucleotide sequence to which it is bonded when a pair is bonded to its target. The e-tag reporters are either labeled for detection or the label is added by means of a reactive functionality present on the e-tag. The labeled e-tag products of the reaction are resolved from one another on the electrophoretic device, and again are monitored as they move past the detector. The level of multiplexing possible in this system is limited only by the degree of resolution that can be obtained between a designated set of e-tag reporters on the electrophoretic device.

An additional degree of flexibility can be conferred on the assay by the stage at which the e-tags are labeled. As described above, each e-tag may already contain a detectable label when introduced into the reaction. Alternatively, an e-tag may contain a functionality allowing it to bind to a label after reaction with the sample is complete (FIG. 16;

108). In this embodiment, an e-tag comprising a functionality for binding to a detectable label is combined with a sample (FIG. 16; 101). After a reaction to modify the mobility of the e-tag if its target is present in the sample, additional reagents are combined in a sample vessel (FIG. 16; 109) with the products of the first reaction, which will react with the modified e-tag(s) to add a detectable label.

V. Kits for use of the e-tag Technology

As a matter of convenience, predetermined amounts of reagents employed in the present invention can be provided in a kit in packaged combination. One exemplary kit for snp detection can comprise in packaged combination an oligonucleotide primer for each polynucleotide suspected of being in said set wherein each of said primers is hybridizable to a first sequence of a respective polynucleotide if present, a template dependent polynucleotide polymerase, nucleoside triphosphates, and a set of primer and oligonucleotide snp detection sequences, each of the snp detection sequences having a fluorescent label at its 5'-end and having a sequence at its 5'-end that is hybridizable to a respective polynucleotide wherein each of the electrophoretic labels is cleavable from the snp detection sequence.

The kit may further comprise a device for conducting capillary electrophoresis as well as a template dependent polynucleotide polymerase having 5' to 3' exonuclease activity. The kit can further include various buffered media, some of which may contain one or more of the above reagents.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. For example, the dNTPs, the oligonucleotide pairs, optionally the polymerase, may be included in a single container, which may also include an appropriate amount of buffer. The kits may also include a written description of a method in accordance with the present invention as described above.

In one embodiment of the kit, the electrophoretic tags are fluorescent conjugates represented by the formula:

R-L-T$^a$ wherein R is a fluorescer, L is a linking group, as described previously, and T$^a$ is a functionality for binding to a nucleoside base, purine or pyrimidine, or a nucleoside base, a nucleoside, nucleotide or nucleotide triphosphate.

In another embodiment of a kit, the electrophoretic tags are fluorescent conjugates represented by the formula:

R'-L'-T$^b$ wherein R' is a fluorescer, L' is a bond an amino acid or a peptide or combinations of amino acids and thioacids or other carboxylic acids and T$^b$ is a nucleotide or nucleotide triphosphate.

In another embodiment of a kit, the electrophoretic tag is a fluorescent conjugate represented by the formula:

Fluorescer-L''-(amino acid)$_n$-T$^c$ wherein L'' is a bond or a linking group of from 1 to 20 atoms in the chain and n is 1 to 100. The fluorescer may be fluorescein, the amino acid may be lysine and L'' may be a bond in the form of an amide linkage involving the meta-carboxyl of the fluorescein and the terminal amine group of lysine, and T$^c$ is the OH of the carboxyl of the last amino acid, a moiety of from 0 to 6 carbon atoms for linking the carboxy to a nucleoside, nucleotide or nucleotide triphosphate.

In another embodiment of a kit in accordance with the invention, the electrophoretic tag is a label conjugate represented by the formula:

Fluorescein-(CO)NH—CH(CH$_2$)$_3$CH(NH$_2$)COX wherein X is selected from the group consisting of: OH, NH-lysine, NH-(lysine)$_2$, NH-alanine, NH-aspartic acid, NH-(aspartic acid)$_2$, NH-(aspartic acid)$_3$, NH-(aspartic acid)$_4$, NH-(aspartic acid)$_5$, NH-(aspartic acid)$_6$, NH-(aspartic acid)$_7$, NH-alanine-lysine, NH-aspartic acid-lysine, NH-(aspartic acid)$_2$-lysine, NH-(aspartic acid)$_3$-lysine, NH-(aspartic acid)$_4$-lysine, NH-(aspartic acid)$_5$-lysine, NH-(aspartic acid)$_6$-lysine, NH-(aspartic acid)$_7$-lysine, NH-(aspartic acid)$_8$-lysine, NH-(lysine)$_4$, and NH-(lysine)$_5$ The terminal carboxy may be linked to T$^c$.

The e-tags described above may terminate in an appropriate functionality for linking to a nucleotide, nucleotide triphosphate, or other molecule of interest, or may terminate in such moieties.

For convenience, kits can be provided comprising building blocks for preparation of eTags in situ or have assembled eTags for direct bonding to the binding compound. For preparing the eTags in situ during the synthesis of oligonucleotides, one would provide phosphoramidites or phosphates, where the esters would include alkyl groups, particularly of from 1 to 3 carbon atoms, and cyanoethyl groups, while for the phosphoramidite, dialkylamino, where the alkyl groups are of from 1–4 carbon atoms, while the other group would be a protected hydroxy, where the protecting group would be common to oligonucleotide synthesis, e.g. dimethoxytrityl. For large numbers of eTag probes, that is, 20 or more, one kit would supply at least 3 each of mass-modifying regions and charge-modifying regions, each having at least the phosphate linking group and a protected hydroxyl. The two functional groups may be separated by 2 or more atoms, usually not more than about 60 atoms, and may be vicinal ($\alpha,\beta$ to $\alpha,\omega$). The nature of the compounds has been discussed previously. In the simplest case, the phosphorous acid derivative would serve as the charge-modifying region, so that the mass-modifying region and the charge-modifying region would be added as a single group. In addition, one would have at least 2 detectable regions, which would be a fluorescer having the phosphate linker and other functionalities protected for purposes of the synthesis. Alternatively, instead of having the detection region the terminal region, where the detectable region allows for the presence of two functionalities that can be used for linking, one of the other regions may serve as the terminal region. Also, one of the regions may be conveniently linked to a mono- or dinucleotide for direct linking to the oligonucleotide chain, where cleavage will occur at the 3' site of the nucleotide attached to the e-tag reporter. By using tri- or tetra-substituted groups, one can provide a detectable region that provides the pair for energy transfer. One need only have one or two different energy transfer agents, while having a plurality of emitting agents to greatly expand the number of different e-tag reporters.

Where one prepares the e-tag probe, there will be the additional linking region, which in the above description is served by the phosphorous acid derivative or the mono- or dinucleotide unit phosphorous acid derivative. For these e-tag probes, one need not be restricted to phosphate links, but may use other convenient chemistries, particularly chemistries that are automated. Thus, instead of phosphorous acid and protected alcohol, one can use carboxy and alcohol or amino, activated olefin and thiol, amino and oxo-carbonyl, particularly with reductive amination, an hydroxy with an active halide or another hydroxy to form an ether, and the like. One may employ compounds that are di-functional, with the same or different functionalities, where one could have a diacid and a diol or a hydroxy acid or cyclic ester for producing the e-tag probe. Numerous examples of these types of compounds have already been described and are well known in the literature. By appropriate selection of the monomers and conditions, one can select a particular order of reaction, namely the number of monomers that react or one may separate the mixture by the different mobilities.

The kits will include at least two detectable regions and sufficient reagents to have at least 10, usually at least 20 and frequently at least 50 or more different e-tag reporters that can be separated by their mobility.

The kits will usually have at least about 5 different e-tags for conjugation, more usually at least about 10, frequently at least about 25 and may have 50 or more, usually not more than about 1,000. The e-tags will differ as to mobility, including mass/charge ratio and nature of charge, e.g. overall positive or negative, detectable moiety, e.g. fluorophor, electrochemical, etc, or functionality for linking a detectable moiety, e.g. maleimide, mercaptan, aldehyde, ketone, etc.

EXAMPLES

The invention is demonstrated further by the following illustrative examples. Parts and percentages are by weight unless otherwise indicated. Temperatures are in degrees Centigrade (° C.) unless otherwise specified. The following preparations and examples illustrate the invention but are not intended to limit its scope. Unless otherwise indicated, oligonucleotides and peptides used in the following examples were prepared by synthesis using an automated synthesizer and were purified by gel electrophoresis or HPLC.

The following abbreviations have the meanings set forth below:
Tris HCl—Tris(hydroxymethyl)aminomethane-HCl (a 10×solution) from BioWhittaker, Walkersville, Md.
HPLC—high performance liquid chromatography
BSA—bovine serum albumin from Sigma Chemical Company, St. Louis Mo.
EDTA—ethylene diamine tetra-acetate from Sigma Chemical Company
bp—base pairs
g—grams
mM—millimolar
TET—tetrachlorofluorescein
FAM—fluorescein
TAMRA—tetramethyl rhodamine
EOF—electroosmotic flow
Reagents
TET and TAMRA were purchased from Perkin Elmer (Foster City, Calif.) as were conjugates of TET, FAM and TAMRA with oligonucleotides.
Master Mix (2×): 20 mM Tris-HCl, 2.0 mM EDTA, pH 8.0 (8% Glycerol), 10 mM $MgCl_2$, dATP 400 $\mu M$,
dCTP 400 $\mu M$, dGTP 400 $\mu M$, dUTP 400 $\mu M$, AmpliTaq Gold® 0.1 U/$\mu L$ (from Perkin Elmer), Amperase UNG® 0.02 U/$\mu L$ (from Perkin Elmer)
Probes and Primers: (10×)
Forward Primer: 3.5 $\mu M$ 5'-TCA CCA CAT CCC AGT G-3' (SEQ ID NO:1)
Reverse Primer: 2.0 $\mu M$ 5'-GAG GGA GGTTTG GCTG-3' (SEQ ID NO:2)
Plasmid Allele 1 Probe: 2.0 $\mu M$ (200 $\mu M$ per reaction) 5' TET-CCA GCA ACC AAT GAT GCC CGT T-TAMRA-3' (SEQ ID NO:3)
Plasmid Allele 2 Probe: 2.0 $\mu M$ (200 nM per reaction) 5' FAM-CCA GCA AGC ACT GAT GCC TGT T-TAMRA-3' (SEQ ID NO:4)
Target DNA:
Plasmid Allele-1: 10 fg/$\mu L$=approximately 1000 copies/$\mu L$
Plasmid Allele-2: 10 fg/$\mu L$=approximately 1000 copies/$\mu L$
Synthesis of Elements of e-tag Probes
A. Synthesis of 6-Carboxyfluorescein Phosphoramidite Derivatives To a solution of 6-carboxyfluorescein (0.5 g, 1.32 mmol) in dry pyridine (5 mL) was added drop wise, isobutyric anhydride (0.55 mL, 3.3 mmol). The reaction was allowed to stir at room temperature under an atmosphere of nitrogen for 3 h. After removal of pyridine in vacuo the residue was redissolved in ethyl acetate (150 mL) and washed with water (150 mL). The organic layer was separated, dried over $Na_2SO_4$, filtered, and concentrated in vacuo to yield a brownish residue. This material was dissolved in $CH_2Cl_2$ (5 mL) after which N-hydroxy succinimide (0.23 g, 2.0 mmol) and dicyclohexylcarbodiimide (0.41 g, 1.32 mmol) were added. The reaction was allowed to stir at room temperature for 3 h and then filtered through a fritted funnel to remove the white solid, which had formed. To the filtrate was added aminoethanol (0.12 mL, 2.0 mmol) dissolved in 1 mL of $CH_2Cl_2$. After 3 h the reaction was again filtered to remove a solid that had formed, and then diluted with additional $CH_2Cl_2$ (50 mL). The solution was washed with water (150 mL) and then separated. The organic layer was dried over $Na_2SO_4$, filtered, and concentrated in vacuo to yield a white foam (0.7 g, 95%, 3 steps). $^1H$ NMR: (DMSO), 8.68 (t, 1H), 8.21 (d, 1H), 8.14 (d, 1H), 7.83 (s, 1H), 7.31 (s, 2H), 6.95 (s, 4H), 4.69 (t, 1H), 3.45 (q, 2H), 3.25 (q, 2H), 2.84 (h, 2H), 1.25 (d, 12 H). Mass (LR FAB$^+$) calculated for $C_{31}H_{29}NO_9$ (M+H$^+$) 559.2, found: 560.

B. Synthesis of Modified Fluorescein Phosphoramidites

Pivaloyl protected carboxyfluorescein: Into a 50 mL round bottom flask was placed 5(6)-carboxyfluorescein (0.94 g, 2.5 mmol), potassium carbonate (1.0 g, 7.5 mmol) and 20 mL of dry DMF. The reaction was stirred under nitrogen for 10 min, after which trimethylacetic anhydride (1.1 mL, 5.5 mmol) was added via syringe. The reaction was stirred at room temperature overnight, and then filtered to remove excess potassium carbonate and finally poured into 50 mL of 10% HCl. A sticky yellow solid precipitated out of solution. The aqueous solution was decanted off and the residual solid was dissolved in 10 mL of methanol. Drop wise addition of this solution to 10% HCl yielded a fine yellow precipitate, which was filtered and air dried to yield an off white solid (0.88 g, 62%). TLC (45:45:10 of Hxn:EtOAc:MeOH).

NHS ester of protected pivaloyl carboxyfluorescein. Into a 200 mL round bottom flask was placed the protected carboxyfluorescein (2.77 g, 5.1 mmol) and 50 mL of dichloromethane. N-hydroxysuccinimide (0.88 g, 7.6 mmol) and dicyclohexylcarbodiimide (1.57 g, 7.6 mmol) were added and the reaction was stirred at room temperature for 3 hours. The reaction was then filtered to remove the precipitated dicyclohexyl urea byproduct and reduced to approx. 10 mL of solvent in vacuo. Drop wise addition of hexanes with cooling produced a yellow-orange colored solid, which was triturated with hexanes, filtered and air-dried to yield 3.17 g (95%) of product. TLC (45:45:10 of Hxn:EtOAc:MeOH)

Alcohol. Into a 100 mL round bottom flask was placed the NHS ester (0.86 g, 1.34 mmol) and 25 mL of dichloromethane. The solution was stirred under nitrogen after which aminoethanol (81 mL, 1eq) was added via syringe. The reaction was monitored by TLC (45:45:10 Hxn,EtOAc, MeOH) and was found to be complete after 10 min. The dichloromethane was then removed in vacuo and the residue dissolved in EtOAc, filtered and absorbed onto 1 g of silica gel. This was bedded onto a 50 g silica column and eluted with Hxn:EtOAc:MeOH (9:9:1) to give 125 mg (20%) of clean product.

Phosphoramidite. Into a 10 mL round bottom flask containing 125 mg of the alcohol was added 5 mL of dichloromethane. Diisopropyl ethylamine (139 µL, 0.8 mmol) was added via syringe. The colorless solution turned bright yellow. 2-cyanoethyl diisopropylchlorophosphoramidite (81 µL, 0.34 mmol) was added via syringe and the solution immediately went colorless. After 1 hour TLC (45:45:10 of Hxn:EtOAc:TEA) showed the reaction was complete with the formation of two closely eluting isomers. Material was purified on a silica column (45:45:10 of Hxn:EtOAc:TEA) isolating both isomers together and yielding 130 mg (85%).

Carboxylic acid. Into a 4 mL vial was placed 12-aminododecanoic acid (0.1 g, 0.5 mmol) and 2 mL of pyridine. To this suspension was added chlorotrimethyl silane (69 µL, 1.1 eq) via syringe. After all material dissolved (10 min) NHS ester (210 mg, 0.66 eq) was added. The reaction was stirred at room temperature overnight and then poured into water to precipitate a yellow solid, which was filtered, washed with water, and air-dried. TLC (45:45:10 of Hxn:EtOAc:MeOH) shows a mixture of two isomers.

General Procedure for Remaining Syntheses. The carboxylic acid formed as described above is activated by NHS ester formation with 1.5 eq each of N-hydroxysuccinimide and dicyclohexylcarbodiimide in dichloromethane. After filtration of the resulting dicyclohexylurea, treatment with 1 eq of varying amino alcohols will effect amide bond formation and result in a terminal alcohol. Phosphitylation using standard conditions described above will provide the phosphoramidite.

Figure 33:
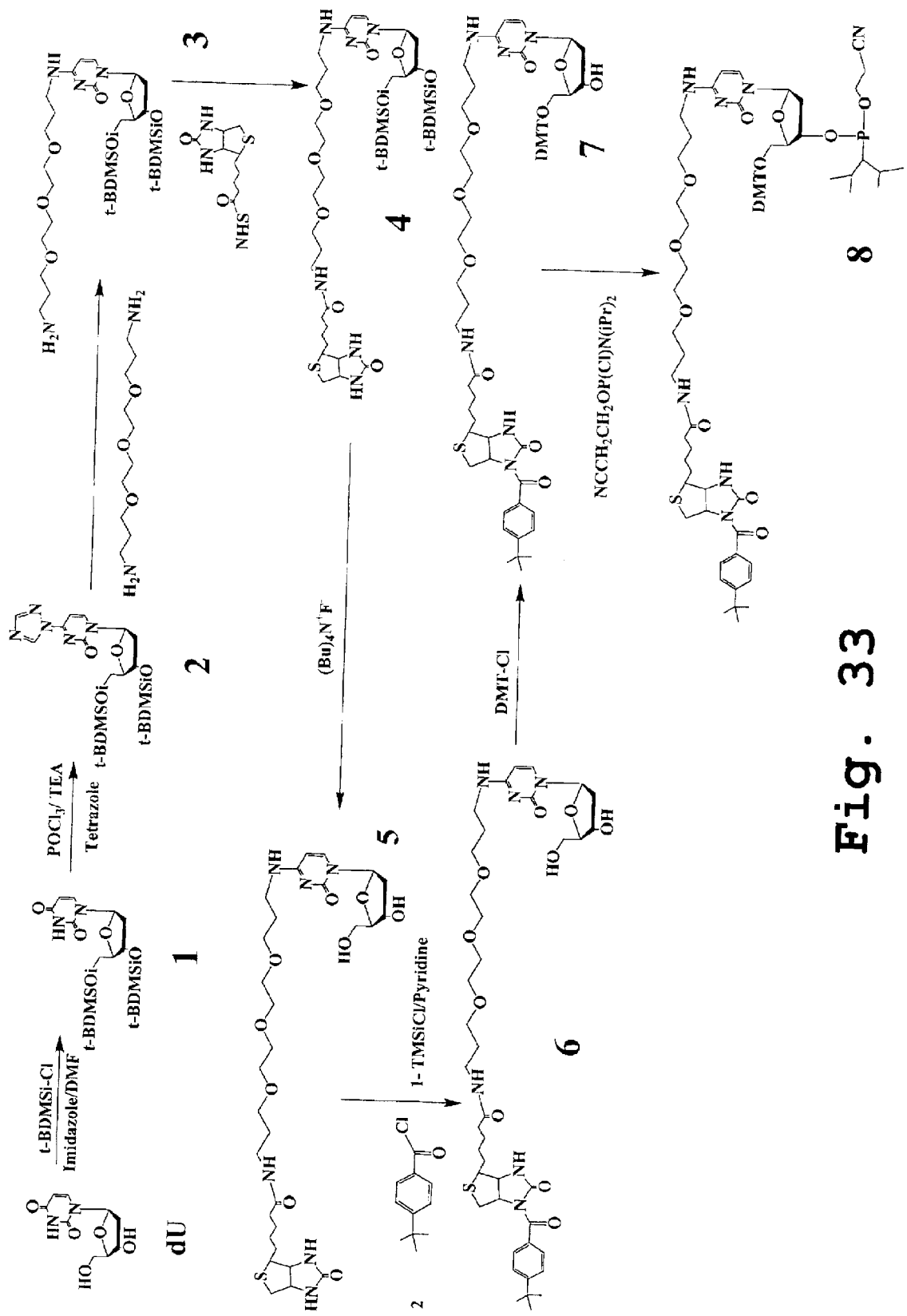
FIG. 33 is a schematic diagram of the steps involved in the synthesis of the phosphoroamidite of biotin-deoxycytosine (dC) (Reagent C).

C. Synthesis of Biotinylated 2'-Deoxycytosine Phosphoramidite (FIG. 33)

Compound 1

Synthesis of 3',5'-O-di-t-butyldimethylsilyl-2'-Deoxyuridine(1)

2'-deoxyuridine (4 gm, 17.5 mmol) and imidazole (3.47 gm, 52.5 mmol) were dissolved in 30 ml of dry DMF and t-butyldimethyl-silyl chloride (7.87 gm, 52.5 mmol) added to the stirring solution at room temperature. After 3 hrs, TLC on silica gel (10% MeOH +90% $CH_2Cl_2$) showed that all starting material had been converted to a new compound with higher Rf. The solution was concentrated into a small volume; about 200 ml of ether was then added and washed three times with saturated aqueous NaCl solution. The organic layer was dried over anhydrous $Na_2SO_4$, and the filtrate was evaporated to give a colorless gummy material that converted to a white solid product (eight gm, 100%). This product was identified with HNMR and ES-MS.

Compound 2

Synthesis of 3', 5'-O-di-t-butyldimethylsilyl-$N^4$-(1,2,4-triazolo)-2'-Deoxycytidine 1,2,4-Triazole (19.45 gm, 282 mmol) was suspended in 300 ml of anhydrous $CH_3CN$ at 0° C., 8 ml of $POCl_3$, then 50 ml of triethylamine was added slowly in 5 min. After an hour, 3',5'-O-di-t-butyldimethylsilyl-2'-deoxyuridine (Compound 1) (9 gm, 19.7 mmol) was dissolved in 200 ml of dry $CH_3CN$ and added to the reaction over 20 min. After stirring the reaction for 16 hours at RT, TLC (100% ether) showed that all starting material was converted to a new compound with lower Rf. The reaction mixture was filtered, reduced the volume of $CH_3CN$, diluted with ethyl acetate and washed with saturated aqueous $NaHCO_3$ then twice with saturated aqueous NaCl. The organic layer was dried over anhydrous $Na_2SO_4$ and the solvent was evaporated, co-evaporated from toluene to give a yellow solid product (10 gm, 100%). This product was identified with HNMR and ES-MS.

Compound 3

Synthesis of 3',5'-O-di-t-butyldimethylsilyl-$N^4$-(4,7,10-trioxa-1-tridecaneamino)-2'-deoxycytidine 4,7,10-Trioxa-1,13-tridecanediamine (10.44 gm, 47.4 mmol) was dissolved in 100 ml dioxane, then 3',5'-O-di-t-butyldimethylsilyl-4-(1,2,4-triazolo)-2'-deoxycytidine (Compound 2) (8.03 gm, 15.8 mmol) was dissolved in 200 ml of dioxane (heated to about 50 C and cooling it dawn to RT) and added drop wise in 10 min, to the solution of 4,7,10-Trioxa-1,13-tridecanediamine with vigorous stirring at RT. After 5 hrs, TLC on silica gel showed that all starting material was converted to a new product with lower Rf, the resulting mixture was evaporated to dryness. The residue was dissolved in dichloromethane and washed twice with 5% sodium bicarbonate solution and saturated sodium chloride solution. The organic layer was dried over sodium sulphate, filtered and evaporated to dryness to give a yellow gummy product (7.87 gm). The product was purified on a silica gel column eluted with a gradient of 0 to 10% methanol in dichloromethane with 1% triethylamine. The product was obtained as a yellowish gum (5.66 gm, 54%). This product was identified with HNMR and ES-MS.

Compound 4

Synthesis of 3',5'-O-di-t-butvldimethylsilyl-4-N-(4,7,10-trioxa-1-tridecaneaminobiotin)-2'-deoxycytidine 3',5'-O-di-t-butyldimethylsilyl-4-N-(4,7,10-trioxa-1-tridecaneamino)-2'-deoxycytidine (Compound 3) (2.657 gm, 4.43 mmol) and Biotin-NHS ester (1.814 gm, 5.316 mmol) were dissolved in 20 mL of dry DMF and about 1 mL of triethylamine was added. After stirring the reaction mixture for 4 hrs at RT, the reaction was stopped by evaporating all DMF to give a yellow gum material (4.36 gm). This material was dissolved in dichloromethane and washed three times with saturated solution of NaCl, dried over sodium sulphate and evaporated to dryness. TLC on silica gel (5% MeOH+1% TEA+94% $CH_2Cl_2$) indicated the formation of a new product that was higher Rf. This product was purified with column chromatography on silica gel using (99% $CH_2Cl_2$+1% TEA) to (1% MeOH+1% TEA+98% $CH_2Cl_2$) to yield a yellow foamy product (2.13 gm, 60%). This product was identified with HNMR and ES-MS.

Compound 5

Synthesis of 4-N-(4,7,10-trioxa-1-tridecaneaminobiotin)-2'-deoxycytidine

3',5'-O-di-t-butyldimethylsilyl-4-N-(4,7,10-trioxa-1-tridecaneaminobiotin)-2'-deoxycytidine (Compound 4) (1.6 gm, 1.8 mmol) was dissolved in 50 mL of dry THF, then about 5.5 mL of tetrabutylammonium fluoride in THF was added in 2 min. while stirring at RT. After 3 hrs, TLC on silica gel (10% MeOH+1% TEA+89% $CH_2Cl_2$) showed that a new product with lower Rf formed. The solvent was evaporated to give a yellow oily product. Column chromatography on silica gel eluted with (99% $CH_2Cl_2$+1% TEA) to (7% MeOH+1% TEA+92% $CH_2Cl_2$) permitted the purification of the product as a gummy colorless product (1.14 gm, 97%). This product was identified with HNMR and ES-MS.

Compound 6 t-butylbenzoylation of the biotin of 4-N-(4,7,10-trioxa-1-tridecaneaminobiotin)-2'-deoxycytidine 4-N-(4,7,10-trioxa-1-tridecaneaminobiotin)-2'-deoxycytidine (Compound 5) (14.14 gm, 21.5 mmol) was dissolved in 100 mL of dry pyridine. Chlorotrimethyl silane (11.62 gm, 107.6 mmol) was added and the mixture was stirred for 2 hrs at RT. 4-t-butylbenzoyl chloride (5.07 gm, 25.8 mmol) was added and the mixture was stirred for another 2 hrs at RT. The reaction mixture was cooled with ice-bath and the reaction stopped by adding 50 ml of water and 50 ml of 28% aqueous ammonia solution. The solution kept stirring at RT for 20 min, then evaporated to dryness in high vacuum and finally co-evaporated twice from toluene. The material was dissolved in dichloromethane and extracted twice with 5% aqueous sodium bicarbonate solution. The organic layer was dried over sodium sulphate, evaporated to dryness, re-dissolved in dichloromethane and applied to a silica gel column. The column was eluted with gradient from 0 to 10% of methanol in dichloromethane and obtained a product as a white foam (9.4 gm, 53.5%). This product was identified with HNMR and ES-MS.

Compound 7

Synthesis of 5'-O-(4,4'-dimethoxytriphenylmethyl)-4-N-(4,7,10-trioxa-1-tridecaneaminobiotin)-2'-deoxycytidine Compound 6 (10.82 gm, 13.3 mmol) was co-evaporated twice from dry pyridine, then dissolved in pyridine (100 ml) and 4,4'-dimethoxytritylchloride(DMT-Cl) (6.76 gm, 19.95 mmol) was added and the resulting mixture stirred for 3 hrs. TLC (10% MeOH+1% TEA+89% $CH_2Cl_2$) showed the formation of new product with higher Rf, and some starting material remained unreacted, then another amount of DMTCl (2 gm) was added and kept stirring for 2 hrs. The reaction was stopped by adding ethanol, and the mixture was stirred for 15 min. After evaporation to dryness and co-evaporation from toluene, the material was dissolved in dichloromethane. The organic layer was washed twice with 5% aqueous sodium bicarbonate solution, dried over sodium sulphate and evaporated to dryness. The product was purified on a silica column using a gradient of methanol from 0 to 5% in dichloromethane/1% TEA. The product was obtained as a white foam (4.55 gm, 31%). This product was identified with HNMR and ES-MS.

Compound 8

Synthesis of 3'-O-[(diisopropylamine)(2-cyanoethoxy) phosphino)]-5'-O-(4,4'-dimethoxytriphenylmethyl)-4-N-(4,7,10-trioxa-1-tridecaneaminobiotin)-2'-deoxycytidine The 5'-DMT-Biotin-dC (Compound 7) (507 mg, 0.453 mmol) was dissolved in dry acetonitrile (30 ml) and dichloromethane (5 ml), then diisopropylamine (73 mg, 0.56 mmol), tetrazole (1.15 ml, 0.52 mmol) and 2-cyanoethyl N,N,N'N'-tetraisopropylphosphane 214 mg, 234 µL, 0.7 mmol) were added and the mixture stirred under nitrogen at RT. After 2 hrs, TLC on silica gel (45%:45%:5%:5%: of ethyl acetate:dichloromethane:triethylamine:methanol) showed that only about 30% of product was formed and about 70% of starting material was unreacted. More reagents were added until most of starting material was converted, with only about 5% left unreacted. The solvent was evaporated to dryness, dissolved in dry dichloromethane, washed with sodium bicarbonate solution (5%), saturated brine solution, then the organic layer was dried over sodium sulphate, evaporated to dryness. Column chromatography was carried out on silica gel using (48%:48%:4% of ethyl acetate:dichloromethane:triethylamine) to (47%:47%:5%: 1% of ethyl acetate:dichloromethane:triethylamine: methanol). The desired product was obtained as a colorless gummy product (406 mg, 70%). This material was co-evaporated three times from a mixture of dry benzene and dichloromethane, then was kept in desiccated containing $P_2O_5$ and NaOH pellets under vacuum for 26 hrs before used in DNA synthesis.

Figure 34:
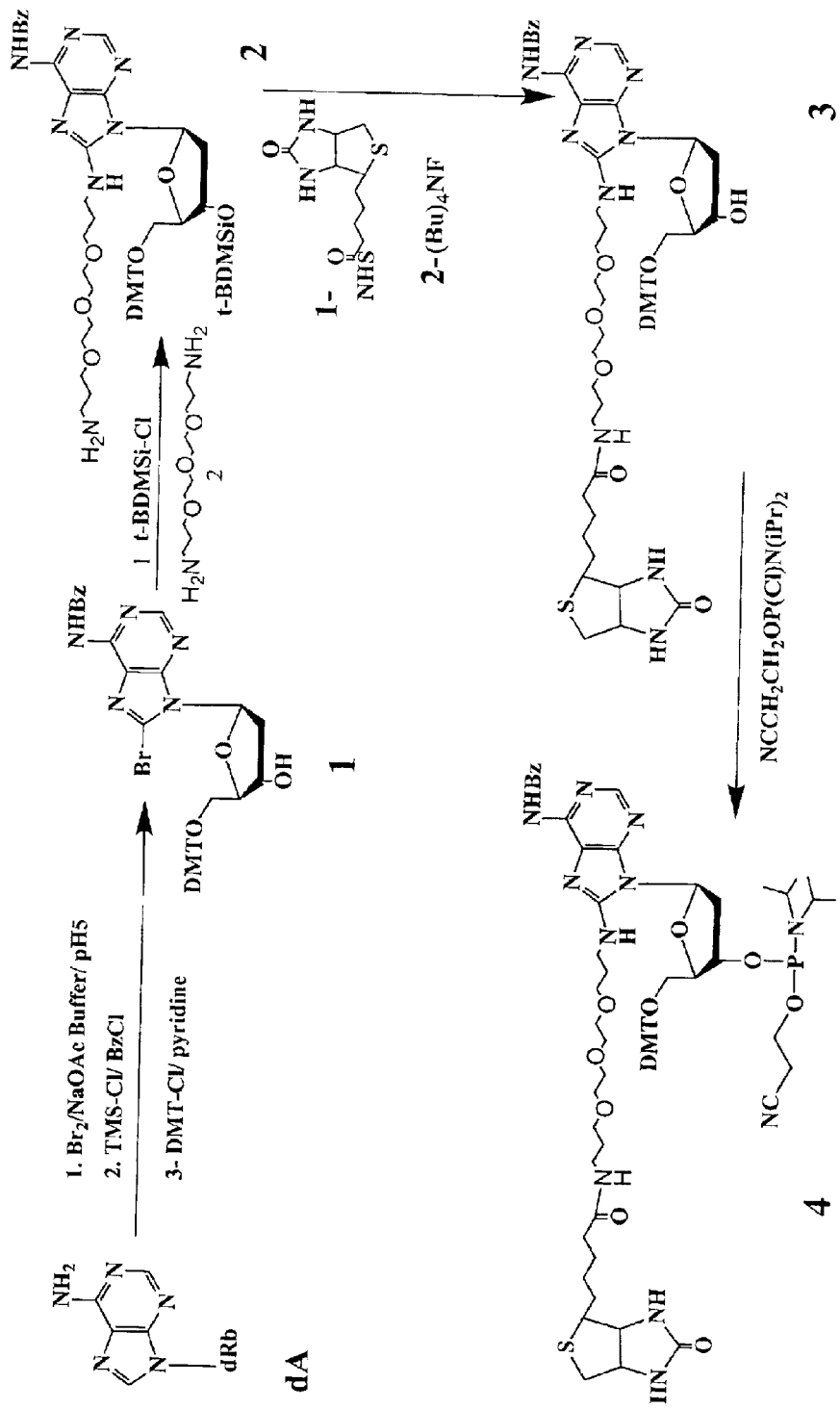
FIG. 34 is a schematic diagram of the steps involved in the synthesis of the phosphoroamidite of biotin-deoxyadenosine (dA) (Reagent D).

D. Synthesis of Biotinylated 2'-Deoxyadenosine Phosphoramidite (FIG. 34)

Compound 1

Synthesis of 8-bromo-2'-deoxyadenosine

2'-deoxyadenosine (7 gm, 25.9 mmol) was dissolved in sodium acetate buffer (150 mL, 1 M, pH 5.0) by worming it to about 50° C., then was cooled dawn to 30° C., then 3 mL of bromine in 100 mL of the same buffer was added drop wise at RT for 15 min, to the reaction. After 6 hrs the TLC on silica gel (20% MeOH in $CH_2Cl_2$) showed that all starting material was converted to a new product. The reaction was discolored by adding some sodium metabisulfite ($Na_2S_2O_5$) while stirring. The color changed to a white solution, and the pH of the reaction was neutralized by adding 1 M NaOH. The reaction mixture was kept at 4° C. (refrigerator) for 16 hrs. The solid material was then filtered, washed with cold water, then acetone to give a solid yellow powder product (5.75 gm, 64%). The structure of this product was confirmed by H-NMR and ES-MS.

Compound 2

Synthesis of $N^6$-benzoyl-8-bromo-5'-O-(4,4'-dimethoxytrityl)-2'-deoxyadenosine 8-bromo-2'-deoxyadenosine (Compound 1) (7.7 gm. 22.17 mmol) was dried by co-evaporation with dry pyridine and the solid was suspended in 200 ml of dry pyridine followed by the addition of 4,4'-dimethoxytriphenylmethyl chloride (DMT-Cl, 9 gm, 26.6 mmol). After stirring for 4 hrs at RT, TLC on a silica gel showed that a new product was formed and some starting material was unreacted. Another amount of DMT-Cl (3 gm) was added and stirred at RT for 2 hrs. When TLC showed that all starting material was converted to new product with a higher Rf, the reaction mixture was cooled to 0° C. and trimethylchlorosilane (12.042 gm., 14 mL, 110.85 mmol) was added drop wise while cooling and after 40 min while stirring benzoyl chloride (15.58 gm, 12.88 mL, 110.85 mmol) was similarly added. The reaction was allowed to react at RT over 2 hrs. The reaction was quenched by slow addition of cold water (50 ml), followed by addition of concentrated ammonia (30%, 50 ml). After 30 min, the reaction mixture was evaporated to dryness. The residue was dissolved in water, and the solution was extracted with ethyl acetate three times, the organic layer washed with saturated sodium bicarbonate solution, and then brine. The organic phase was dried over sodium sulphate, then evaporated to dryness. The product was purified by silica column chromatography, to give a yellowish solid product (6.79 gm, 41.6%). The structure of this product was confirmed by H NMR and ES-MS.

Compound 3

Synthesis of $N^6$-benzoyl-8-bromo-3'-O-t-butyldimethylsily-5'-O-(4,4'-dimethoxytrityl)-2'-deoxyadenosine 6N-benzoyl-8-bromo-5'-O-(4,4'-dimethoxytrityl)-2'-deoxyadenosine (Compound 2) (14 gm, 19 mmol) and imidazole (1.94 gm, 28.5 mmol) were dissolved in 100 mL of dry DMF and t-butyldimethyl-silyl chloride (4.3 gm, 28.5 mmol) added to the stirring solution at room temperature. After 4 hrs, TLC on silica gel (2.5% MeOH in $CH_2Cl_2$) showed that all starting material had been converted to a new product with higher Rf. The solution was concentrated into a small volume, then about 400 mL of ether was added and washed three times with saturated aqueous NaCl solution. The organic layer was dried over anhydrous $Na_2SO_4$, and the filtrate was evaporated to give an off-white foamy product (16.18 gm, 100%). HNMR and ES-MS confirmed the structure.

Compound 4

Synthesis of $N^6$-benzoyl-8-(4,7,10-trioxa-1-tridecaneamino)-3'-O-t-butyldimethylsilyl-5'-O-(4,4'-dimethoxytrityl)-2'-deoxyadenosine $N^6$-bBenzoyl-8-bromo-3'-O-t-butyldimethylsilyl-5'-O-(4,4'-dimethoxytrityl)-2'-deoxyadenosine (Compound 3) (8.31 gm, 9.7 mmol) was dissolved in 200 ml of ethanol then 4,7,10-trioxa-1,13-tridecanediamine (6.75 gm, 6.7 ml, 30 mmol) was added at once and kept stirring at 50° C. After 16 hrs TLC showed that all starting material was converted to one major product with lower Rf and other minor products. The solvent was evaporated to dryness, dissolved in dichloromethane, washed three times with a solution of brine, dried over anhydrous $Na_2SO_4$, then evaporated to give a yellow gummy material. Column chromatography (1% $TEA+CH_2Cl_2$) to (1% TEA+5% MeOH+$CH_2Cl_2$) permitted the purification of the major product as an off-white gummy material (4.53 gm, 47%). This product was identified with HNMR and ES-MS.

Compound 5

Synthesis of $N^6$-benzoyl-8-(4,7,10-trioxa-1-tridecaneaminobiotin)-3'-O-t-butyldimethylsilyl-5'-O-(4,4'-dimethoxytrityl)-2'-deoxyadenosine $N^6$-benzoyl-8-(4,7,10-trioxa-1-tridecaneamino)-3'-O-t-butyldimethylsilyl-5'-O-(4,4'-dimethoxytrityl)-2'-deoxyadenosine (Compound 4) (4.53 gm. 4.57 mmol) and biotin-NHS ester (3.12 gm, 9.13 mmol) were dissolved in 75 mL of DMF and few drops of TEA were added and the reaction was stirred at RT. After 2 hrs TLC on silica gel (5% MeOH+1% TEA+94% $CH_2Cl_2$) showed the formation of one major product less polar than starting material and another minor spot has lower Rf. The solvent was evaporated to dryness, then dissolved in $CH_2Cl_2$ and washed three times with a saturated solution of NaCl, dried the organic layer, evaporated to dryness to leave a yellow gummy material. This material was purified with column chromatography on silica gel by using (1% TEA+$CH_2Cl_2$) to (1% TEA+2.5% MeOH+$CH_2Cl_2$) as eluant. After evaporating the fractions containing the product, gave a yellowish solid material (3.16 g, 78%). HNMR and ES-MS confirmed the structure.

Compound 6

Synthesis of $N^6$-benzoyl-8-(4,7,10-trioxa-1-tridecaneaminobiotin)-5'-O-(4,4'-dimethoxytrityl)-2'-deoxyadenosine $N^6$-benzoyl-8-(4,7,10-trioxa-1-tridecaneaminobiotin)-3'-O-t-butyldimethylsilyl-5'-O-(4,4'-dimethoxytrityl)-2'-deoxyadenosine (Compound 5) (3.16 gm, 2.6 mmol) was dissolved in 100 mL of dry THF, and then about (3.25 ml, 3.25 mmol) of tetrabutylammonium fluoride in THF was added in 5 min while stirring at RT. After 8 hrs, TLC on silica gel (10% MeOH+1% TEA+89% $CH_2Cl_2$) showed that a new product with lower $R_f$ formed. The solvent was evaporated to give a yellow oily material. Column chromatography on silica gel eluted with (99% $CH_2Cl_2$+1% TEA) to (5% MeOH+1% TEA+94% $CH_2Cl_2$) permitted the purification of the product as a white foamy product (2.86 gm, 100%). HNMR and ES-MS confirmed the structure.

Compound 7

Synthesis of $N^6$-benzoyl-8-(4,7,10-trioxa-1-tridecaneaminobiotin)-3'-O-[(diisopropylamine)(2-cyanoethoxy) phosphino)]-5'-O-(4,4'-dimethoxytrityl)-2'-deoxyadenosine $N^6$-benzoyl-8-(4,7,10-trioxa-1-tridecaneaminobiotin)-5'-O-(4,4'-dimethoxytrityl)-2'-deoxyadenosine (Compound 6) (0.959 gm, 0.86 mmol) was dissolved in a mixture of dry acetonitrile (200 mL) and dichloromethane (50 mL), and diisopropylamine (224 μL, 1.29 mmol) followed by the addition of 2-cyanoethyl N, N, N', N'-tetraisopropylphosphane (404 μL, 1.29 mmol) and tetrazole (2.6 ml, 1.2 mmol, 0.45 M solution in dry acetonitrile). The addition and subsequent reaction are performed under argon while stirring at RT. After 1.5 h, TLC on silica gel (5% MeOH+5% TEA+45% EA+45% $CH_2Cl_2$) showed that only about 50% of starting material (SM) was converted to a new product. The same above amount of reagents were added to the reaction and kept stirring for another 2 hrs at RT. TLC showed that about 95% of SM was converted to a new product with higher Rf. The solvent was evaporated to dryness then was dissolved in dichloromethane, extracted once with 5% solution of bicarbonate, followed by saturated brine solution and then dried over anhydrous sodium sulfate and evaporated to dryness. Column chromatography on silica gel (10% TEA+45% EA+45% $CH_2Cl_2$) first, then (5% TEA+5% MeOH+45% EA+45% $CH_2Cl_2$). After evaporating the fractions containing the product, gave a yellow gummy material (774 mg). This material was co-evaporated three times from a mixture of dry benzene and dichloromethane, then was kept in desiccant containing $P_2O_5$ and NaOH pellets under vacuum for 24 hrs before used in DNA synthesis.

E. Synthesis of Oligonucleotides Containing Biotin-dC and Biotin-dA

The syntheses of oligonucleotides containing biotin-dC and Biotin-dA, site-specifically located, were performed on a CPG support using a fully automated DNA synthesizer and the commercially available fully protected deoxynucleosides phosphoramidites. Syntheses of all these oligonucleotides were carried out at 1.0 and 0.4 μmol scale. The coupling time for the biotin-dC and dA were extended to 900 seconds. The coupling efficiency of the biotin-dC and dA phosphoramidites was found greater than 96%. After coupling of the biotinylated phosphoramidites, the remaining residues comprising the e-tag reporter of interest were added. Upon completion of the synthesis of the oligonucleotides, they were deprotected with concentrated ammonia at 65° C. for 1 hour. These oligonucleotides were purified by reverse-phase HPLC and desalted by OPC column, then used as such.

F. Synthesis of ACLA001 (FIG. 17) on an ABI 394 DNA Synthesizer

6-Carboxyfluorescein (6-FAM) phosphoramidite is prepared by the addition of 2.96 ml of anhydrous acetonitrile to a 0.25 gram bottle of the fluorescein phosphoramidite, to give a 0.1 M solution. The bottle is then loaded onto the ABI 394 DNA synthesizer at position 8 using the standard bottle change protocol. The other natural [$dA^{bz}$ (0.1 M: 0.25 g/2.91 mL anhydrous acetonitrile), $dC^{Ac}$(0.1 M: 0.25 g/3.24 mL anhydrous acetonitrile), dT(0.1 M: 0.25 g/3.36 mL anhydrous acetonitrile), $dG^{dmf}$ (0.1 M: 0.25 g/2.81 mL anhydrous acetonitrile)] phosphoramidite monomers are loaded in a similar fashion to ports 1–4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols.

Standard Reagents Employed for DNA Synthesis:

Oxidizer: 0.02 M Iodine (0.015 M for MGB Probes)

DeBlock: 3% trichloracetic acid in dichloromethane

Activator: 1H-Tetrazole in anhydrous acetonitrile

HPLC Grade Acetonitrile (0.002% water)

Cap A: acetic anhydride

Cap B: N-methyl imidazole

The target sequence of interest is then input with a terminal coupling from port 8 to attach ACLA001 to the 5'-end of the sequence. A modified cycle is then chosen such that the desired scale (0.2 μmol, 1.0 μmol, etc.) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing e-tag reporters have been synthesized on various standard 500 Å CPG supports (Pac-dA-CPG, dmf-dG-CPG, Ac-dC-CPG, dT-CPG) as well as specialty supports containing 3'-biotin, 3'-amino linker, and minor grove binding species.

Upon completion of the synthesis, the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipette and placed into a 1.5 mL Eppendorf tube. The solution is concentrated in vacuo and submitted for HPLC purification.

G. Synthesis of ACLA002 (FIG. 17) on an ABI 394 DNA Synthesizer

6-Carboxyfluorescein (6-FAM) phosphoramidite is prepared by the addition of 2.96 mL of anhydrous acetonitrile to a 0.25 gram bottle of the fluorescein phosphoramidite, to give a 0.1 M solution. The bottle is then loaded onto the ABI 394 DNA synthesizer at position 8 using the standard bottle change protocol. The other natural [$dA^{bz}$ (0.1 M: 0.25 g/2.91 mL anhydrous acetonitrile), $dC^{Ac}$ (0.1 M: 0.25 g/3.24 mL anhydrous acetonitrile), dT (0.1 M: 0.25 g/3.36 mL anhydrous acetonitrile), $dg^{dmf}$ (0.1 M: 0.25 g/2.81 mL anhydrous acetonitrile)] phosphoramidite monomers are loaded in a similar fashion to ports 1–4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols. The target sequence of interest is then input with a terminal coupling from port 8 and a penultimate coupling of thymidine to the 5'-end of the sequence to assemble ACLA002. A modified cycle is then chosen such that the desired scale (0.2 μmol, 1.0 μmol, etc.) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing e-tag reporters have been synthesized on various standard 500 A CPG supports (Pac-dA-CPG, dmf-dG-CPG , Ac-dC-CPG, dT-CPG) as well as specialty supports containing 3'-biotin, 3'-amino linker, and minor grove binding species.

Upon completion of the synthesis the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipette and placed into a 1.5 mL Eppendorf tube. The solution is concentrated in vacuo and submitted for HPLC purification.

H. Synthesis of ACLA003 (FIG. 17) on an ABI 394 DNA Synthesizer

6-Carboxyfluorescein (6-FAM) phosphoramidite is prepared by the addition of 2.96 mL of anhydrous acetonitrile to a 0.25 gram bottle of the fluorescein phosphoramidite, to give a 0.1 M solution. The bottle is then loaded onto the ABI 394 DNA synthesizer at position 8 using the standard bottle change protocol. The other natural [$dA^{bz}$ (0.1 M: 0.25 g/2.91 mL anhydrous acetonitrile), $dC^{Ac}$ (0.1 M: 0.25 g/3.24 mL anhydrous acetonitrile), dT (0.1 M: 0.25 g/3.36 mL anhydrous acetonitrile), $dG^{dmf}$ (0.1 M: 0.25 g/2.81 mL anhydrous acetonitrile)] phosphoramidite monomers are loaded in a similar fashion to ports 1–4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols. The target sequence of interest is then input with a terminal coupling from port 8 and two penultimate couplings of thymidine to the 5'-end of the sequence to assemble ACLA003. A modified cycle is then chosen such that the desired scale (0.2 μmol, 1.0 μmol, etc.) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing e-tags have been synthesized on various standard 500 A CPG supports (Pac-dA-CPG, dmf-dG-CPG, Ac-dC-CPG, dT-CPG) as well as specialty supports containing 3'-biotin, 3'-amino linker, and minor grove binding species.

Upon completion of the synthesis, the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipette and placed into a 1.5 mL Eppendorf tube. The solution is concentrated in vacuo and submitted for HPLC purification.

I. Synthesis of ACLA016 (FIG. 17) on an ABI 394 DNA Synthesizer

6-Carboxyfluorescein (6-FAM) phosphoramidite is prepared by the addition of 2.96 mL of anhydrous acetonitrile to a 0.25 gram bottle of the fluorescein phosphoramidite, to give a 0.1 M solution. The bottle is then loaded onto the ABI 394 DNA synthesizer at position 8 using the standard bottle change protocol. Spacer phosphoramidite C3 (0.25 g) is dissolved in 5.0 mL of anhydrous acetonitrile and loaded onto position 5 of the synthesizer. The other natural [dA$^{bz}$ (0.1 M: 0.25 g/2.91 mL anhydrous acetonitrile), dC$^{Ac}$(0.1 M: 0.25 g/3.24 mL anhydrous acetonitrile), dT (0.1 M: 0.25 g/3.36 mL anhydrous acetonitrile), dG$^{dmf}$ (0.1 M: 0.25 g/2.81 mL anhydrous acetonitrile)] phosphoramidite monomers are loaded in a similar fashion to ports 1–4. Acetonitrile is loaded onto side port 18, standard tetrazole activator is loaded onto port 9, CAP A is loaded onto port 11, CAP B is loaded onto port 12, oxidant is loaded onto port 15, and deblock solution is loaded onto port 14 all using standard bottle change protocols. The target sequence of interest is then input with a terminal coupling from port 8 and a penultimate coupling of the C3 spacer from port 5 to assemble ACLAO 16. A modified cycle is then chosen such that the desired scale (0.2 μmol, 1.0 μmol, etc.) of DNA is synthesized. The modified cycle contains an additional wait step of 800 seconds after any addition of 6-FAM. A standard DNA synthesis column containing the support upon which the DNA will be assembled is then loaded onto one of four positions of the DNA synthesizer. DNA containing e-tag reporters have been synthesized on various standard 500 A CPG supports (Pac-dA-CPG, dmf-dG-CPG, Ac-dC-CPG, dT-CPG) as well as specialty supports containing 3'-biotin, 3'-amino linker, and minor grove binding species.

Upon completion of the synthesis the column is removed from the synthesizer and either dried under vacuum or by blowing air or nitrogen through the column to remove residual acetonitrile. The column is then opened and the CPG is removed and placed in a 1-dram vial. Concentrated ammonia is added (2.0 mL) and the vial is sealed and placed into a heat block set at 65° C. for a minimum of two hours. After two hours the vial is allowed to cool to room temperature after which the ammonia solution is removed using a Pasteur pipette and placed into a 1.5 mL Eppendorf tube. The solution is concentrated in vacuo and submitted for HPLC purification.

All other e-tag s are synthesized in a similar manner to that described above. FIG. 17 provides a list of different e-tags with their structures. FIG. 6 provides a list of elution times of some of these e-tags on an ABI 3100 using POP4 as the separation matrix. $C_3$, $C_6$, $C_9$ and $C_{18}$ are commercially available phosphoramidite spacers from Glen Research, Sterling, Va. The units are derivatives of N,N-diisopropyl, O-cyanoethyl phosphoramidite, which is indicated by Q. The subscripts indicate the number of atoms in the chain, which comprises units of ethyleneoxy terminating in Q with the other terminus protected with DMT. The letters without subscripts A, T, C and G indicate the conventional nucleotides, while $T^{NH_2}$ intends amino thymidine and $C^{Br}$ intends bromocytidine. In FIG. 8, the numbers indicate the e-tag reporter as indicated in FIG. 17.

Example 1

Singleplex Amplifications of Allele 1 and Allele 2

The experiment was set up to run in the following fashion (6 samples, a triplicate for Allele1 and another triplicate for Allele-2):

22 μL of Mastermix

13 μL of probes and primers (both the probes are present)

4.0 μL of Allele-1 or Allele-2

11 μL of buffer (10 mM Tris-HCl, 1 mM EDTA, pH8.0)

Allele 1 was labeled with tetrachloro fluorescein (TET), and Allele 2 was labeled with fluorescein (FAM), each having characteristics as set forth in FIG. 1B.

The above volumes were added to a PCR tubes and the reaction mixtures were cycled on a Gene Amp® system 9600 thermal cycler (Perkin Elmer) as follows:

50° C.; 2 MIN (for optimal AmpErase UNG activity)

96° C.; 10 MIN (required to activate AmpliTaq Gold DNA Polymerase)

40 cycles of:

95° C.; 15 SEC

60° C.; 60 SEC

70° C.; 10 MIN

4° C.; storage

Figure 18A:
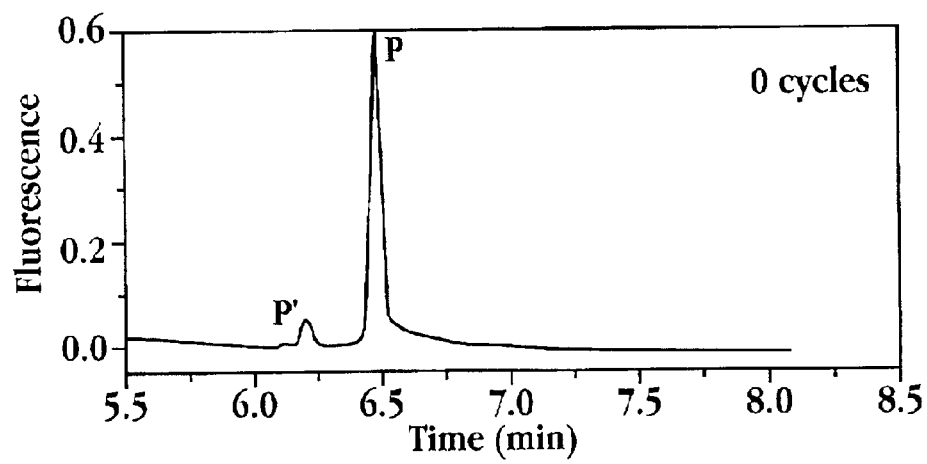
FIGS. 18A and B depict the CE separation of the reaction products of Allele 1 after 0 and 40 cycles. CE instrument: Beckman P/ACE/5000 with LIF detection. BGE: 2.5% LLD 30, 7M urea, 1×TBE. Capillary: 100 μm i.d., 375 μm o.d., Lc=27 cm, Ld=6.9 cm. Detection; $\lambda_{ex}$=488 nm, $\lambda_{em}$=520 nm. Injection: 5 s at 2.0 kV. Field strength: 100V/cm at rt. Peaks: P=unreacted snp detection sequence or e-tag probe, P'=snp detection sequence or e-tag reporter product, TET= tetrachlorofluorescein. (from 00 app)

Results from experiments with Allele-1 are shown in FIGS. 18A and B: CE separation of the reaction products of Allele 1 after 0 and 40 cycles. CE instrument was Beckman P/ACE 5000 with LIF detection. BGE: 2.5% LDD30, 7 M urea, 1×TBE. Capillary: 100 μm i.d., 375 μm o.d., Lc=27 cm, Ld=6.9 cm. Detection: $\lambda_{ex}$=488 nm, $\lambda_{em}$=520 nm. Injection: 5 s at 2.0 kV. Field strength: 100 V/cm at room temperature. Peaks: P=unreacted primer, P'=primer product.

Figure 18B:
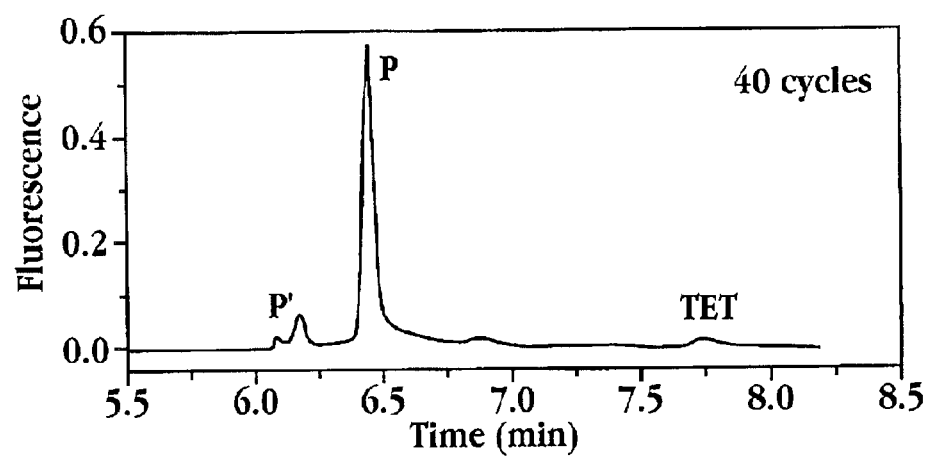
Figure 19A:
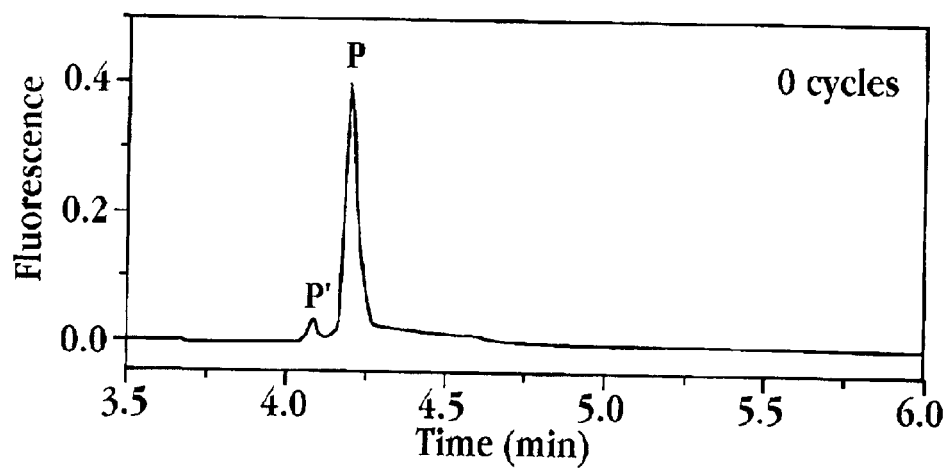
FIGS. 19A and B depict the CE separation of the reaction products (or e-tag reporters) of Allele 2 after 0 and 40 cycles. Experimental conditions are the same as FIG. 18, except for BGE composition; 2% LDD30, 1×TBE, FAM=fluorescein.
Figure 19B:
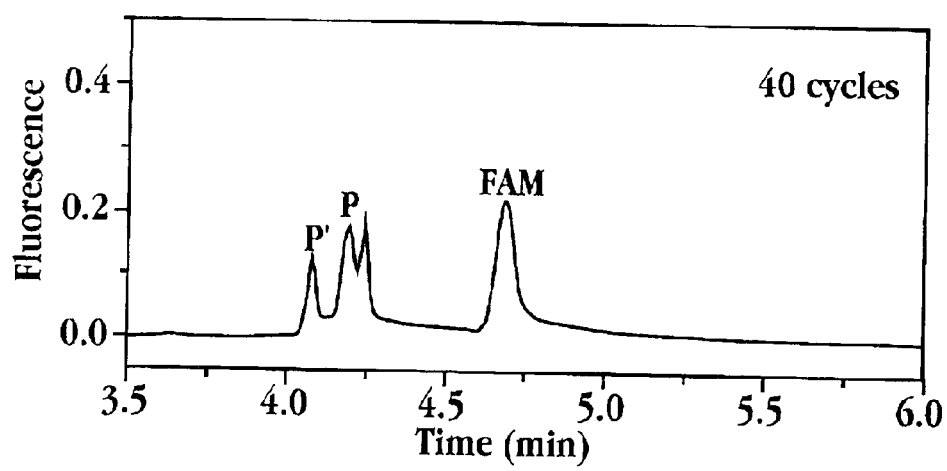

Results from experiments with Allele-2 are shown in FIGS. 19A and B: CE separation of the reaction products of Allele 2 after 0 and 40 cycles. Experimental conditions were as given above for the FIG. 18 experiment except for the BGE composition: 2.0% LDD30, 1×TBE.

Example 2

A Multiplexed Reaction with Both Allele 1 and Allele 2 Present in Equal Ratio

The experiment was set up in the following fashion (3 reaction tubes, a triplicate):

22 μL of Mastermix

13 μL of probes and primers (both of the probes were present)

4.0 µL of Allele-1

4.0 µL of Allele-2

7 µL of buffer (10 mM Tris-HCl, 1 mM EDTA, pH 8.0)

The above volumes were added to a PCR tubes and the reaction mixtures were cycled on a Gene Amp® system 9600 thermal cycler (Perkin Elmer) as follows:

50° C.; 2 MIN (for optimal AmpErase UNG activity)

96° C.; 10 MIN (required to activate AmpliTaq Gold DNA Polymerase)

40 cycles of:

95° C.; 15 SEC

60° C.; 60 SEC

70° C.; 10 MIN

4° C.; storage

Figure 20:
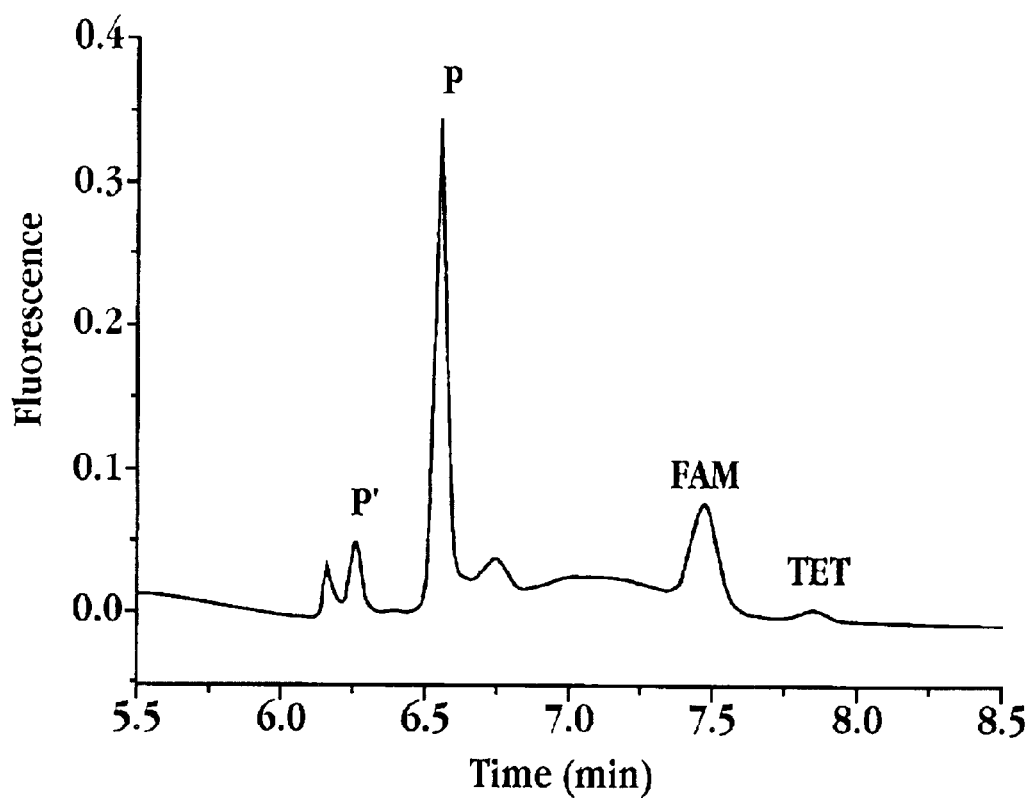
FIG. 20 is a graph of the CE separation of a 1:1 mixture of the 40 cycles products of Alleles 1 and 2, with experimental conditions as described for FIG. 18.

The results are shown in FIG. 20: CE separation of a 1:1 mixture of the 40 cycles products of Alleles 1 and 2. Experimental conditions were as given above for the experiments of FIG. 18.

Example 3

A Multiplexed Reaction with Both Allele 1 and Allele 2, where Allele 1 is 10 Times More Concentrated than Allele 2

The experiment was set up in the following fashion (3 reaction tubes, a triplicate):

22 µL of Mastermix

13 µL of probes and primers (both the probes were present)

5.0 µL of Allele 1

0.5 µL of Allele 2

9.5 µL of buffer (10 mM Tris-HCl, 11 mM EDTA, pH 8.0)

The above volumes were added to a PCR tubes and the reaction mixtures were cycled on a Gene Amp® system 9600 thermal cycler (Perkin Elmer) as follows:

50° C.; 2 MIN (for optimal AmpErase UNG activity)

96 C; 10 MIN (required to activate AmpliTaq Gold DNA Polymerase)

40 cycles of:

95° C.; 15 SEC

60° C.; 60 SEC

70 C; 10 MIN

4 C; storage

Figure 21:
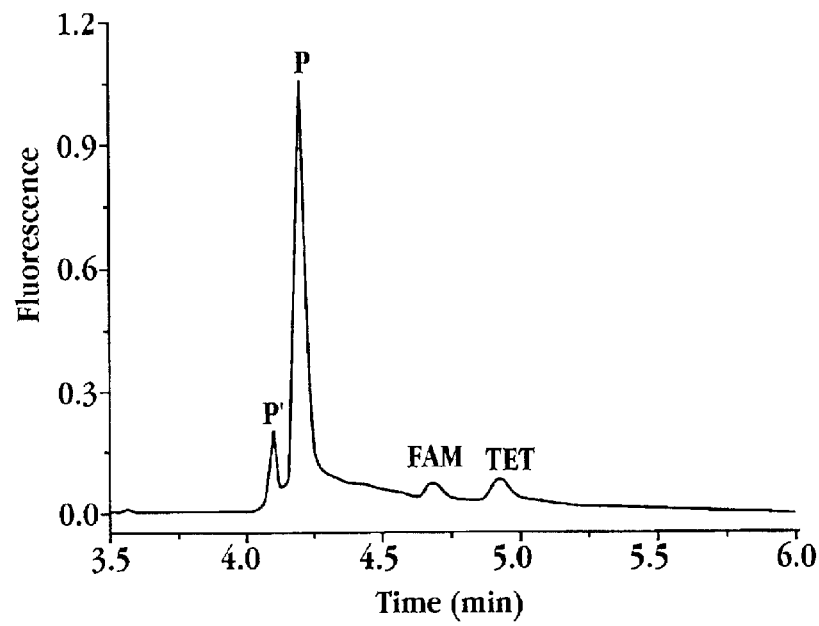
FIG. 21 is a graph of the CE separation of a 1:10 mixture of the 40 cycles products of Alleles 1 and 2, with experimental conditions as described for FIG. 18.

The results are shown in FIG. 21: CE separation of a 1:10 mixture of the 40 cycles products of Alleles 1 and 2. Experimental conditions were as given for the experiments of FIG. 18.

Example 4

Electroseparation of Label Conjugates on Microfluidic Chip

1. Label conjugates comprising fluorescein linked to three different peptides, namely, KKAA (SEQ ID NO:5), KKKA (SEQ ID NO:6) and KKKK (SEQ ID NO:7) were prepared as follows: The protected tetrapeptide was prepared on resin using Merrifield reagents. The N-terminus of the last amino acid was reacted with fluorescein N-hydroxysuccinimide (Molecular Probes). The peptides were cleaved from the resin and purified by high performance liquid chromatography (HPLC).

Figure 22:
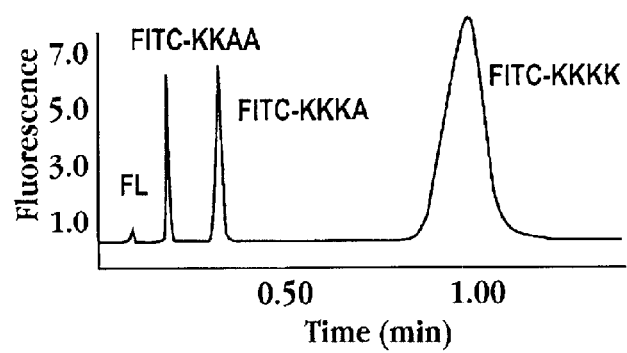
FIG. 22 is an electropherogram of electrophoretic tags for electrophoresis differing by a 1000-fold concentration.
Figure 23A:
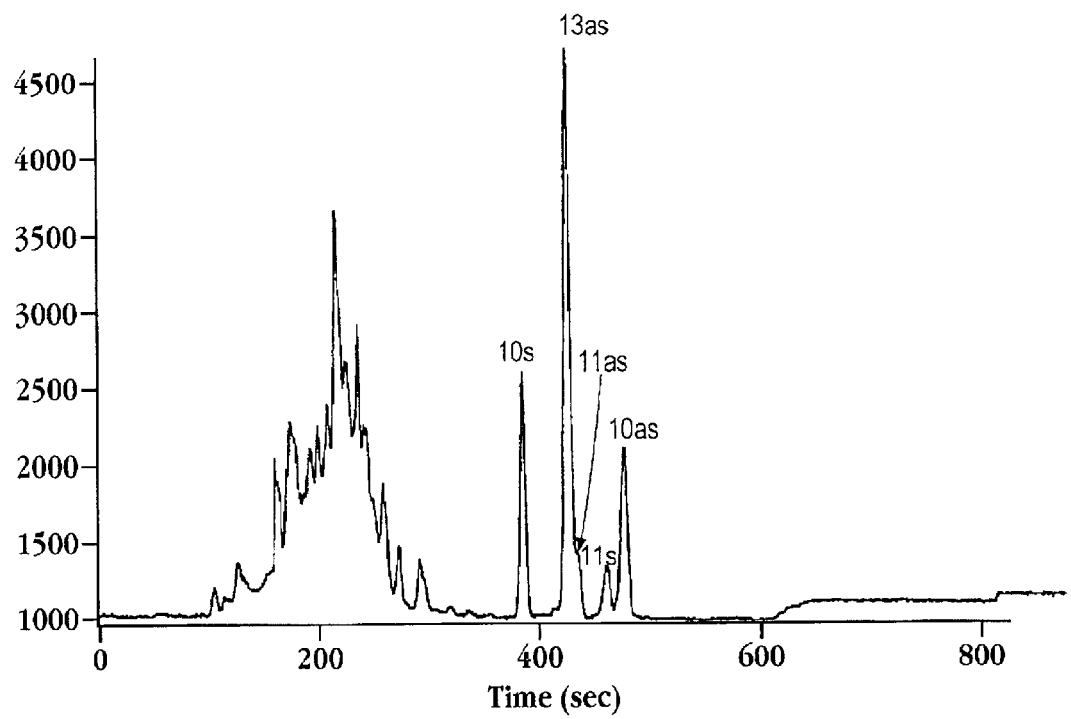
FIGS. 23A–E and G are electropherograms from analysis of 5 snps of the cystic fibrosis genes, using multiplexed PCR and the subject e-tag probes. Three individual snp loci and a triplex reaction are shown, using multiplexed PCR and the subject e-tag probes (FIGS. 23A–E and G), along with an image of agarose gel separation of the triplex reaction (23F).
Figure 23B:
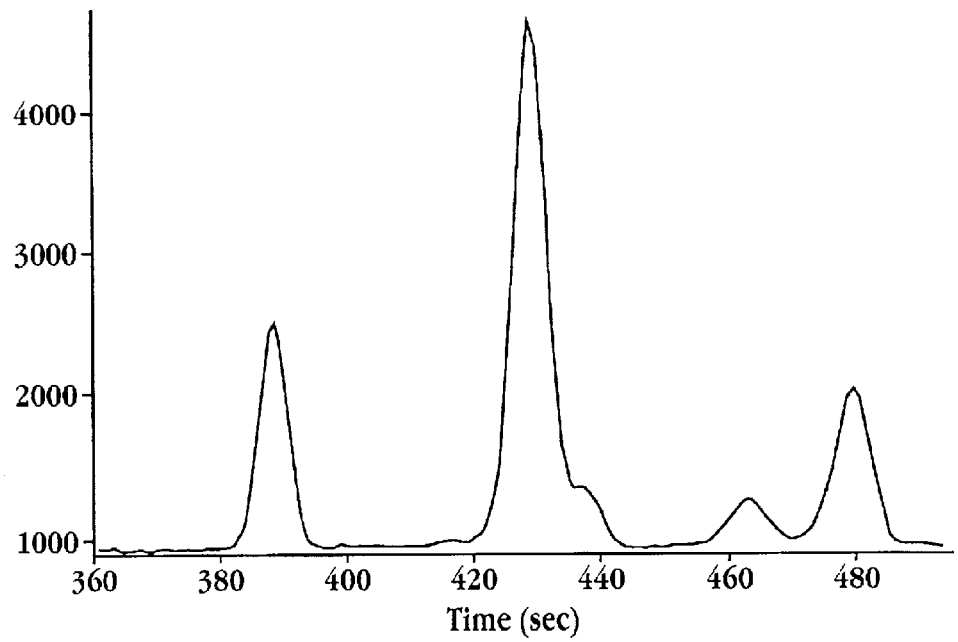
Figure 23C:
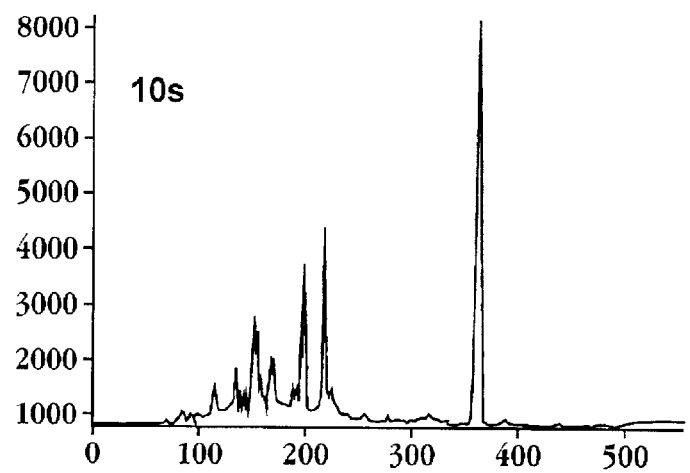
Figure 23D:
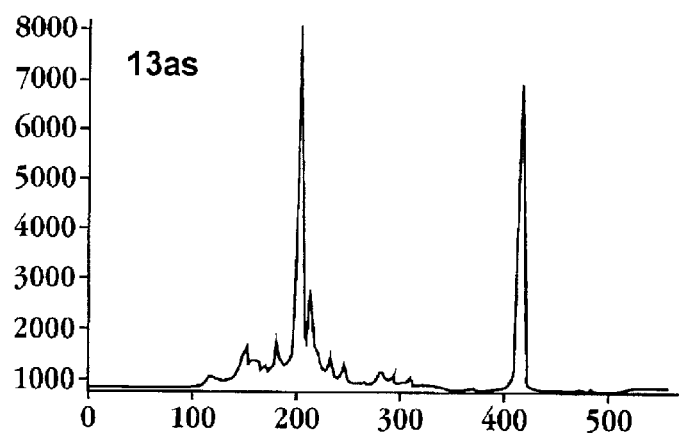
Figure 23E:
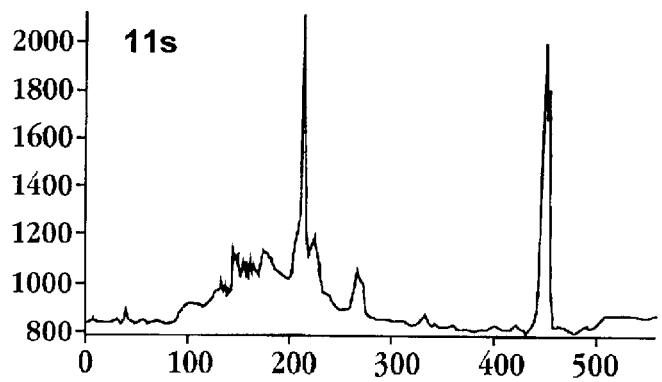
Figure 23F:
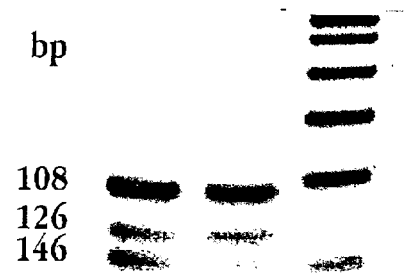
Figure 23G:
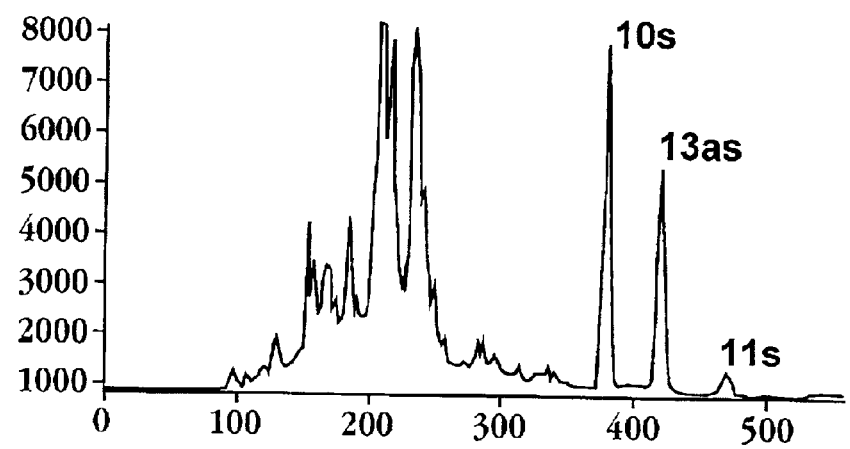

The label conjugates, prepared as described above, and fluorescein were combined in an aqueous buffered solution and were separated and detected in an electrophoresis chip. Detection was 0.5 cm for the injection point on the anodal side of an electrophoresis channel. FITC-KKKK exhibited a negative charge and FITC-KKKA and FITC-KKKK exhibited a positive charge as determined by the migration time relative to EOF. The net charge of FITC-KKKK was greater than +1 and FITC-KKKA and FITC-KKKK migrated electrophoretically against the EOF. The results are shown in FIG. 22.

Example 5

Multiplexed Analysis of CFTR snp Loci with e-tag Probes

A. Capillary Electrophoresis of CFTR PCR Products with e-tag Probes on ABI 310

The following example demonstrates separation in a gel based capillary electrophoresis of cleavage of a probe. The conditions employed were: Gel: 2.5% LDD30 in 1×TBE with 7 M urea; CE: PE ABI 310; Capillary: 47 cm long; 36 cm to window; 75 µm ID; Running Buffer: 1×TBE. (LDD30 is a linear copolymer of N,N-diethyl acrylamide and N,N-dimethylacrylamide, 70:30).

The ABI310 was set up in accordance with the directions of the manufacturer. The parameters used were: injection: 5 sec, 2.0 kV; run: 9.4 kV, 45° C., 10 min. To determine the relative mobilities of the digested probes, a spike-in system was used. First one digested probe was separated and its peak site determined, then a second probe was spiked into the first probe and the two separated. Then, a third probe was spiked in and separated, and so on until the sites of all six probes was determined. The singleplex PCR runs were first separated followed by separation of the multiplex PCR, which was compared to the S1 digested separation.

B. Multiplexed Amplification of CFTR Fragments with e-tag Probes

In this study, reactions involved a plurality of probes in the same PCR reaction mixture for different SNPs in the gene for the Cystic Fibrosis transmembrane conductance regulator (CFTR). Taq DNA Polymerase exhibits 5' to 3' exonuclease activity, causing degradation of an e-tag probe hybridized to template DNA at the 3' end of a PCR primer. In the subject example, sequence-specific e-tag probes with a fluorescent dye attached to the 5' terminus of the probe were employed. PCR was performed with these probes, followed by separation by gel-based capillary electrophoresis to determine cleavage of the e-tag probe. Table 5 indicates the mutation name, exon location, and the nucleotide change and position of the snp in the CFTR sequence. The name of the oligonucleotide reagents, including e-tag probes and PCR primers, are indicated for each snp locus. Two PCR primers were generated to amplify each snp locus, where F indicates the primer in the forward direction, and R indicates the primer in the reverse direction. Two e-tag probes were generated for each snp locus—one hybridizing in the sense direction and one in the antisense direction, indicated as "s" or "as," respectively. The sequence ID numbers of each of these primers and probes are given in Table 6.

TABLE 5

CFTR snps, e-tag Probes, and PCR Primers

| Mutation Name | Exon Location | Nucleotide Change | PCR Primers | e-tag Probe | Predicted PCR Product Size |
|---|---|---|---|---|---|
| R560T | Exon 11 | G1811C | CF10P (F/R) | CF10s | 108 |
| R560T | Exon 11 | G1811C | CF10P (F/R) | CF10as | 108 |
| D1152H | Exon 18 | G3586C | CF11P (FlR) | CF11s | 188 |
| D1152H | Exon 18 | G3586C | CF11P (F/R) | CF11as | 188 |
| G1349D | Exon 22 | G4178A | CF13P (F/R) | CF13as | 138 |

TABLE 6

Sequence ID Numbers

| Oligonucleotide | SEQ ID NO. |
|---|---|
| CF10P F | SEQ ID NO:8 |
| CF11P F | SEQ ID NO:9 |
| CF13P F | SEQ ID NO:10 |
| CF10P R | SEQ ID NO:11 |
| CF11P R | SEQ ID NO:12 |
| CF13P R | SEQ ID NO:13 |
| CF10s | SEQ ID NO:14 |
| CF10as | SEQ ID NO:15 |
| CF11s | SEQ ID NO:16 |
| CF11as | SEQ ID NO:17 |
| CF13as | SEQ ID NO:18 |

The procedure employed in carrying out the singleplex PCR reaction was as follows:

1. Make up Master Mix

| 1x | Component |
    |---|---|
    | | 8 µL 25 mM MgCl$_2$ |
    | | 2.5 µL 10x PCR Buffer |
    | | 8 µL 10 ng/µL DNA template |
    | | 0.2 µL 25 m/M dNTPs |
    | | 1 µL 5 U/µL Taq Gold (added just prior to start of reaction) |

Combine 0.8 µL of 5 µM probe and 1 µL of 10 µM primers to PCR tubes, as indicated below.

2. Primers Probe

| Primers | Probe |
    |---|---|
    | CF10P | CF10s |
    | CF10P | CF10as |
    | CF11P | CF11s |
    | CF11P | CF11as |
    | CF13P | CF13as |

2. Aliquot 20.2 µL of the Master Mix to each tube.
3. In a PE2400 thermalcycler:
    96° C.; 10 MIN
    40 cycles of:

95° C.; 10 SEC
    55° C.; 30 SEC
    65° C.; 1 MIN
    70° C.; 10 MIN
    4° C.; storage The results are shown in FIG. 23. Results clearly demonstrate formation of a unique electrophoretic tag with a distinct mobility for each amplified sequence. Even in the multiplexed amplification each detection probe gave rise to a unique e-tag with a distinct mobility.

Example 6

Electroseparation of Nine e-tags on Microfluidic Chip

Label conjugates comprising 9 different fluorescein derivatives linked to thymine (FIG. 24, e-tag numbers 1–9): poly deoxythymidine (20-mer; with a 5' thiol group) is reacted with different maleimide-functionalized fluoresceins after which the product is ethanol precipitated. In a reaction of 12 µL in volume, 10 µL of 25 µM oligo, 1 µL 10×S1 nuclease reaction buffer, 1 µL of S1 nuclease incubated at 37° C. for 30 min followed by 96° C. for 25 min. The digested fragments are purified by HPLC.

Figure 24:
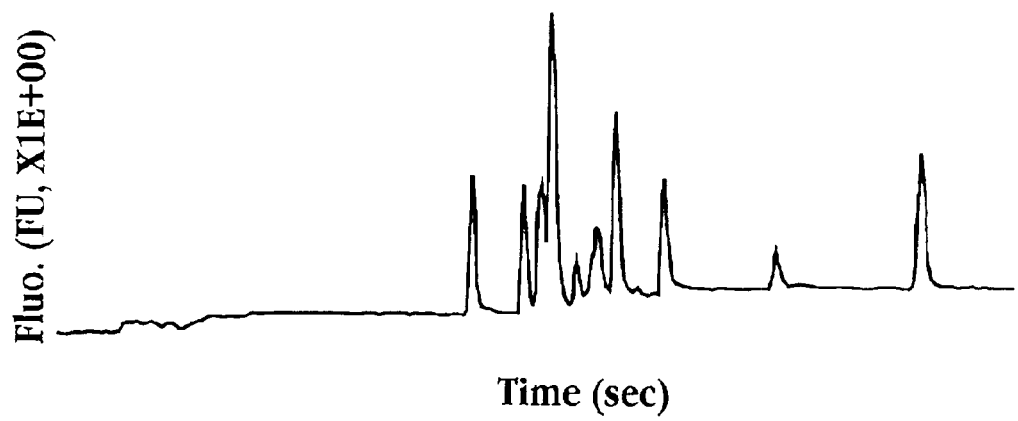
FIG. 24 is an electropherogram of a separation of nine negatively charged e-tag reporters.

The nine different e-tags prepared as described above and fluorescein were combined in an aqueous buffered and were separated and detected in an electrophoresis chip. Detection was 0.5 cm for the injection point on the anodal side of an electrophoresis channel. The results are shown in FIG. 24.

Example 7

Effect of Thiophosphate on 5'-3' Cleavage RT-PCR Conditions:

10 µL from a total volume of 25 µL of each mRNA was analyzed in a total volume of 50 µL containing 0.5 µM of each of the oligonucleotide primers, 0.2 mM of each dNTP, 100 nM of each e-tag labeled oligonucleotide probe, 1×RT PCR buffer, 2.5 mM MgCl$_2$, 0.1 U/µL Tfl DNA polymerase and 0.1 U/µL AMV Reverse Transcriptase (Promega Access, RT-PCR system).

Reverse Transcription was performed for 45 minutes at 48° C. followed by PCR. (40 thermal cycles of 30 s at 94° C., 1 min at 60° C. and 2 min at 69° C.). mRNA was obtained from M. Williams, Genentech, Inc. Probe and primer design was performed as described in Analytical Biochemistry, 270, 41–49 (1999). Phosphorothioates were attached to the 2, 3, 4 and 5 phosphate moieties from the 5' end. Separation was performed as described in the previous section.

Figure 25A:
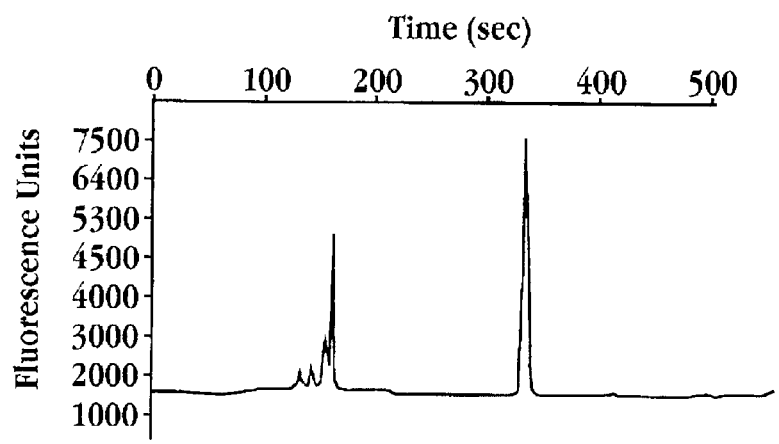
FIGS. 25A–D are electropherograms of probes employing a penultimate thiophosphate linkage in the e-tag probes to inhibit cleavage after the first phosphate linkage.
Figure 25B:
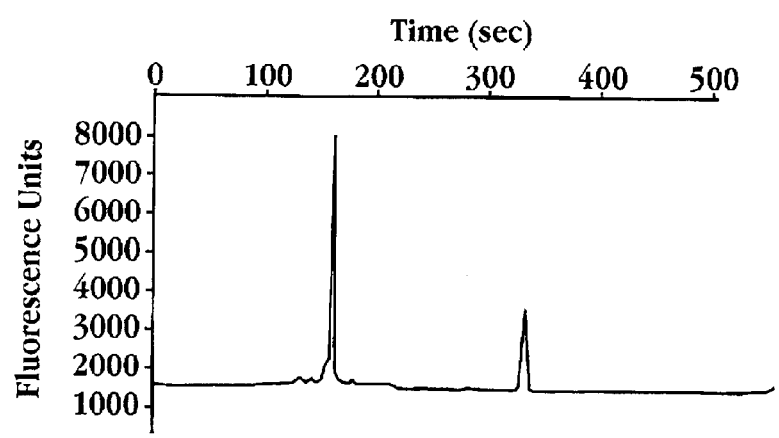

FIG. 25A demonstrates the formation of 5 different cleavage products in the PCR amplification of ANF (anti-nuclear factor) with an e-tag labeled at the 5' end of the sequence detection probe. In the second experiment, phosphate groups at the 2, 3, 4 and 5 positions are converted into thiophosphate groups. PCR amplification of ANF using a thiophosphate-modified sequence detection probe yielded only one cleavage product (FIG. 25B).

Figure 25C:
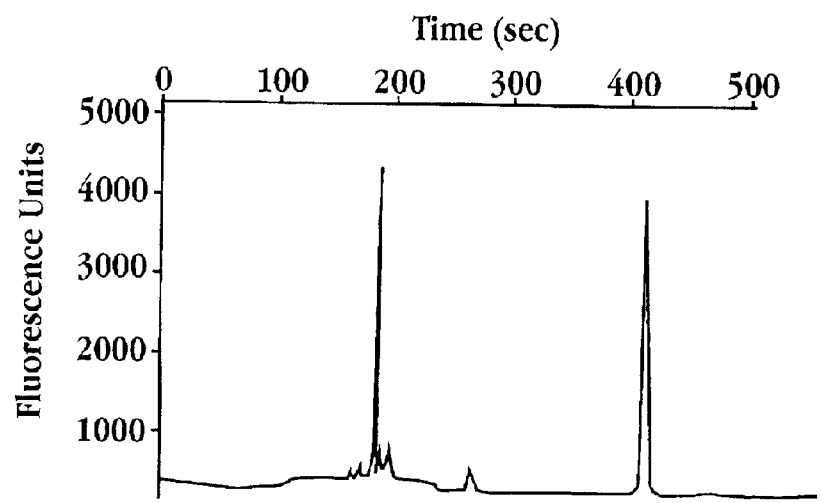
Figure 25D:
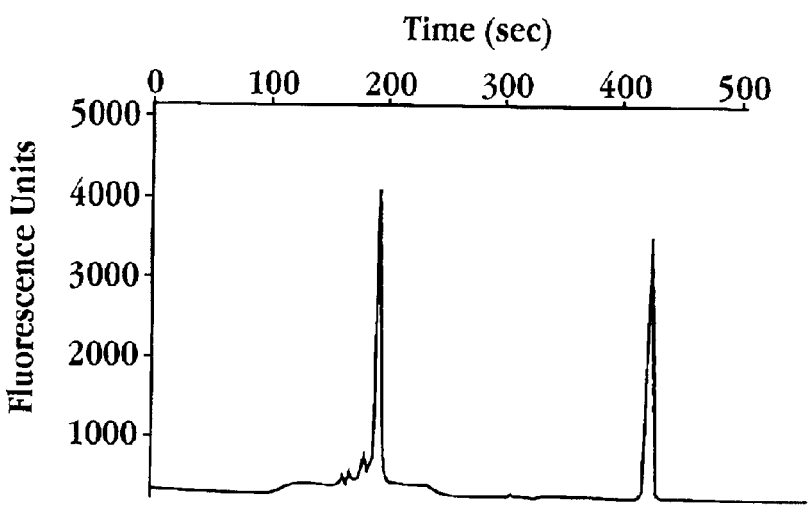

FIG. 25C demonstrates the formation of 3 different cleavage products in the PCR amplification of GAPDH with an e-tag attached to the 5' end of the sequence detection probe. In a second experiment, phosphate groups at positions 2 and 3 are converted into thiophosphate groups. PCR amplification of GAPDH using the thiophosphate-modified sequence detection probe yielded one predominant cleavage product (FIG. 25D).

The results clearly demonstrate for two different genes that thiophosphate linkages prevent cleavage at multiple sites of a detection probe. A single detectable entity (a single e-tag reporter, FIGS. 25B and D) is generated as a consequence of the amplification reaction.

Example 8

S1 Nuclease Digestion of e-tag Reporter Probes

In a 1.5 ml tube, 10 µL of e-tag reporter probe was added at a concentration of 10 µM, followed by addition of 1.5 µL of 10×S1 nuclease reaction buffer, 0.5 μL of S1 nuclease (Promega, Cat. # M5761, 20–100 unit/μL), and 3 μL of Tris-EDTA buffer to bring the final volume to 15 μL. The reaction was incubated at 37° C. for 20 min followed by 25 min at 96° C. to inactivate the nuclease.

Example 9.

5' Nuclease Assays for Monitoring Specific mRNA Expression in Cell Lysates

THP-1 cells (American Type Culture Collection, Manassas, Va.) were cultured in the presence or absence of 10 nM phorbol 12-myristate 13-acetate (Sigma-Aldrich, St. Louis, Mo.) in RPMI 1640 medium with 10% fetal bovine serum (v/v), 2 mM L-glutamine, 10 mM HEPES, 0.05 mM 2-mercaptoethanol. Twenty-four hours after the induction, cells were harvested and washed twice with PBS before lysed with lysis buffer (20 mM Tris pH 7.5, 0.5% Nonidet P-40, 5 mM $MgCl_2$, 20 ng/μL tRNA) at 25° C., for 5 min. The lysate was heated at 75° C. for 15 min before testing in a 5' nuclease assay.

Figure 26:
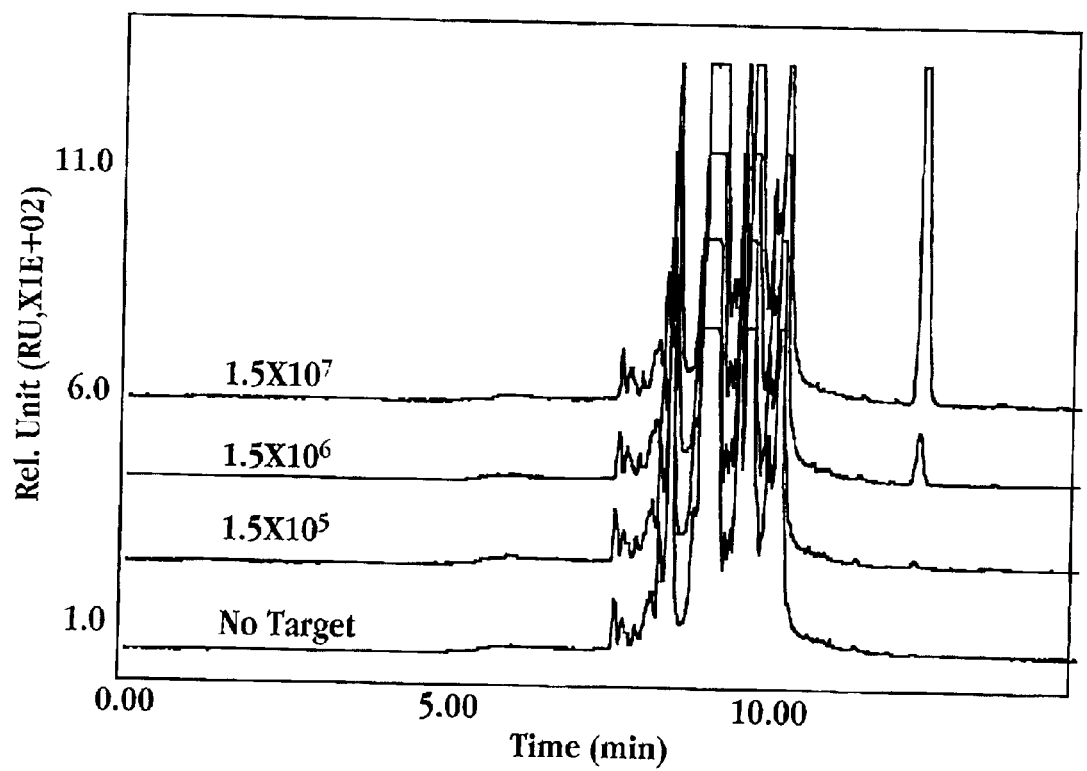
FIG. 26 shows multiple electropherograms from a separation on a 310 analyzer, after an amplification reaction in the presence of probe and primer, and without the addition of avidin.
Figure 27:
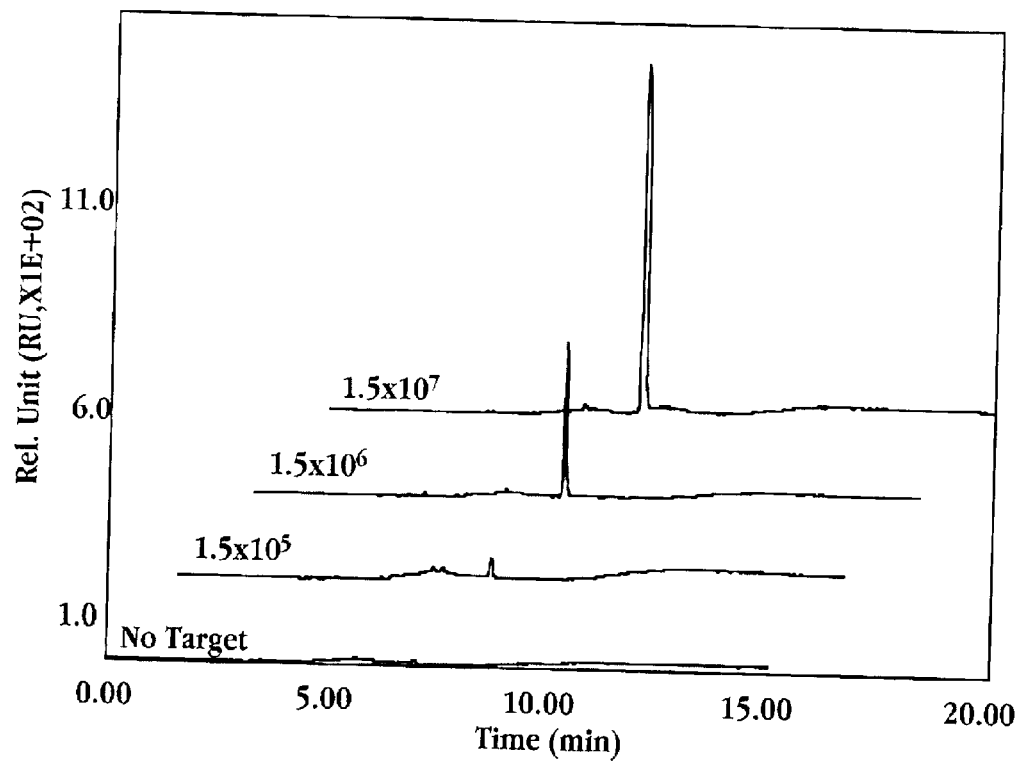
FIG. 27 shows multiple electropherograms from a separation on a 310 analyzer, after an amplification reaction in the presence of probe and primer, and with the addition of avidin.

Ten microliters of a cell lysate was combined with a single stranded upstream invader DNA oligo, (5'CTC-TCA-GTT-CT), a single stranded downstream biotinylated signal DNA oligo (e-tag-labeled), and 2 ng/μL 5' nuclease (Cleavase IX) in 20 μL of buffer (10 mM MOPS pH 7.5, 0.05% Tween-20 and 0.05% Nonidet P-40, 12.5 mM $MgCl_2$, 100 μM ATP, 2 U/μL RNase inhibitor). The reactions were carried out at 60° C. for 4 hours before analysis by capillary electrophoresis. To eliminate background signal, due to the non-specific activity of the enzyme, 1 μL of 1 mg/mL avidin was added to the reactions to remove all the e-tag-labeled uncleaved oligo, or e-tag-labeled non-specifically cleaved oligonucleotides. FIGS. 26 and 27, respectively, show separations that were conducted both with and without the addition of avidin.

Example 10

PCR Amplification with 5' Nuclease Activity Using e-tag Reporters

Exemplary e-tag reporters are shown in FIG. 17. Elution times for some of these reporters on an ABI 3100 using POP4 as the separation matrix are provided in FIG. 6. The e-tag reporters that were prepared were screened to provide 20 candidates that provided sharp separations. 31 e-tag reporters were generated with synthetic targets using the TaqMan (reagents under conditions as shown in the following tabular format. There were 62 reactions with the synthetic targets (one reaction and one negative control for e-tag reporter). Each 25 μL reaction contained 200 nM probe, 500 nM primer, and 5 fM template in 0.5×TaqMan master mix.

All the individual reactions were then run on an ABI 3100 using POP4 as the separation matrix. The samples were diluted 1:20 in 0.5×TaqMan buffer and 1 μL of avidin (10 mg/mL) was added to bind to any intact probe. The sample was further diluted 1:2 with formamide before injecting the sample into the ABI 3100 capillaries. The following are the conditions used with the ABI 3100 for the separation:

| Temperature | 60° C. |
| --- | --- |
| Pre-run voltage | 15 kV |
| Pre-run time | 180 sec |
| Matrix | POP4 |
| Injection voltage | 3 kV |

-continued

| Injection time | 10 sec |
| --- | --- |
| Run voltage | 15 kV |
| Run time | 900 sec |
| Run module | e-tag reporter POP4 |
| Dye set | D |

Subsequent separation of multiple e-tag reporters in a single run was accomplished as shown in FIG. 8, the structures of which are identified in FIG. 17.

Example 11 e-tag Reporter Assay for Protein Analysis

A. Labeling of aminodextran (MW~500,000) with e-tag Reporter and Biotin

Aminodextran was used as a model for demonstrating e-tag reporter release in relation to a high molecular weight molecule, which also serves as a model for proteins. The number of amino groups for 10 mg aminodextran was calculated as $2 \times 10^{-8}$ moles. For a ratio of 1:4 biotin to e-tag reporter, the number of moles of biotin NHS ester employed was $1.85 \times 10^{-6}$, and the number of moles of maleimide NHS ester was $7.4 \times 10^{-6}$. 10.9 mg of aminodextran was dissolved in 6 mL of 0.1% PBS buffer. 10 mg of Biotin-x-x NHS ester and 23.7 mg of EMCS were dissolved together in 1 mL of DMF, and added in 50 μL portions at 30 min intervals to the aminodextran solution while it was stirring and keeping away from the light. After the final addition of the DMF solution, the mixture was kept overnight (while stirring and away from the light). Then, the mixture was dialyzed using a membrane with a molecular weight cut-off of 10,000 Daltons. The membrane was immersed in a beaker containing 2 L of water while stirring. The water was changed four times in a 2 h interval. The membrane was kept in the water overnight (while stirring and keeping away from the light). Then the solution was lyophilized and the lyophilized powder was used for e-tag reporter labeling.

B. Reaction of Biotin and Maleimide Labeled aminodextran with the e-tag Reporter, SAMSA.

SAMSA [5-(((2-(and-3)-S-acetylmercapto)succinoyl)amino)fluorescein]was employed as an e-tag reporter to react with maleimide in the aminodextran molecule. For this purpose 0.3 mg (~5.3×10⁻⁹ moles) of biotin and EMCS labeled with aminodextran were dissolved in 10 μl of water and then reacted with 10 times the mol ratio of SAMSA, for the complete conversion of the maleimide to the e-tag reporter. Therefore, 1.1 mg of SAMSA (~1.2×10⁻⁶ moles) is dissolved in 120 μL of 0.1 M NaOH and incubated at room temperature for 15 min (for the activation of the thiol group). Then the excess of NaOH was neutralized by the addition of 2 μL of 6M HCl, and the pH of the solution was adjusted to 7.0 by the addition of 30 μL of phosphate buffer (200 mM, pH 7.0). The activated SAMSA solution was added to the 10 μL solution of the labeled aminodextran and incubated for 1 h. The e-tag reporter labeled aminodextran was purified with gel filtration using Sephadex G-25 (Amersham), and purified samples were collected.

C. The Release of e-tag from Labeled Aminodextran

Figure 28A:
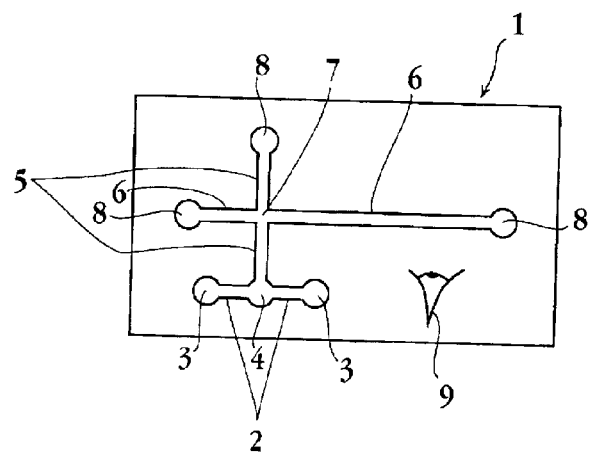
FIGS. 28A–C are schematic illustrations of a $CE^2$ LabCard™ device (28A) and exemplary high voltage configurations utilized in this device for the injection (28B) and separation (28C) of products of an enzyme assay.
Figure 28B:
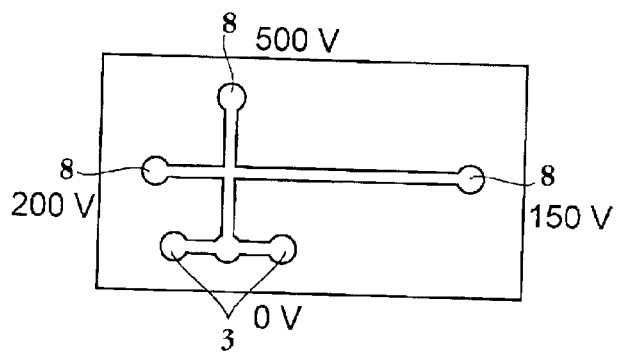
Figure 28C:
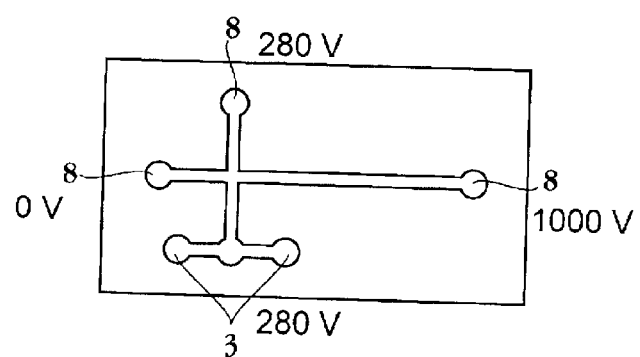

2 μL of streptavidin coated sensitizer beads (100 μg/mL) were added carefully in the dark to the 5 μL of purified labeled aminodextran and incubated in the dark for 15 min. Then the solution was irradiated for 1 min at 680 nm. The release of the e-tag reporter was examined be CE using $CE^2$ LabCard™ device. As shown in FIG. 28A, the $CE^2$ LabCard 1 consists of two parts; evaporation control and injection/ separation. The evaporation control incorporates an evaporation control channel 2 (450 µm wide and 50 µm deep) with two replenishment buffer reservoirs 3 (2 mm in diameter) and the evaporation-controlled sample well 4 (I mm diameter) in the middle of the evaporation control channel. The volume of the replenishment buffer reservoirs are 4.7 µL while the volume of the sample well is only 1.2 µL, and the volume of the channel 2 beneath the middle sample well is about 40 nL. The second part of the $CE^2$ device, which is used for injection and separation, consists of an injection microchannel 5 and a separation microchannel 6, intersecting at a junction 7, and having dimensions of 120 µm wide and 50 µm deep. Both ends of the separation channel and one end or the injection channel connect with buffer reservoirs 8, while the second end of the injection channel connects directly to the evaporation-controlled sample well 4. The channels are enclosed by laminating a film (MT40) to the LabCard™. A detector 9 is positioned 10 mm from the junction. After filling the $CE^2$ LabCard device with separation buffer (20 mM HEPES, pH 7.4 and 0.5% PEO), 300 nL of the assay mixture is added to the sample well 4. The sample was injected into the microchannel junction 7 by applying voltages to the buffer reservoirs as indicated in FIG. 28B. The sample was then separated as is shown in FIG. 28C.

Figure 29:
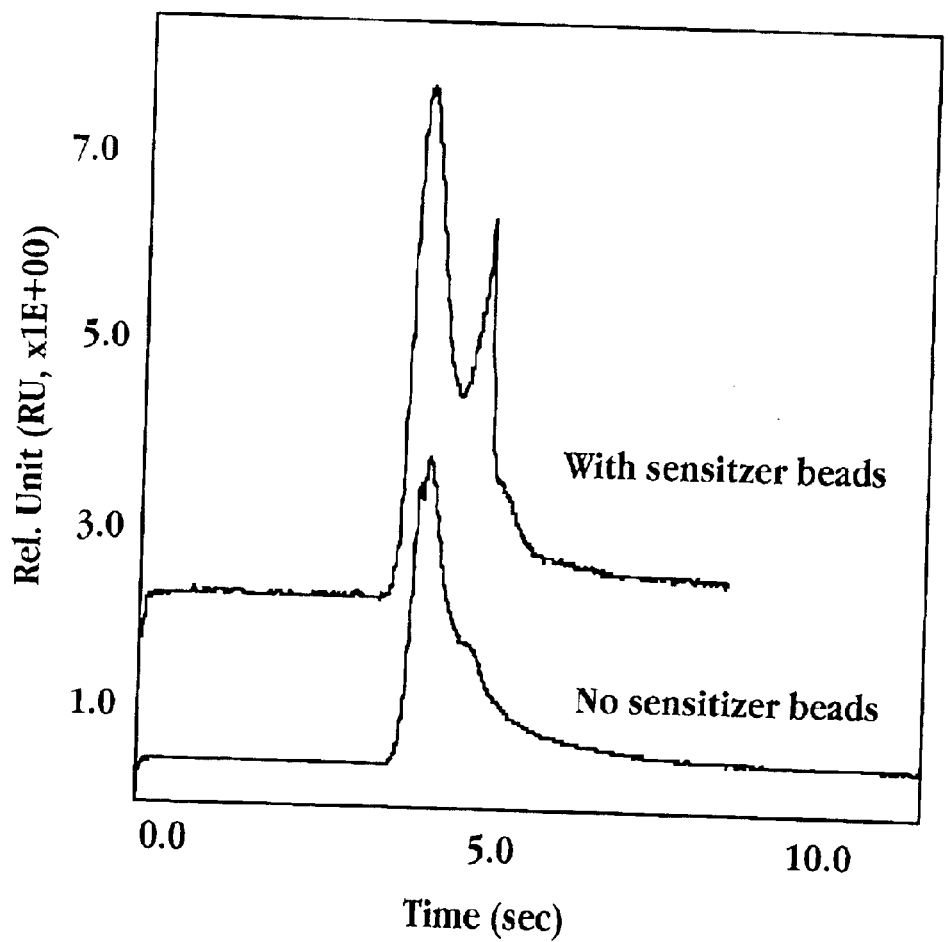
FIG. 29 shows two electropherograms demonstrating e-tag reporter analysis using a $CE^2$ LabCard. The figure shows the separation of purified labeled aminodextran with and without sensitizer beads. The addition of the sensitizer beads lead to the release of the e-tag reporter from the aminodextran using singlet oxygen produced by sensitizer upon the irradiation at 680 nm. Experimental conditions: separation buffer 20 mM HEPES pH=7.4, and 0.5% PEO; voltage configurations as described for FIG. 28; assay mixture had 29 μg/ml streptavidin coated sensitizer beads and irradiated for 1 min at 680 nm using 680±10 nm filter and a 150 W lamp.
Figure 30:
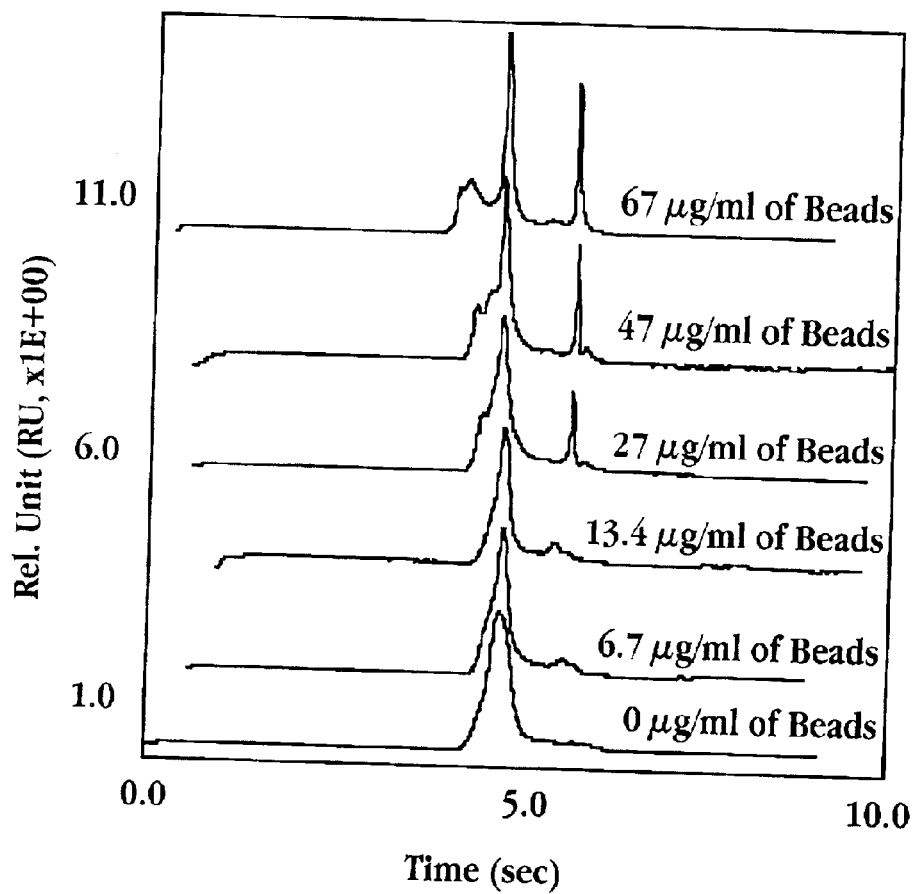
FIG. 30 shows multiple electropherograms demonstrating e-tag reporter analysis using a $CE^2$ LabCard. The figure shows the separation of purified labeled aminodextran using different concentrations of sensitizer beads. The higher concentration of sensitizer beads leads to the higher release of e-tag reporters from the labeled aminodextran. Experimental conditions: separation buffer 20.0 mM HEPES pH=7.4, and 0.5% PEO; voltage configurations as described for FIG. 28; assay mixture was irradiated for 1 min at 680 nm using 680±10 nm filter and a 150 W lamp.
Figure 31:
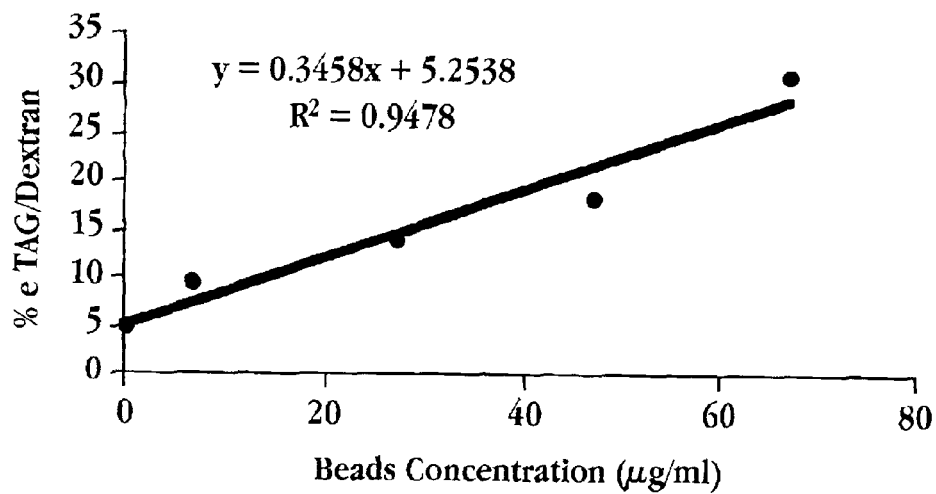
FIG. 31 depicts the linear calibration curve for the release of e-tag reporters as a function of the sensitizer bead concentration. Results were obtained using a $CE^2$ LabCard. Experimental conditions: separation buffer 20.0 mM HEPES pH=7.4, and 0.5% PEO; voltage configurations as described for FIG. 28; assay mixture was irradiated for 1 min at 680 nm using 680±10 nm filter and a 150 W lamp.
Figure 32:
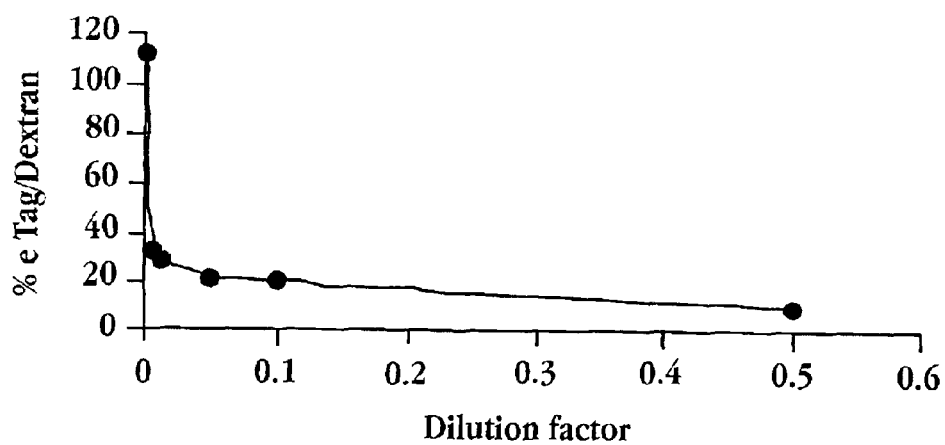
FIG. 32 shows a data curve of the effect of the concentration of labeled aminodextran on the e-tag reporter release. As demonstrated in this figure, the lower concentration of labeled aminodextran for a given concentration of sensitizer beads leads to more efficient e-tag reporter release Results were obtained using a $CE^2$ LabCard. Experimental conditions: separation buffer 20.0 mM HEPES pH=7.4, and 0.5% PEO; voltage configurations as described for FIG. 28; assay mixture had 29 μg/ml of sensitizer beads and was irradiated for 1 min at 680 nm using 680±10 nm filter and a 150 W lamp.

FIG. 29 shows the electropherograms of purified labeled aminodextran with and without sensitizer beads. As shown, the addition of the sensitizer beads leads to the release of the e-tag reporter from the aminodextran using singlet oxygen produced by the sensitizer upon irradiation at 680 nm. In order to optimize the irradiation time, different tubes containing the same mixture of beads and sensitizer were irradiated for different lengths of time ranging from 1 to 10 min. There is no significant increase in the e-tag reporter release for irradiation times longer than 1 min. FIG. 30 shows the effect of sensitizer bead concentration on e-tag reporter release. As depicted in FIG. 30, a higher concentration of sensitizer beads leads to greater release of e-tag reporters from the labeled aminodextran. FIG. 31 depicts a linear calibration curve for the release of e-tag reporters as a function of sensitizer bead concentration. In addition, the effect of the concentration of labeled aminodextran on e-tag reporter release was also examined, with the results shown in FIG. 32. As can be seen, a lower concentration of labeled aminodextran for a given concentration of sensitizer beads leads to more efficient e-tag reporter release (or higher ratio of e-tag reporter released to the amount of labeled aminodextran).

It is evident from the above results that the subject inventions provide powerful ways of preparing compositions for use in multiplexed determinations and methods for performing multiplexed determinations using such compositions. The methods provide for homogeneous and heterogeneous protocols, both with nucleic acids and proteins, as exemplary of other classes of compounds. In the nucleic acid determinations, SNP determinations are greatly simplified where the protocol can be performed in only one to four vessels and a large number of SNPs readily determined within a short period of time with great efficiency and accuracy. For other sequences, genomes can be investigated from both prokaryotes and eukaryotes, including for the prokaryotes, drug resistance, species, strain, etc., and for the eukaryotes, species, cell type, response to external stimuli, e.g. drugs, physical changes in environment, etc., mutations, chiasmas, etc. With proteins, one can determine the response of the host cell, organelles or the like to changes in the chemical and physical environments in relation to a plurality of pathways, changes in the surface protein population, changes due to aging, neoplasia, activation, or other naturally occurring phenomenon, where the amount of protein can be quantitated.

Particularly as to nucleic acid determinations, the subject e-tag reporters can be synthesized conveniently along with the synthesis of the oligonucleotides used as probes, primers, etc., where the e-tag reporter is released in the presence of the homologous target sequence. Kits of building blocks or e-tag reporters are provided for use in the different determinations.

It is further evident from the above results that the subject invention provides an accurate, efficient and sensitive process, as well as compositions for use in the process, to perform multiplexed reactions. The protocols provide for great flexibility in the manner in which determinations are carried out and maybe applied to a wide variety of situations involving haptens, antigens, nucleic acids, cells, etc., where one may simultaneously perform a number of determinations on a single or plurality of samples and interrogate the samples for a plurality of events. The events may vary from differences in nucleic acid sequence to proteomics to enzyme activities. The results of the determination are readily read in a simple manner using electrophoresis or mass spectrometry. Systems are provided where the entire process, after addition of the sample and reagents, may be performed under the control of a data processor with the results automatically recorded.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A set of electrophoretic probes for detecting the presence or absence of one or more of a plurality nucleotide sequences in a sample, the set comprising a plurality of electrophoretic probes selected from the group defined by the formula:

(D, M)-N-T wherein:
- (D, M)-N is an e-tag reporter released from an electrophoretic probe of the set upon digestion of the electrophoretic probe by a nuclease, the e-tag reporter having a charge;
- D is a detection moiety;
- M is a mobility modifier consisting of from 1 to 500 atoms selected from the group consisting of carbon, hydrogen, oxygen, phosphorus, nitrogen, sulfur, and boron;
- N is a nucleotide; and
- T is an oligonucleotide specific for at least one of the plurality of nucleotide sequences, each T having a length in the range of from 12 to 60 nucleotides such that at least one nucleotide of T has a capture ligand attached;
- and wherein each e-tag reporter of the plurality of electrophoretic probes has a distinct charge/mass ratio so that e-tag reporters of different electrophoretic probes form distinct peaks in an electropherogram upon electrophoretic separation;
- and wherein the capture ligand specifically binds to a capture agent that has a charge opposite to that of e-tag reporters so that undigested electrophoretic probes are excluded from the electropherogram.

2. The set of claim 1 wherein said plurality is in the range of from 5 to 100 and wherein M is a mobility modifier consisting of from 1 to 300 atoms selected from the group consisting of carbon, hydrogen, oxygen, phosphorus, nitrogen, sulfur, and boron.

3. The set of claim 2 wherein D is a fluorophore, chromophore, or an electrochemical label.

4. The set according to claim 1, 2, or 3 wherein said formula is D-M-N-T.

5. The set of claim 4 wherein said capture ligand is biotin and wherein said capture agent is avidin.

6. The set of claim 4 wherein said oligonucleotide has at least one nuclease-resistant linkage.

7. The set of claim 4 wherein said fluorophore is a fluorescern.

8. The set of claim 4 wherein M consists of from 2 to 100 atoms selected from the group consisting of carbon, hydrogen, oxygen, phosphorus, nitrogen, sulfur, and boron.

9. A set of electrophoretic probes for detecting the presence or absence of one or more of a plurality nucleotide sequences in a sample, the set comprising a plurality of electrophoretic probes selected from the group defined by the formula:

(D, M)-N-T wherein:
- (D, M)-N is an e-tag reporter released from an electrophoretic probe of the set upon digestion of the electrophoretic probe by a nuclease, the e-tag reporter having a charge;
- D is a detection moiety;
- M is a mobility modifier having a molecular weight of between 35 and 1500 daltons;
- N is a nucleotide; and
- T is an oligonucleotide specific for at least one of the plurality of nucleotide sequences, each T having a length in the range of from 12 to 60 nucleotides such that at least one nucleotide of T has a capture ligand attached;
- and wherein each e-tag reporter of the plurality of electrophoretic probes has a distinct charge/mass ratio so that e-tag reporters of different electrophoretic probes form distinct peaks in an electropheroeram upon electrophoretic separation;
- and wherein the capture ligand specifically binds to a capture agent that has a charge opposite to that of e-tag reporters so that undigested electrophoretic probes are excluded from the electropherogram.

10. The set of claim 9 wherein D is a fluorophore, chromophore, or an electrochemical label.

11. The set according to claim 10 wherein said formula is D-M-N-T.

12. The set of claim 11 wherein said capture ligand is biotin and wherein said capture agent is avidin.

13. The set of claim 11 wherein said e-tag reporter is selected from the group consisting of the following compounds:

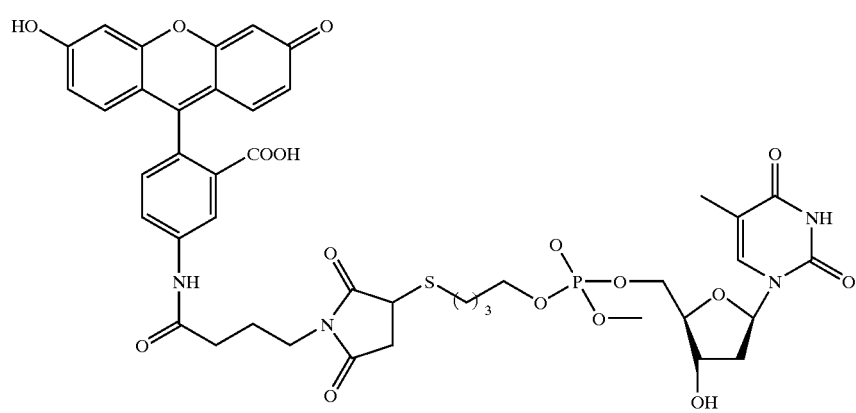
1
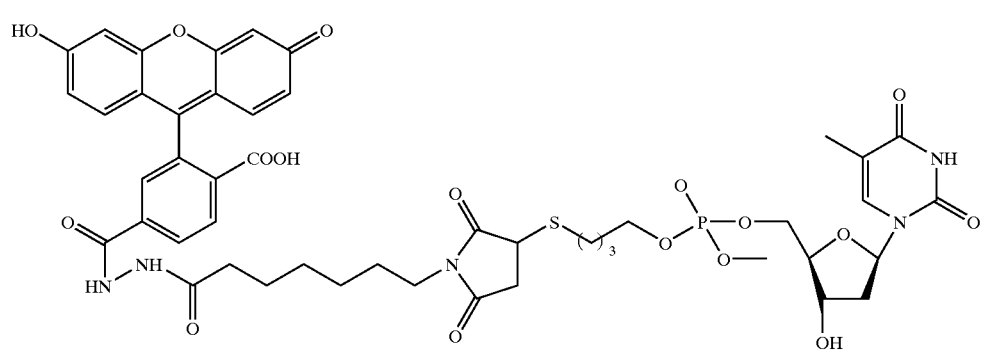
2
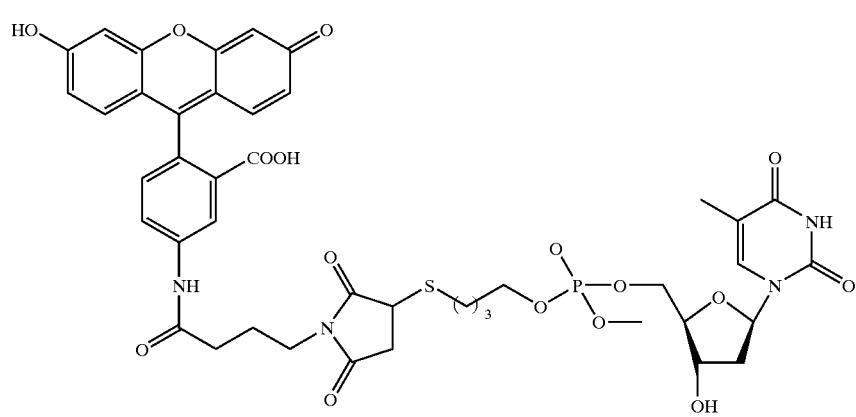
3
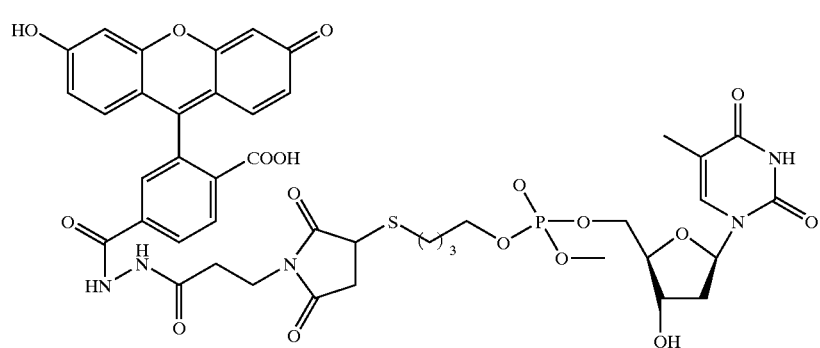
4

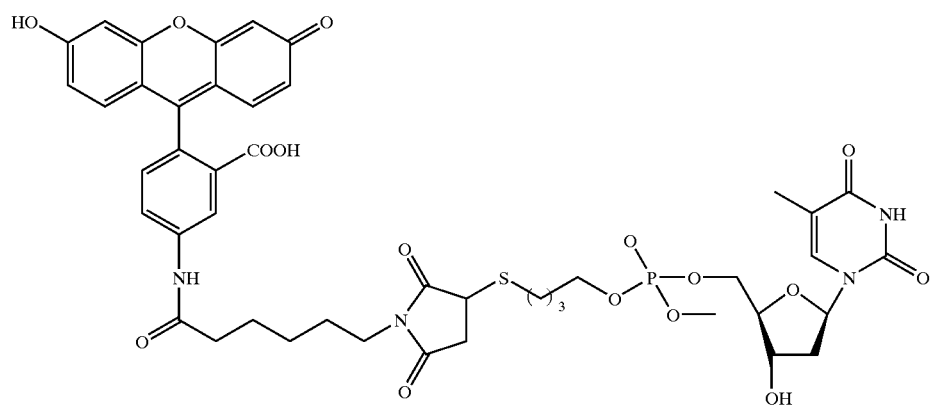
5
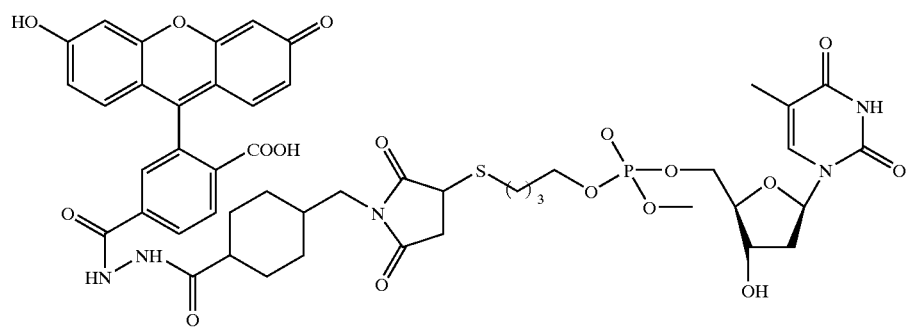
6
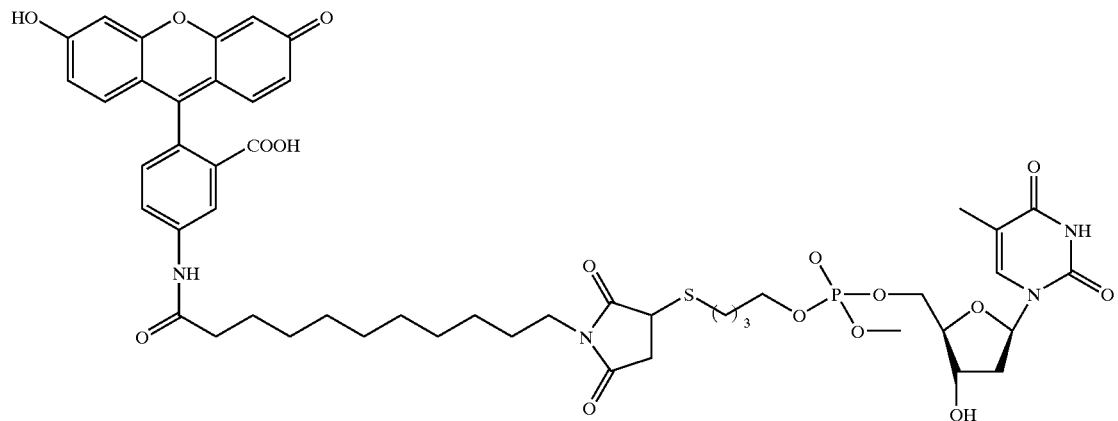
7
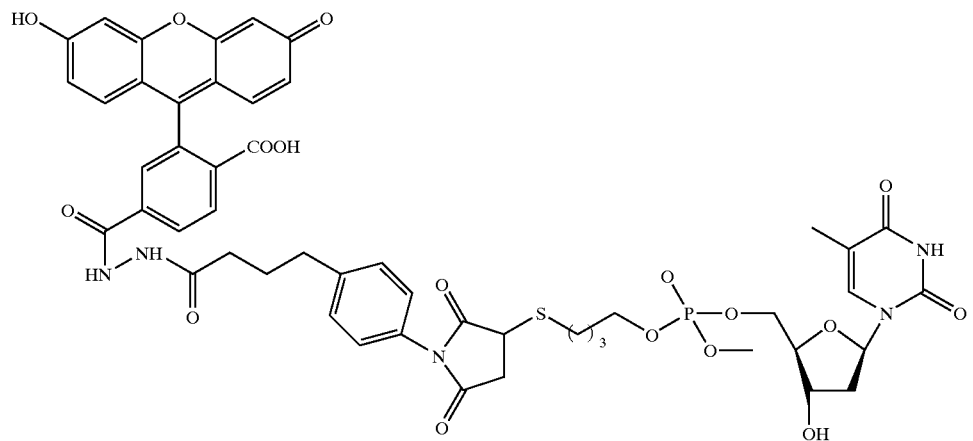
8

-continued
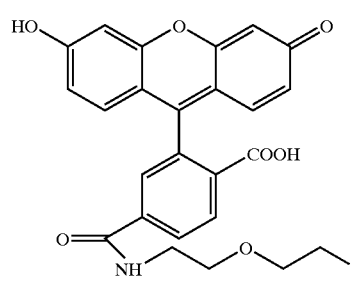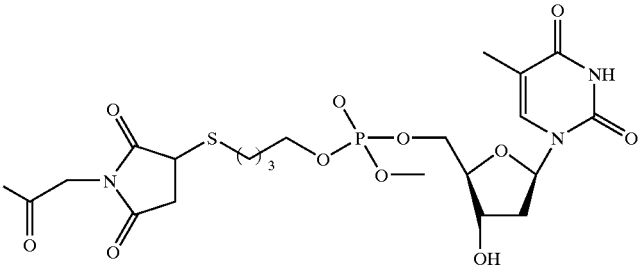
9
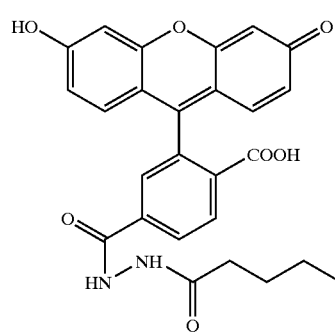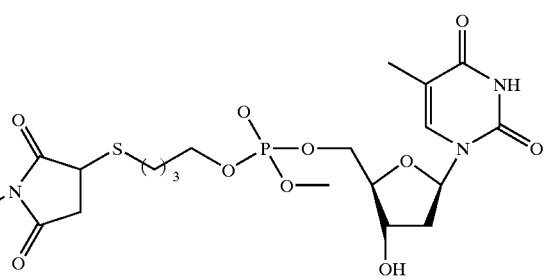
10
* * * * *

SEQUENCE LISTING

<160> NUMBER OF SEQ ID NOS: 18

<210> SEQ ID NO 1
<211> LENGTH: 16
<212> TYPE: DNA
<213> ORGANISM: Artificial Sequence
<220> FEATURE:

```
<223> OTHER INFORMATION: synthesized oligonucleotide

<400> SEQUENCE: 1
tcaccacatc ccagtg                                                   16

<210> SEQ ID NO 2
<211> LENGTH: 16
<212> TYPE: DNA
<213> ORGANISM: Artificial Sequence
<220> FEATURE:
<223> OTHER INFORMATION: synthesized oligonucleotide

<400> SEQUENCE: 2
gagggaggtt tggctg                                                   16

<210> SEQ ID NO 3
<211> LENGTH: 22
<212> TYPE: DNA
<213> ORGANISM: Artificial Sequence
<220> FEATURE:
<223> OTHER INFORMATION: synthesized oligonucleotide
<221> NAME/KEY: misc_feature
<222> LOCATION: (22)...(22)
<223> OTHER INFORMATION: 3' nucleotide linked to tetramethyl rhodamine

<400> SEQUENCE: 3
ccagcaacca atgatgcccg tt                                            22

<210> SEQ ID NO 4
<211> LENGTH: 22
<212> TYPE: DNA
<213> ORGANISM: Artificial Sequence
<220> FEATURE:
<223> OTHER INFORMATION: synthesized oligonucleotide
<221> NAME/KEY: misc_feature
<222> LOCATION: (1)...(1)
<223> OTHER INFORMATION: 5' nucleotide linked to fluorescein
<221> NAME/KEY: misc_feature
<222> LOCATION: (22)...(22)
<223> OTHER INFORMATION: 3' nucleotide linked to tetramethyl rhodamine

<400> SEQUENCE: 4
ccagcaagca ctgatgcctg tt                                            22

<210> SEQ ID NO 5
<211> LENGTH: 4
<212> TYPE: PRT
<213> ORGANISM: Artificial Sequence
<220> FEATURE:
<223> OTHER INFORMATION: peptide linker

<400> SEQUENCE: 5

Lys Lys Ala Ala
 1

<210> SEQ ID NO 6
<211> LENGTH: 4
<212> TYPE: PRT
<213> ORGANISM: Artificial Sequence
<220> FEATURE:
<223> OTHER INFORMATION: peptide linker
```

```
<400> SEQUENCE: 6

Lys Lys Lys Ala
 1

<210> SEQ ID NO 7
<211> LENGTH: 4
<212> TYPE: PRT
<213> ORGANISM: Artificial Sequence
<220> FEATURE:
<223> OTHER INFORMATION: peptide linker

<400> SEQUENCE: 7

Lys Lys Lys Lys
 1

<210> SEQ ID NO 8
<211> LENGTH: 25
<212> TYPE: DNA
<213> ORGANISM: Artificial Sequence
<220> FEATURE:
<223> OTHER INFORMATION: synthesized oligonucleotide

<400> SEQUENCE: 8
gaccaggaaa tagagaggaa atgta                                          25

<210> SEQ ID NO 9
<211> LENGTH: 27
<212> TYPE: DNA
<213> ORGANISM: Artificial Sequence
<220> FEATURE:
<223> OTHER INFORMATION: synthesized oligonucleotide

<400> SEQUENCE: 9
gaaggagaag gaagagttgg tattatc                                        27

<210> SEQ ID NO 10
<211> LENGTH: 21
<212> TYPE: DNA
<213> ORGANISM: Artificial Sequence
<220> FEATURE:
<223> OTHER INFORMATION: synthesized oligonucleotide

<400> SEQUENCE: 10
ttgggctcag atctgtgata g                                              21

<210> SEQ ID NO 11
<211> LENGTH: 27
<212> TYPE: DNA
<213> ORGANISM: Artificial Sequence
<220> FEATURE:
<223> OTHER INFORMATION: synthesized oligonucleotide

<400> SEQUENCE: 11
catctaggta tccaaaagga gagtcta                                        27

<210> SEQ ID NO 12
<211> LENGTH: 27
<212> TYPE: DNA
<213> ORGANISM: Artificial Sequence
<220> FEATURE:
<223> OTHER INFORMATION: synthesized oligonucleotide
```

```
<400> SEQUENCE: 12
cggtatatag ttcttcctca tgctatt                                              27

<210> SEQ ID NO 13
<211> LENGTH: 20
<212> TYPE: DNA
<213> ORGANISM: Artificial Sequence
<220> FEATURE:
<223> OTHER INFORMATION: synthesized oligonucleotide

<400> SEQUENCE: 13
gcaagatctt cgccttactg                                                      20

<210> SEQ ID NO 14
<211> LENGTH: 32
<212> TYPE: DNA
<213> ORGANISM: Artificial Sequence
<220> FEATURE:
<223> OTHER INFORMATION: probe
<221> NAME/KEY: misc_feature
<222> LOCATION: (1)...(1)
<223> OTHER INFORMATION: e-tag10s modification to the 5' nucleotide

<400> SEQUENCE: 14
ttccattttc tttttagagc agtatacaaa ga                                        32

<210> SEQ ID NO 15
<211> LENGTH: 32
<212> TYPE: DNA
<213> ORGANISM: Artificial Sequence
<220> FEATURE:
<223> OTHER INFORMATION: probe
<221> NAME/KEY: misc_feature
<222> LOCATION: (1)...(1)
<223> OTHER INFORMATION: e-tag10as modification to the 5' nucleotide

<400> SEQUENCE: 15
tctttgtata ctgctctaaa aagaaaatgg aa                                        32

<210> SEQ ID NO 16
<211> LENGTH: 28
<212> TYPE: DNA
<213> ORGANISM: Artificial Sequence
<220> FEATURE:
<223> OTHER INFORMATION: probe
<221> NAME/KEY: misc_feature
<222> LOCATION: (1)...(1)
<223> OTHER INFORMATION: e-tag11s modification to the 5' nucleotide

<400> SEQUENCE: 16
aaactccagc atagatgtgg atagcttg                                             28

<210> SEQ ID NO 17
<211> LENGTH: 28
<212> TYPE: DNA
<213> ORGANISM: Artificial Sequence
<220> FEATURE:
<223> OTHER INFORMATION: probe
<221> NAME/KEY: misc_feature
<222> LOCATION: (1)...(1)
<223> OTHER INFORMATION: e-tag11as modification to the 5' nucleotide

<400> SEQUENCE: 17
caagctatcc acatctatgc tggagttt                                             28
```

```
<210> SEQ ID NO 18
<211> LENGTH: 23
<212> TYPE: DNA
<213> ORGANISM: Artificial Sequence
<220> FEATURE:
<223> OTHER INFORMATION: probe
<221> NAME/KEY: misc_feature
<222> LOCATION: (1)...(1)
<223> OTHER INFORMATION: e-tag13as modification to the 5' nucleotide

<400> SEQUENCE: 18
aactgcttgt ggccatggct tag                                              23
```